(12) United States Patent
Murphy et al.

(10) Patent No.: US 11,503,812 B2
(45) Date of Patent: *Nov. 22, 2022

(54) NON-HUMAN ANIMALS HAVING HUMANIZED FC-GAMMA RECEPTORS

(71) Applicant: Regeneron Pharmaceuticals, Inc., Tarrytown, NY (US)

(72) Inventors: Andrew J. Murphy, Croton-On-Hudson, NY (US); Lynn Macdonald, Harrison, NY (US); Cagan Gurer, Chappaqua, NY (US); Karolina A. Meagher, Yorktown Heights, NY (US); Naxin Tu, Pleasantville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 374 days.

This patent is subject to a terminal disclaimer.

(21) Appl. No.: 16/723,733

(22) Filed: Dec. 20, 2019

(65) Prior Publication Data

US 2020/0288684 A1 Sep. 17, 2020

Related U.S. Application Data

(63) Continuation of application No. 15/277,092, filed on Sep. 27, 2016, now Pat. No. 10,555,507, which is a continuation of application No. 14/681,617, filed on Apr. 8, 2015, now Pat. No. 9,474,255.

(60) Provisional application No. 61/977,037, filed on Apr. 8, 2014.

(51) Int. Cl.
*A01K 67/027* (2006.01)
*C07K 14/735* (2006.01)

(52) U.S. Cl.
CPC .... *A01K 67/0278* (2013.01); *C07K 14/70535* (2013.01); *A01K 2207/15* (2013.01); *A01K 2217/072* (2013.01); *A01K 2227/105* (2013.01); *A01K 2267/01* (2013.01); *A01K 2267/0337* (2013.01); *A01K 2267/0387* (2013.01)

(58) Field of Classification Search
CPC ................................................ A01K 67/0278
See application file for complete search history.

(56) References Cited

U.S. PATENT DOCUMENTS

| | | | |
|---|---|---|---|
| 5,859,312 A | 1/1999 | Littman et al. | |
| 5,877,396 A | 3/1999 | Ravetch et al. | |
| 6,111,166 A | 8/2000 | van de Winkel | |
| 6,294,347 B1 | 9/2001 | Peltz et al. | |
| 6,676,927 B1 | 1/2004 | Ravetch | |
| 7,265,261 B2 | 9/2007 | Takai et al. | |
| 7,309,810 B2 | 12/2007 | Takai et al. | |
| 7,351,875 B2 | 4/2008 | Hogarth et al. | |
| 7,402,728 B2 | 7/2008 | Chan et al. | |
| 7,579,170 B2 | 8/2009 | Beliard et al. | |
| 7,713,524 B2 | 5/2010 | Bourel et al. | |
| 7,754,482 B2 | 7/2010 | Riley et al. | |
| 7,816,082 B2 | 10/2010 | Han et al. | |
| 8,912,385 B2 | 12/2014 | Meagher | |
| 9,474,255 B2 | 10/2016 | Murphy et al. | |
| 10,555,507 B2 * | 2/2020 | Murphy | A01K 67/0278 |
| 2004/0154044 A1 | 8/2004 | Fraichard et al. | |
| 2008/0003225 A1 | 1/2008 | Vie et al. | |
| 2009/0098124 A1 | 4/2009 | Stavenhagen | |
| 2010/0035280 A1 | 2/2010 | Kawai | |
| 2013/0111616 A1 | 5/2013 | MacDonald et al. | |
| 2013/0111617 A1 | 5/2013 | MacDonald et al. | |
| 2013/0117873 A1 | 5/2013 | Wang et al. | |
| 2014/0134662 A1 | 5/2014 | Flavell et al. | |
| 2014/0245466 A1 | 8/2014 | MacDonald et al. | |
| 2014/0245467 A1 | 8/2014 | MacDonald et al. | |
| 2015/0089678 A1 | 3/2015 | Murphy et al. | |
| 2015/0143558 A1 | 5/2015 | McWhirter et al. | |
| 2015/0143559 A1 | 5/2015 | McWhirter et al. | |

FOREIGN PATENT DOCUMENTS

| | | |
|---|---|---|
| EP | 2123754 A1 | 11/2009 |
| WO | WO-1995/028959 A1 | 11/1995 |
| WO | WO-1999/000010 A2 | 1/1999 |
| WO | WO-2009/158696 A1 | 12/2009 |

OTHER PUBLICATIONS

Alevy, et al., "CD32A (FcgRIIA) mRNA expression and regulation in blood monocytes and cell lines," Mol Immunol, 29(11): 1289-1297 (1992).

Allen, et al., "Isolation and Expression of Functional High-Affinity Fc Receptor Complementary DNAs," Science, 243(4889): 378-381 (1989).

Amsbio: Fc receptor family proteins. Downloaded Sep. 2018.

Anderson, "Isolation of the receptor for IgG from a human monocyte cell line (U937) and from human peripheral blood monocytes," J Exp Med, 156(6): 1794-1805 (1982).

Anselmino, et al., "Human basophils selectively express the FcgRII (CDw32) subtype of IgG receptor," J Allergy Clin Immun, 84(6): 907-914 (1989).

Asaoka, et al., "The Binding of Soluble Recombinant Human FCY Receptor I for Human Immunoglobulin G is Conferred by its First and Second Extracellular Domains," Mol Immunol, 29(11): 1407-1413 (1992).

Barnes, et al., "FcgRI-Deficient Mice Show Multiple Alterations to Inflammatory and Immune Responses," Immunity, 16(3): 379-389 (2002).

Bolland, "A Newly Discovered Fc Receptor that Explains IgG-Isotype Disparities in Effector Responses," Immunity, 23(1): 2-4 (2005).

Bonnerot, et al., "Role of B cell receptor Ig alpha and Ig beta subunits in MHC class II-restricted antigen presentation," Immunity, 3(3): 335-347 (1995).

(Continued)

*Primary Examiner* — Scott Long

(74) *Attorney, Agent, or Firm* — Foley Hoag LLP; Brendan T. Jones

(57) ABSTRACT

Genetically modified mice and methods and compositions for making and using the same are provided, wherein the genetic modification comprises humanization of an FcγRI protein.

11 Claims, 35 Drawing Sheets

Specification includes a Sequence Listing.

(56) References Cited

OTHER PUBLICATIONS

Boros P. et al., "Fc Receptors" Encyclopedia of Life Sciences, pp. 1-8 (2008).
Brooks, et al., "Structure and expression of human IgG FcRII (CD32): Functional Heterogeneity is Encoded by the Alternatively Spliced Products of Multiple Genes," J Exp Med, 170(4): 1369-1385 (1989).
Bruhns, "Properties of mouse and human IgG receptors and their contribution to disease models," Blood, 119(24): 5640-5649 (2012).
Cassatella, et al., "Fc gamma R (CD16) interaction with ligand induces Ca2+ mobilization and phosphoinositide turnover in human natural killer cells: Role of Ca2+ in FcgR(CD16)—induced transcription and expression of lymphokine genes," J Exp Med, 169(2): 549-567 (1989).
Coggeshall, "Inhibitory signaling by B cell Fc gamma RIIb," Curr Opini Immunol, 10(3): 308-312 (1998).
Cohen-Solal, et al., "Fc gamma receptors," Immunol Lett, 92(3): 199-205 (2004).
De Haas, "IgG-Fc receptors and the clinical relvance of their polymorphisms," Wiener Klinische Wochenschrift, 113(20-21): 825-831 (2001).
Deo, et al., "Clinical significance of IgG Fc receptors and Fc gamma R-directed immunotherapies," Immunol Today, 18(3): 127-135 (1997).
Desjarlais, et al., "Optimizing engagement of the immune system by anti-tumor antibodies: an engineer's perspective," Drug Discov Today, 12(21-22): 898-910 (2007).
Desoize, "Antibodies in cancer treatment," Crit Rev Oncol Hematol, 62(1): 23-25 (2007).
Extended European Search Report for EP Application No. 20156988.6 dated May 13, 2020.
Fc Receptor, Wikipedia, retrieved Dec. 9, 2016, from <https://en.wikipedia.org/wiki/Fc_receptor>.
Fleit, et al., "Human neutrophil Fcg receptor distribution and structure," PNAS, 79(10): 3275-3279 (1982).
Gessner, et al., "The IgG Fc receptor family," Annals Hematol, 76(6): 231-248 (1998).
Getahun, et al., "How antibodies act as natural adjuvants," Immunol Lett 104(1): 38-45 (2006).
Griggs, et al., "The state of the art: immune-mediated mechanisms of monoclonal antibodies in cancer therapy," Brit J Cancer, 101 (11): 1807-1812 (2009).
Guyre, et al., "Increased potency of Fc-receptor-targeted antigens," Cancer Immunol Immunother, 45(3-4): 146-148 (1997).
Harari et al., "Bridging the species divide: Transgenic mice humanized for type-I interferon response," PLOS One, 9(1): e845259 (2014).
Harrison, et al., "High affinity IgG binding by Fc gamma RI (CD64) is modulated by two distinct IgSF domains and the transmembrane domain of the receptor," Protein Engineer, 11(3): 225-232 (1998).
Hazenbos, et al., "Impaired IgG-Dependent Anaphylaxis and Arthus Reaction in FcgRIII (CD16) Deficient Mice," Immunity, 5(2): 181-188 (1996).
Heijnen, et al., "A Human FcgRI/CD64 Transgenic Model for In Vivo Analysis of (Bispecific) Antibody Therapeutics," J Hemotother, 4(5): 351-356 (1995).
Heijnen, et al., "Antigen Targeting to Myeloid-specific Human FcgRI/CD64 Triggers Enhanced Antibody Responses in Transgenic Mice," J Clin Invest, 97(2): 331-338 (1996).
Heijnen, et al., "Human IgG Fc Receptors," Int Rev Immunol, 16(1-2): 29-55 (1996).
Heyman, "Regulation of Antibody Responses via Antibodies, Complement, and Fc Receptors," Ann Rev Immunol, 18(1): 709-737 (2000).
Hibbs, et al., "Molecular cloning of a human immunoglobulin G Fc receptor," PNAS, 85(7): 2240-2244 (1988).
Hogarth, "Fc receptors are major mediators of antibody based inflammation in autoimmunity," Curr Opin Immunol, 14(6): 798-802 (2002).

Honeychurch, et al., "Therapeutic Efficacy of FcgRI/CD64-directed Bispecific Antibodies in B-cell Lymphoma," Blood, 96(10): 3544-3552 (2000).
Hulett, et al. "Molecular Basis of Fc Receptor Function," Adv Immunol, 57: 1-127 (1994).
International Search Report for International Application No. PCT/US2010/060925 dated Mar. 14, 2011.
Kuster, et al., "Characterization and expression of the gene for the human Fc receptor g subunit," J Biol Chem, 265(11): 6448-6452 (1990).
Looney, et al., "Identification of a second class of IgG Fc receptors on human neutrophils," J Exp Med, 163(4): 826-836 (1986).
Louis, et al., "Association between polymorphism in IgG Fc receptor IIIA coding gene and biological response to infliximab in Crohn's disease," Aliment Pharm Ther 19(5): 511-519 (2004).
Malbec, et al., "Negative regulation of hematopoietic cell activation and proliferation by Fc gamma RIIB," Curr Top Microbiol, 244: 13-27 (1999).
Masuda, et al., "Association of all Three Types of FcgR (CD64, CD32, and CD16) with a g-Chain Homodimer in Cultured Human Monocytes," J Immunol, 151(12): 7188-7195 (1993).
Masuda, et al., "Enhanced binding affinity for FcgRIIIA of fucose-negative antibody is sufficient to induce maximal antibody-dependent cellular cytotoxicity," Mol Immunol, 44(12): 3122-3131 (2007).
McKenzie, "Humanized mouse models of FcR clearance in immune platelet disorders," Blood Reviews 16(1): 3-5 (2002).
McKenzie, et al., "The Role of the Human Fc Receptor FcgRIIA in the Immune Clearance of Platelets: A Transgenic Mouse Model," J Immunol, 162(7): 4311-4318 (1999).
Meyer, et al., "Bevacizumab immune complexes activate platelets and induce thrombosis in FCGR2A transgenic mice," J Thromb Haemost 7(1): 171-181 (2008).
Morgan, et al., "Analysis of Fcγ receptor haplotypes in rheumatoid arthritis: FCGR3A remains a major susceptibility gene at this locus, with an additional contribution from FCGR3B," Arthritis Res Ther, 8 (1): 1 (2005).
Morgan, et al., "Association of FCGR2A and FCGR2A-FCGR3A haplotypes with susceptibility to giant cell arteritis," Arthritis Res Ther, 8(4): 1 (2006).
Muller, "Ten years of gene targeting: targeted mouse mutants, from vector design to phenotype analysis," Meeh Develop, 82(1): 3-21 (1999).
Nimmerjahn, et al., "Divergent Immunoglobulin G Subclass Activity Through Selective Fc Receptor Binding," Science, 310(5753): 1510-1512 (2005).
Nimmerjahn, et al., "Fc gamma receptors as regulators of immune responses," Nat Rev, 8(1): 34-47 (2008).
Nimmerjahn, et al., "Fc gamma Receptors: Old Friends and New Family Members," Immunity, 24(1): 19-28 (2006).
Nimmerjahn, et al., "Fc gamma RIV: A Novel FcR with Distinct IgG Subclass Specificity," Immunity, 23(1): 41-51 (2005).
Nimmerjahn, et al., "Fc-Receptors as Regulators of Immunity," Adv Immunol, 96(Ch.5): 179-204 (2007).
Omi, et al., "Absence of Association between the Fcg Receptor IIIA-176F/V Polymorphism and the Severity of Malaria in Thai," Jap J Infect Dis, 55(5): 167-169 (2002).
Otten, et al., "Experimental Antibody Therapy of Liver Metastases Reveals Functional Redundancy between Fc gamma RI and Fc gamma RIV," J Immunol, 181 (10): 6829-6836 (2008).
Ouma, et al., "Association of Fc gamma receptor IIA (CD32) polymorphism with malarial anemia and high-density parasitemia in infants and young children," Am J Trop Med Hyg, 74(4): 573-577 (2006).
Pan, et al., "Genetic susceptibility and haplotype analysis between Fc gamma receptor IIB and IIIA gene with systemic lupus erythematosus in Chinese population," Lupus, 17(8): 733-738 (2008).
Park, et al., "Resistance of Fc Receptor-deficient Mice to Fatal Glomerulonephritis," J Clin Invest 102(6): 1229-1238 (1998).
Peltz, et al., "Cloned and expressed human Fc receptor for IgG mediates anti-CD3-dependent lymphoproliferation," J Immunol, 141(6): 1891-1896 (1988).

(56) References Cited

OTHER PUBLICATIONS

Peltz, et al., "Human Fc gamma RIII: Cloning, expression, and identification of the chromosomal locus of two Fc receptors for IgG," PNAS, 86(3): 1013-1017 (1989).
Perussia, et al., "Murine natural killer cells express functional Fc gamma receptor II encoded by the Fc gamma Ra gene," J Exp Med, 170(1): 73-86 (1989).
Raghavan, et al., "Fc receptors and their interactions with immunoglobulins," Ann Rev Cell Dev Biol, 12(1): 181-220 (1996).
Rappaport, et al., "A soluble form of the human Fc receptor Fc gamma RIIA: cloning, transcript analysis and detection," Exp Hematol, 21(5): 689-696 (1933).
Ravetch, et al., "Alternative membrane forms of Fc gamma RIII (CD16) on human natural killer cells and neutrophils: Cell type-specific expression of two genes that differ in single nucleotide substitutions," J Exp Med, 170(2): 481-497 (1989).
Ravetch, et al., "Fc receptors," Ann Rev Immunol, 9(1): 457-492 (1991).
Ravetch, et al., "IgG Fc Receptors," Ann Rev Immunol, 19(1): 275-290 (2001).
Salmon, et al., "Human Receptors for Immunoglobulin G. Arthritis and Rheumatism," 44(4): 739-750 (2001).
Scallon, et al., "A human immunoglobulin G receptor exists in both polypeptide-anchored and phosphatidylinositol-glycan-anchored forms," PNAS, 86(13): 5079-5083 (1989).
Schmidt, et al., "Fc receptors and their interaction with complement in autoimmunity," Immunol Lett, 100(1): 56-67 (2005).
Selvaraj, et al., "Functional Regulation of Human Neutrophil Fc gamma Receptors," Immunol Res, 29(1-3): 219-229 (2004).
Sequence database: search result for SEQ ID No. 3.
Sibéril, et al., "Fc gamma R: The Key to Optimize Therapeutic Antibodies?" Crit Rev Oncol Hematol, 62(1): 26-33 (2007).
Simmons, et al., "The Fc gamma receptor of natural killer cells is a phospholipid-linked membrane protein," Nature, 333: 568-570 (1988).
Smith, et al. "Mouse model recapitulating human Fc gamma receptor structural and functional diversity," PNAS, 109(16): 6181-6186 (2012).
Sondermann, et al., "Crystal structure of the soluble form of the human Fc gamma-receptor IIb: a new member of the immunoglobulin superfamily at 1.7 a resolution," The EMBO Journal, 18(5): 1095-1103 (1999).
Stuart, et al., "Isolation and expression of cDNA clones encoding a human receptor for IgG (Fc gamma RII)," J Exp Med, 166(6): 1668-1684 (1987).
Su, et al., "Genomic organization of classical human low-affinity Fc gamma receptor genes," Genes Immun, 3(Suppl 1): S51-S56 (2002).
Symons, et al., "Genomic Organisation and Sequence of the Extracellular Domain Exons of the Bovine Fc gamma RI Receptor, and Evidence for Restricted Binding of Ruminant IgG to U937 Cells," Mol Immunol, 29(11): 1407-1413(1992).
Takai, "Fc Receptors and Their Role in Immune Regulation and Autoimmunity," J Clin Immunol, 25(1): 1-18(2005).
Takai, "Roles of Fc Receptors in Autoimmunity," Nat Rev, 2(8): 580-592 (2002).
Takai, et al., "Augmented humoral and anaphylactic responses in Fc gamma RII-deficient mice," Nature, 379: 346-349 (1996).
Takai, et al., "FcR gamma Chain Deletion Results in Pleiotrophic Effector Cell Defects," Cell, 76(3): 519-529 (1994).
Trounstine, et al., "Reactivity of cloned, expressed human Fc gamma RII isoforms with monoclonal antibodies which distinguish cell-type-specific and allelic forms of Fc gamma RII," Int Immunol, 2(4): 303-310 (1990).
Tsuchiya, et al., "Role of Fc gamma receptor IIb polymorphism in the genetic background of systemic lupus eryhematosus: Insights from Asia," Autoimmunity, 38(5): 347-352 (2005).
Tsukahara, et al., "A polymorphism in the gene encoding the Fc gamma IIIA receptor is a possible genetic marker to predict the primary response to infliximab in Japanese patients with rheumatoid arthritis." Ann Rheum Dis, 67(12): 1791-1792 (2008).
Tuijnam, et al., "Human Low-Affinity IgG Receptor Fc gamma RIIa (CD32) Introduced Into Mouse Fibroblasts Mediates Phagocytosis of Sensitized Erythrocytes," Blood, 79(7): 1651-1656(1992).
Van Vugt, et al., "FcR gamma-Chain is Essential for Both Surface Expression and Function of Human Fc gamma RI (CD64) In Vivo," Blood, 87(9): 3593-3599 (1996).
Van De Winkel, et al., "Biological functioning of human IgG Fc receptors," Res Immunol, 141(1): 64-67 (1990).
Van De Winkel, et al., "Biology of Human Immunoglobulin G Fc Receptors," J Leukocyte Biol, 49(5): 511-524 (1991).
Van De Winkel, et al., "Human IgG Fc receptor heterogeneity: molecular aspects and clinical implications," Immunol Today, 14(5): 215-221 (1993).
Van Den Herik-Oudijk, et al., "Functional Differences Between Two Fc Receptor ITAM Signaling Motifs," Blood, 86(9): 3302-3307 (1995).
Verbeek, et al., "The role of FcR in immunity: lessons from gene targeting in mice," Res Immunol, 147(7): 466-474 (1997).
Warmerdam, et al., "A single amino acid in the second Ig-like domain of the human Fc gamma receptor II is critical for human IgG2 binding," J Immunol, 147(4): 1338-1343 (1991).
Warmerdam, et al., "Interaction of a human Fc gamma RIIb1 (CD32) isoform with murine and human IgG subclasses," Int Immunol, 5(3): 239-247 (1993).
Weinshank, et al., "Function and regulation of a murine macrophage-specific IgG Fc receptor, Fc gamma R-a," J Exp Med, 167(6): 1909-1925 (1988).
Written Opinion for International Application No. PCT/US2010/060925 dated Mar. 14, 2011.
Zuniga, et al., "Low-Binding Alleles of Fc gamma Receptor Types IIA and IIIA are Inherited Independently and Are Associated With Systemic Lupus Erythematosus in Hispanic Patients," Arthritis Rheum, 44(2): 361-367 (2001).

* cited by examiner

MAID6074

Figure 6 continued

Junction-1 (mouse to human):
TAACTATAACGGTCCTAAGGTAGCGAAGTGAGTTCCTGTCAGC
(MOUSE) (HUMAN)

Junction-2 (human to loxp (neo cassette removed) to human):
CCGGGCTCGAGATAACTTCGTATAATGTATGCTATACGAAGTTATCCTAGGGCGGATCGCC
(HUMAN) (LOXP) (HUMAN)

Junction-3 (human to mouse):
ACCAACTCCTGTCTCTGGTTTCACATCCTGTGTTTATCTGTCAGTGGGAAT
(HUMAN) (MOUSE)

Relative mRNA expression in whole spleen and blood (normalized to mHPRT1)

SEQUENCE LISTING

```
<160> NUMBER OF SEQ ID NOS: 8

<210> SEQ ID NO 1
<211> LENGTH: 2589
<212> TYPE: DNA
<213> ORGANISM: Mus musculus

<400> SEQUENCE: 1
acattacatg attcttacca gctttggaga tgacatgtgg cttctaacaa ctctgctact      60
ttgggttcca gtcggtgggg aagtggttaa tgccaccaag gctgtgatca ccttgcagcc     120
tccatgggtc agtattttcc agaaggaaaa tgtcactttta tggtgtgagg ggcctcacct    180
gcctggagac agttccacac aatggtttat caacggaaca gccgttcaga tctccacgcc    240
tagttatagc atcccagagg ccagttttca ggacagtggc gaatacaggt gtcagatagg    300
ttcctcaatg ccaagtgacc ctgtgcagtt gcaaatccac aatgattggc tgctactcca    360
ggcctcccgc agagtcctca cagaaggaga accccctggcc ttgaggtgtc acggatggaa   420
gaataaactg tgtgtacaatg tggttttcta tagaaatgga aaatcctttc agttttcttc    480
agattcggag gtcgccattc tgaaaaccaa cctgagtcac agcggcatct accactgctc    540
aggcacggga agacaccgct acacatctgc aggagtgtcc atcacggtga aagagctgtt    600
taccacgcca gtgctgagag catccgtgtc atctcccttc ccggagggga gtctggtcac    660
cctgaactgt gagacgaatt tgctcctgca gagacccggc ttacagcttc acttctcctt    720
ctacgtgggc agcaagatcc tggagtacag gaacacatcc tcagagtacc atatagcaag    780
ggcggaaaga gaagatgctg gattctactg gtgtgaggta gccacggagg acagcagtgt    840
ccttaagcgc agccctgagt tggagctcca agtgcttggt ccccagtcat cagctcctgt    900
ctggtttcac atcctgtttt atctgtcagt gggaataatg ttttcgttga acacggttct    960
ctatgtgaaa atacacaggc tgcagagaga gaagaaatac aacttagaag tccctttggt   1020
ttctgagcag ggaaagaaag caaattcctt tcagcaagtt agaagcgatg gcgtgtatga   1080
```

-continued

```
agaagtaaca gccactgcga gccagaccac accaaaagaa gcgcccgatg gacctcgaag   1140
ctcagtgggt gactgtggac ccgagcagcc tgaacccctt cctcccagtg acagtactgg   1200
ggcacaaact tcccaaagtt gaccctgaaa ctgtgggacc atggcatgca actcttaaat   1260
aaagcaaata tacagactgg atccggctga acaagctggg gtaatcagac atttgaaagg   1320
agacctatac caaagggatc ttgcaacaca tggagtcagg tcacagcggg ggttgtcgaa   1380
tgtttgacct tatggagcag ggaaacagga agtgaatccc acaggactcc ccccccccgc   1440
ccatcccct ccaggccgcc ccggacagga cccagctctg gaagactcca gtctgagact    1500
tgcggaacca gagcagggt gagattcctg cccagaaggg acagctgtgc catcccctca    1560
cagggtggat gggttcaggg aaaggcctcc cagggacgg cctgcgtgtc aggggagcag    1620
acgctgatac agacagctcc atagcctggg ctaaagctgg ctaagacccg gtggtcatcc   1680
tgagagcatc ggaatttgtg ctctccttcc taccgtctct cttcatgcac cctccccaga   1740
tttgctgccc acgaccctca aaggacatag tggcggcagc taaagagtga agtgtcagca   1800
gtaatccatc catctaacct ccctcaggtc cagataccc cacccccaaa ctcccacact    1860
ctaggggcct ttcaggcag cctgcatgtg gtgtcttagc agagctatgg tacaaaggct    1920
tttagctcta tcattatctg acaagcagac agcaccctca ggtgctctca ttgggtggtg   1980
agagcttct ccagcctgta ccacctgtaa gctggagtgt ggggcgggaa cactggccca    2040
aagcgtccct attggaaggc acggcttaca tgggtgtcac aaatgcccct agaccacgca   2100
ggaagaccga attctagaaa caaggagtag atcatgtctc cacttactgt cactcctaag   2160
gatcccctga aggtcttgga gcttcacatc cctggaactc tagggtctgc cgtgctagag   2220
gtcccagtct gcagagtggg tgtggcatag cctgagcctc cctggatgtg aacattagca   2280
aggtatattg ggacctttat aaccagggac caataggcat gagagggacc gggataatgg   2340
accacagtca caggaggaga tacactctgt tgtacaatgc atgcagaaac tgtcaaaaac   2400
agtgtgggag ctggagagat gatcagggt taagaacact tcctgctctt ccagaggacc    2460
tgagttcact ttttgtaact gcttgtaagt ccagatgtcg tcttctgatc tctttcaagc   2520
acccacatgt gcagggcatg cagacacaga catatgaaca gaacaatta aaaataaat    2580
tataactgc                                                          2589
```

<210> SEQ ID NO 2
<211> LENGTH: 404
<212> TYPE: PRT
<213> ORGANISM: Mus musculus

<400> SEQUENCE: 2

```
Met Ile Leu Thr Ser Phe Gly Asp Asp Met Trp Leu Leu Thr Thr Leu
1               5                   10                  15

Leu Leu Trp Val Pro Val Gly Gly Glu Val Val Asn Ala Thr Lys Ala
            20                  25                  30

Val Ile Thr Leu Gln Pro Pro Trp Val Ser Ile Phe Gln Lys Glu Asn
        35                  40                  45

Val Thr Leu Trp Cys Glu Gly Pro His Leu Pro Gly Asp Ser Ser Thr
    50                  55                  60

Gln Trp Phe Ile Asn Gly Thr Ala Val Gln Ile Ser Thr Pro Ser Tyr
65                  70                  75                  80

Ser Ile Pro Glu Ala Ser Phe Gln Asp Ser Gly Glu Tyr Arg Cys Gln
                85                  90                  95
```

-continued

```
Ile Gly Ser Ser Met Pro Ser Asp Pro Val Gln Leu Gln Ile His Asn
            100                 105                 110
Asp Trp Leu Leu Leu Gln Ala Ser Arg Arg Val Leu Thr Glu Gly Glu
        115                 120                 125
Pro Leu Ala Leu Arg Cys His Gly Trp Lys Asn Lys Leu Val Tyr Asn
    130                 135                 140
Val Val Phe Tyr Arg Asn Gly Lys Ser Phe Gln Phe Ser Ser Asp Ser
145                 150                 155                 160
Glu Val Ala Ile Leu Lys Thr Asn Leu Ser His Ser Gly Ile Tyr His
                165                 170                 175
Cys Ser Gly Thr Gly Arg His Arg Tyr Thr Ser Ala Gly Val Ser Ile
            180                 185                 190
Thr Val Lys Glu Leu Phe Thr Thr Pro Val Leu Arg Ala Ser Val Ser
        195                 200                 205
Ser Pro Phe Pro Glu Gly Ser Leu Val Thr Leu Asn Cys Glu Thr Asn
    210                 215                 220
Leu Leu Leu Gln Arg Pro Gly Leu Gln Leu His Phe Ser Phe Tyr Val
225                 230                 235                 240
Gly Ser Lys Ile Leu Glu Tyr Arg Asn Thr Ser Ser Glu Tyr His Ile
                245                 250                 255
Ala Arg Ala Glu Arg Glu Asp Ala Gly Phe Tyr Trp Cys Glu Val Ala
            260                 265                 270
Thr Glu Asp Ser Ser Val Leu Lys Arg Ser Pro Glu Leu Glu Leu Gln
        275                 280                 285
Val Leu Gly Pro Gln Ser Ser Ala Pro Val Trp Phe His Ile Leu Phe
    290                 295                 300
Tyr Leu Ser Val Gly Ile Met Phe Ser Leu Asn Thr Val Leu Tyr Val
305                 310                 315                 320
Lys Ile His Arg Leu Gln Arg Glu Lys Lys Tyr Asn Leu Glu Val Pro
                325                 330                 335
Leu Val Ser Glu Gln Gly Lys Lys Ala Asn Ser Phe Gln Gln Val Arg
            340                 345                 350
Ser Asp Gly Val Tyr Glu Glu Val Thr Ala Thr Ala Ser Gln Thr Thr
        355                 360                 365
Pro Lys Glu Ala Pro Asp Gly Pro Arg Ser Ser Val Gly Asp Cys Gly
    370                 375                 380
Pro Glu Gln Pro Glu Pro Leu Pro Pro Ser Asp Ser Thr Gly Ala Gln
385                 390                 395                 400
Thr Ser Gln Ser

<210> SEQ ID NO 3
<211> LENGTH: 2268
<212> TYPE: DNA
<213> ORGANISM: Homo sapiens

<400> SEQUENCE: 3
aatatcttgc atgttacaga tttcactgct cccaccagct tggagacaac atgtggttct      60
tgacaactct gctcctttgg gttccagttg atgggcaagt ggacaccaca aaggcagtga     120
tcactttgca gcctccatgg gtcagcgtgt tccaagagaa accgtaacc ttgcactgtg      180 aggtgctcca tctgcctggg agcagctcta cacagtggtt tctcaatggc acagccactc     240
agacctcgac cccagctac agaatcacct ctgccagtgt caatgacagt ggtgaataca     300
ggtgccagag aggtctctca gggcgaagtg accccataca gctggaaatc cacagaggct     360
```

```
ggctactact gcaggtctcc agcagagtct tcacggaagg agaacctctg gccttgaggt    420
gtcatgcgtg gaaggataag ctggtgtaca atgtgcttta ctatcgaaat ggcaaagcct    480
ttaagttttt ccactggaat tctaacctca ccattctgaa aaccaacata agtcacaatg    540
gcacctacca ttgctcaggc atgggaaagc atcgctacac atcagcagga atatctgtca    600
ctgtgaaaga gctatttcca gctccagtgc tgaatgcatc tgtgacatcc ccactcctgg    660
aggggaatct ggtcaccctg agctgtgaaa caaagttgct cttgcagagg cctggtttgc    720
agctttactt ctccttctac atgggcagca agaccctgcg aggcaggaac acatcctctg    780
aataccaaat actaactgct agaagagaag actctgggtt atactggtgc gaggctgcca    840
cagaggatgg aaatgtcctt aagcgcagcc ctgagttgga gcttcaagtg cttggcctcc    900
agttaccaac tcctgtctgg tttcatgtcc ttttctatct ggcagtggga ataatgtttt    960
tagtgaacac tgttctctgg gtgacaatac gtaaagaact gaaaagaaag aaaaagtggg   1020
atttagaaat ctcttttggat tctggtcatg agaagaaggt aatttccagc cttcaagaag   1080
acagacattt agaagaagag ctgaaatgtc aggaacaaaa agaagaacag ctgcaggaag   1140
gggtgcaccg gaaggagccc caggggggcca cgtagcagcg gctcagtggg tggccatcga   1200
tctggaccgt cccctgccca cttgctcccc gtgagcactg cgtacaaaca tccaaaagtt   1260
caacaacacc agaactgtgt gtctcatggt atgtaactct taaagcaaat aaatgaactg   1320
acttcaactg ggatacattt ggaaatgtgg tcatcaaaga tgacttgaaa tgaggcctac   1380
tctaaagaat tcttgaaaaa cttacaagtc aagcctagcc tgataatcct attacatagt   1440
ttgaaaaata gtattttatt tctcagaaca aggtaaaaag gtgagtgggt gcatatgtac   1500
agaagattaa gacagagaaa cagacagaaa gagacacaca cacagccagg agtgggtaga   1560
tttcagggag acaagaggga atagtataga caataaggaa ggaaatagta cttacaaatg   1620
actcctaagg gactgtgaga ctgagagggc tcacgcctct gtgttcagga tacttagttc   1680
atggcttttc tctttgactt tactaaaaga gaatgtctcc atacgcgttc taggcataca   1740 aggggggtaac tcatgatgag aaatggatgt gttattcttg ccctctcttt tgaggctctc   1800
tcataacccc tctatttcta gagacaacaa aaatgctgcc agtcctaggc ccctgccctg   1860
taggaaggca gaatgtaact gttctgtttg tttaacgatt aagtccaaat ctccaagtgc   1920
ggcactgcaa agagacgctt caagtgggga gaagcggcga taccatagag tccagatctt   1980
gcctccagag atttgcttta ccttcctgat tttctggtta ctaattagct tcaggatacg   2040
ctgctctcat acttgggctg tagttttggag acaaaatatt ttcctgccac tgtgtaacat   2100
agctgaggta aaaactgaac tatgtaaatg actctactaa aagtttaggg aaaaaaaaca   2160
ggaggagtat gacacaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaa             2268
```

<210> SEQ ID NO 4
<211> LENGTH: 374
<212> TYPE: PRT
<213> ORGANISM: Homo sapiens

<400> SEQUENCE: 4

```
Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
```

```
                  35                  40                  45
Pro Gly Ser Ser Ser Thr Gln Trp Phe Leu Asn Gly Thr Ala Thr Gln
 50                  55                  60

Thr Ser Thr Pro Ser Tyr Arg Ile Thr Ser Ala Ser Val Asn Asp Ser
 65                  70                  75                  80

Gly Glu Tyr Arg Cys Gln Arg Gly Leu Ser Gly Arg Ser Asp Pro Ile
                     85                  90                  95

Gln Leu Glu Ile His Arg Gly Trp Leu Leu Gln Val Ser Ser Arg
                100                 105                 110

Val Phe Thr Glu Gly Glu Pro Leu Ala Leu Arg Cys His Ala Trp Lys
                115                 120                 125

Asp Lys Leu Val Tyr Asn Val Leu Tyr Tyr Arg Asn Gly Lys Ala Phe
                130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                    165                 170                 175

Thr Ser Ala Gly Ile Ser Val Thr Val Lys Glu Leu Phe Pro Ala Pro
                180                 185                 190

Val Leu Asn Ala Ser Val Thr Ser Pro Leu Leu Glu Gly Asn Leu Val
                195                 200                 205

Thr Leu Ser Cys Glu Thr Lys Leu Leu Leu Gln Arg Pro Gly Leu Gln
                210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                    245                 250                 255

Leu Tyr Trp Cys Glu Ala Ala Thr Glu Asp Gly Asn Val Leu Lys Arg
                260                 265                 270

Ser Pro Glu Leu Glu Leu Gln Val Leu Gly Leu Gln Leu Pro Thr Pro
                275                 280                 285

Val Trp Phe His Val Leu Phe Tyr Leu Ala Val Gly Ile Met Phe Leu
                290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                    325                 330                 335

Val Ile Ser Ser Leu Gln Glu Asp Arg His Leu Glu Glu Glu Leu Lys
                340                 345                 350

Cys Gln Glu Gln Lys Glu Glu Gln Leu Gln Glu Gly Val His Arg Lys
                355                 360                 365

Glu Pro Gln Gly Ala Thr
        370

<210> SEQ ID NO 5
<211> LENGTH: 404
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Trp Phe Leu Thr Thr Leu Leu Leu Trp Val Pro Val Asp Gly Gln
  1               5                  10                  15
```

Val Asp Thr Thr Lys Ala Val Ile Thr Leu Gln Pro Pro Trp Val Ser
         20                  25                  30

Val Phe Gln Glu Glu Thr Val Thr Leu His Cys Glu Val Leu His Leu
             35                  40                  45

Pro Gly Ser Ser Ser Thr Gln Trp Phe Leu Asn Gly Thr Ala Thr Gln
         50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                 85                  90                  95

Gln Leu Glu Ile His Arg Gly Trp Leu Leu Leu Gln Val Ser Ser Arg
             100                 105                 110

Val Phe Thr Glu Gly Glu Pro Leu Ala Leu Arg Cys His Ala Trp Lys
         115                 120                 125

Asp Lys Leu Val Tyr Asn Val Leu Tyr Tyr Arg Asn Gly Lys Ala Phe
     130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                 165                 170                 175

Thr Ser Ala Gly Ile Ser Val Thr Val Lys Glu Leu Phe Pro Ala Pro
             180                 185                 190

Val Leu Asn Ala Ser Val Thr Ser Pro Leu Leu Glu Gly Asn Leu Val
         195                 200                 205

Thr Leu Ser Cys Glu Thr Lys Leu Leu Leu Gln Arg Pro Gly Leu Gln
     210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                 245                 250                 255

Leu Tyr Trp Cys Glu Ala Ala Thr Glu Asp Gly Asn Val Leu Lys Arg
             260                 265                 270

Ser Pro Glu Leu Glu Leu Gln Val Leu Gly Leu Gln Leu Pro Thr Pro
         275                 280                 285

Val Trp Gly Pro Gln Ser Ser Ala Pro Val Trp Phe His Ile Leu Phe
     290                 295                 300

Tyr Leu Ser Val Gly Ile Met Phe Ser Leu Asn Thr Val Leu Tyr Val
305                 310                 315                 320

Lys Ile His Arg Leu Gln Arg Glu Lys Lys Tyr Asn Leu Glu Val Pro
                 325                 330                 335

Leu Val Ser Glu Gln Gly Lys Lys Ala Asn Ser Phe Gln Gln Val Arg
             340                 345                 350

Ser Asp Gly Val Tyr Glu Glu Val Thr Ala Thr Ala Ser Gln Thr Thr
         355                 360                 365

Pro Lys Glu Ala Pro Asp Gly Pro Arg Ser Ser Val Gly Asp Cys Gly
     370                 375                 380

Pro Glu Gln Pro Glu Pro Leu Pro Pro Ser Asp Ser Thr Gly Ala Gln
385                 390                 395                 400

Thr Ser Gln Ser

<210> SEQ ID NO 6
<211> LENGTH: 44
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 6
taactataac ggtcctaagg tagcgaagtg agttccctgt cagc                    44

<210> SEQ ID NO 7
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccgggctcga gataacttcg tataatgtat gctatacgaa gttatcctag ggcgatcgcc   60
c                                                                   61

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
accaactcct gtctggtttc acatcctgtt ttatctgtca gtgggaat               48
```

NON-HUMAN ANIMALS HAVING HUMANIZED FC-GAMMA RECEPTORS

RELATED APPLICATIONS

This application is a Continuation of application Ser. No. 14/681,617, filed Apr. 8, 2015, which claims the benefit of priority to Provisional Application No. 61/977,037, filed Apr. 8, 2014, each of which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on May 26, 2015, is named RPB-008.02_SL.txt and is 20,480 bytes in size.

BACKGROUND

Fc receptors (FcRs) are proteins found on the surface of cells of the immune system that carry out a variety of functions of the immune system in mammals. FcRs exist in a variety of types, on a variety of cells, and mediate a variety of immune functions such as, for example, binding to antibodies that are attached to infected cells or invading pathogens, stimulating phagocytic or cytotoxic cells to destroy microbes, or infected cells by antibody-mediated phagocytosis or antibody-dependent cell-mediated cytotoxicity (ADCC).

ADCC is a process whereby effector cells of the immune system lyse a target cell bound by antibodies. This process depends on prior exposure to a foreign antigen or cell, resulting in an antibody response. ADCC can be mediated through effector cells such as, for example, natural killer (NK) cells, by binding of FcR expressed on the surface of the effector cell to the Fc portion of the antibody which itself is bound to the foreign antigen or cell. High affinity FcγR1 receptor signaling plays an important role in immune system regulation and effector cell function.

SUMMARY OF INVENTION

The present invention encompasses the recognition that it is desirable to engineer non-human animals, such as mice, to express a human or hybrid FcγRI protein to permit experimentation on human immune effector responses that could not be performed in humans.

The present invention also encompasses the recognition that it is desirable to replace the endogenous mouse FcγRI gene with a humanized (human or hybrid) FcγRI gene.

In some embodiments, the invention provides a mouse that expresses a FcγRI protein comprising the extracellular portion of a human FcγRIα chain and the intracellular portion of a mouse FcγRIα chain. In some embodiments, an extracellular portion of a human FcγRIα chain comprises an EC1 domain, EC2 domain, EC3 domain, or combinations thereof.

In some embodiments, the EC1 domain is encoded by an exon at least 50%, 70%, 85%, 90% or 95% identical to exon 3 of SEQ ID NO: 3.

In some embodiments, the EC2 domain is encoded by an exon at least 50%, 70%, 85%, 90%, or 95% identical to exon 4 of SEQ ID NO: 3

In some embodiments, the EC3 domain is encoded by an exon at least 50%, 70%, 85%, 90%, or 95% identical to exon 5 of SEQ ID NO: 3.

In some embodiments, the invention provides a mouse that expresses a FcγRI protein comprising the extracellular portion of a human FcγRIα chain and the intracellular portion of a mouse FcγRIα chain wherein the mouse does not detectably express a full-length mouse FcγRIα chain. In some embodiments, the intracellular portion of a FcγRIα chain comprises a cytoplasmic domain of a mouse FcγRIα chain in whole or in part. In some embodiments, a mouse further expresses a FcγRIα chain comprising a mouse FcγRIα chain transmembrane domain in whole or in part.

In some embodiments, the invention provides a mouse that expresses an FcγRIα chain amino acid sequence at least 70%, 85%, 90%, or 95% identical to SEQ ID NO: 5. In some embodiments, human or hybrid FcγRI protein is detectably expressed on monocytes, macrophages, neutrophils, dendritic cells, and/or combinations thereof.

In some embodiments, human FcγRI protein level is increased by administration of murine granulocyte colony stimulating factor (mG-CSF). In some embodiments, mouse FcγRI protein level is not increased in monocytes, neutrophils, or dendritic cells by administration of murine granulocyte colony stimulating factor (mG-CSF).

In some embodiments, the invention provides a mouse that expresses an FcγRI gene that comprises one or more exons of a human FcγRI gene operably linked to one or more exons of a mouse FcγRI gene. In some embodiments, exons of a human FcγRI gene encode one or more extracellular portions of human FcγRI protein. In some embodiments, exons of a mouse FcγRI gene encode one or more intracellular portions of a mouse FcγRI protein. In some embodiments, exons of a human FcγRI are selected from the group consisting of exons 3, 4, 5, and combinations thereof.

In some embodiments, an intracellular portion of a mouse FcγRI is operably linked to one or more mouse intracellular signaling cascades.

In some embodiments, the invention provides a mouse that expresses a human FcγRI, wherein germ line cells of the mouse lack a functional mouse FcγRI gene. In some embodiment the invention provides a mouse that expresses a human FcγRI, wherein germ line cells of the mouse lack any mouse FcγRI gene.

In some embodiments, the invention provides an embryonic stem cell whose genome comprises a FcγRI gene that encodes the extracellular portion of a human FcγRI protein and the intracellular portion of a mouse FcγRI protein. In some embodiments, an FcγRI gene comprises exons 3, 4, and 5 of a human FcγRI gene. In some embodiments, an FcγRI gene further comprises one or more human 5' untranslated regions flanking human exon 1. In some embodiments, an extracellular portion of a human FcγRI protein comprises one or more of EC1, EC2, and EC3.

In some embodiments, the invention provides an embryonic stem cell whose genome comprises an FcγRI α chain amino acid sequence at least 70%, 85%, 90%, or 95% identical to SEQ ID NO: 5.

In some embodiments, an embryonic stem cell comprises an FcγRI gene comprising amino acid residues of exon 6 of a mouse FcγRI gene. In some embodiments, an intracellular portion of a mouse FcγRI protein comprises the cytoplasmic domain of a mouse FcγRI protein in whole or in part.

In some embodiments, the invention provides an embryonic stem cell comprising a human FcγRI gene wherein the human FcγRI gene is positioned at an endogenous FcγRI locus that appears in a mouse genome as found in nature.

In some embodiments, the invention provides a mouse embryo generated from an embryonic stem as described herein.

In some embodiments, the invention provides for use of a mouse embryonic stem cell as described herein to make a transgenic mouse.

In some embodiments, methods of making a mouse that expresses FcγRI protein comprising an extracellular portion of a human FcγRI protein and an intracellular portion of a mouse FcγRI protein are disclosed, the method comprising steps of: (a) obtaining a mouse embryonic stem cell; (b) replacing in the embryonic cell an endogenous mouse FcγRI gene with a genomic fragment comprising a nucleic acid molecule that encodes a portion of human FcγRI protein having human extracellular regions; and (c) creating the mouse using the embryonic cell of (b).

In some embodiments, the invention provides a genomic fragment comprising a nucleic acid molecule that encodes a portion of human FcγRI protein having human extracellular regions and a nucleic acid molecule that encodes an intracellular portion of a mouse FcγRI protein.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings included herein are for illustration purposes only not for limitation.

DEFINITIONS

Figure 1:
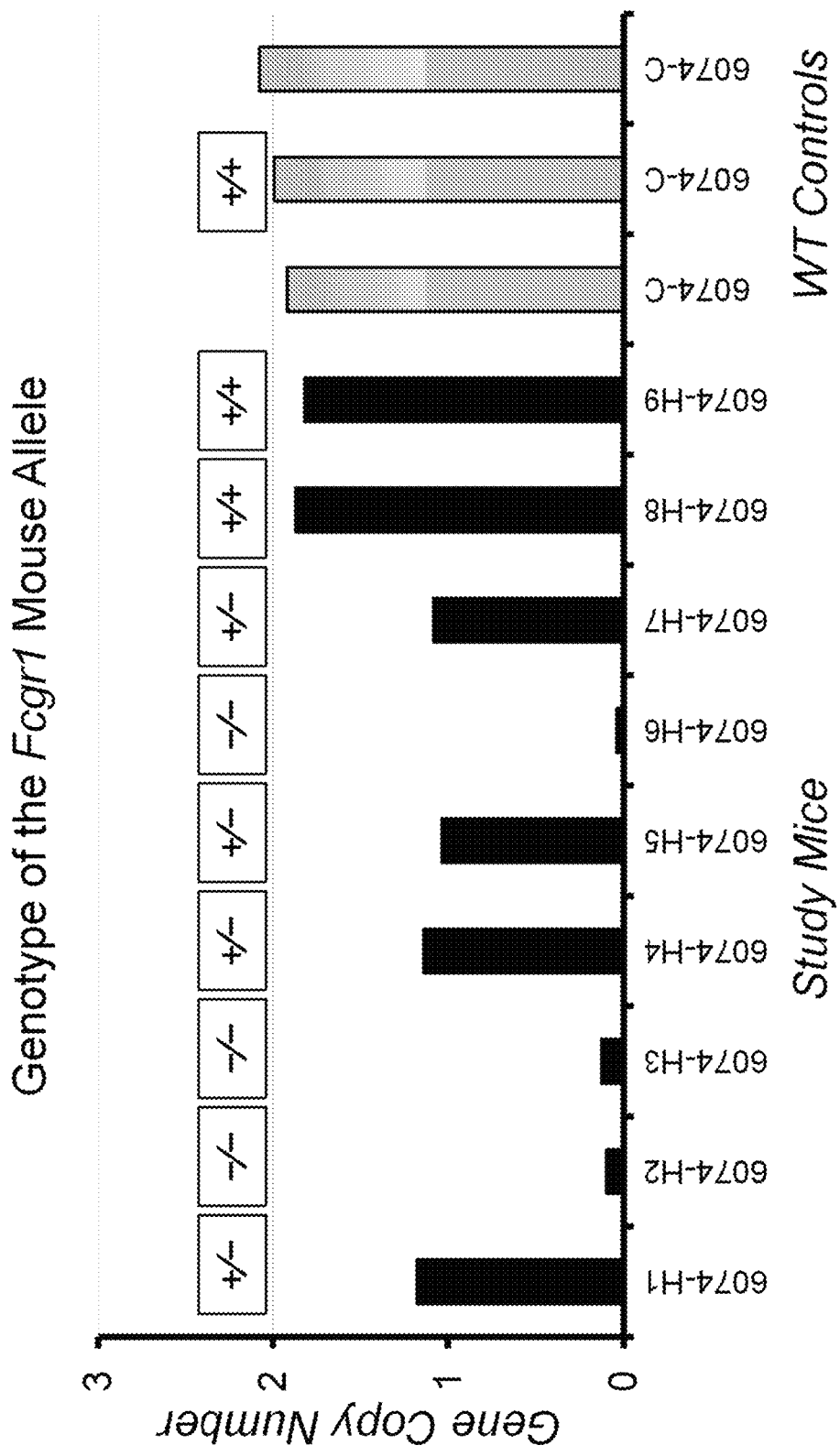
FIG. 1 shows genotyping of the FcγRI mouse allele in experimental mice and wild-type controls.

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described.

The term "approximately" as applied herein to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "biologically active" as used herein refers to a characteristic of any agent that has activity in a biological system, in vitro or in vivo (e.g., in an organism). For instance, an agent that, when present in an organism, has a biological effect within that organism, is considered to be biologically active. In particular embodiments, where a protein or polypeptide is biologically active, a portion of that protein or polypeptide that shares at least one biological activity of the protein or polypeptide is typically referred to as a "biologically active" portion.

The term "comparable" as used herein refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

The term "conservative" is used herein to describe a conservative amino acid substitution refers to substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be substitution of any native residue in a protein with alanine, as used in, for example, alanine scanning mutagenesis. In some embodiments, a conservative substitution is made that has a positive value in the PAM250 log-likelihood matrix disclosed in Gonnet et al. (1992) Exhaustive Matching of the Entire Protein Sequence Database, Science 256:1443-45, hereby incorporated by reference. In some embodiments, the substitution is a moderately conservative substitution wherein the substitution has a nonnegative value in the PAM250 log-likelihood matrix.

The term "disruption" as used herein refers to the result of a homologous recombination event with a DNA molecule (e.g., with an endogenous homologous sequence such as a gene or gene locus. In some embodiments, a disruption may achieve or represent an insertion, deletion, substitution, replacement, missense mutation, or a frame-shift of a DNA sequence(s), or any combination thereof. Insertions may include the insertion of entire genes or fragments of genes, e.g. exons, which may be of an origin other than the endogenous sequence. In some embodiments, a disruption may increase expression and/or activity of a gene or gene product (e.g., of a protein encoded by a gene). In some embodiments, a disruption may decrease expression and/or activity of a gene or gene product. In some embodiments, a disruption may alter sequence of a gene or an encoded gene product (e.g., an encoded protein). In some embodiments, a disruption may truncate or fragment a gene or an encoded gene product (e.g., an encoded protein). In some embodiments, a disruption may extend a gene or an encoded gene product; in some such embodiments, a disruption may achieve assembly of a fusion protein. In some embodiments, a disruption may affect level but not activity of a gene or gene product. In some embodiments, a disruption may affect activity but not level of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

The phrase "endogenous locus" or "endogenous gene" as used herein refers to a genetic locus found in a parent or reference organism prior to introduction of a disruption, deletion, replacement, alteration, or modification as described herein. In some embodiments, the endogenous locus has a sequence found in nature. In some embodiments, the endogenous locus is wild type. In some embodiments, the reference organism is a wild-type organism. In some embodiments, the reference organism is an engineered organism. In some embodiments, the reference organism is a laboratory-bred organism (whether wild-type or engineered).

The phrase "endogenous promoter" as used herein refers to a promoter that is naturally associated, e.g., in a wild-type organism, with an endogenous gene.

The term "FcγRI protein" as used herein refers to a high affinity immunoglobulin Fc receptor comprising an α chain having three extracellular domains, a transmembrane domain, and an intracellular domain.

By way of illustration, representative nucleotide and amino acid sequences of a mouse and human FcγRIα genes are provided in Table 3. Persons of skill upon reading this disclosure will recognize that one or more endogenous FcγRI receptor genes in a genome (or all) can be replaced by one or more heterologous FcγRI genes (e.g., polymorphic variants, subtypes or mutants, genes from another species, etc.).

A "FcγRI-expressing cell" as used herein refers to a cell that expresses FcγRI. In some embodiments, an FcγRI-expressing cell expresses a FcγRI receptor on its surface. In some embodiments, a FcγRI receptor is expressed on the surface of the cell in an amount sufficient to mediate cell-to-cell interactions via the FcγRI protein expressed on the surface of the cell. Exemplary FcγRI-expressing cells include, lymphocytes, myeloid cells, macrophages, neutrophils, and natural killer (NK) cells. FcγRI-expressing cells regulate the interaction of immune cells to regulate the immune response to various foreign antigens or pathogens. In some embodiments, non-human animals of the present invention demonstrate immune cell regulation via humanized FcγRI receptors expressed on the surface of one more cells of the non-human animal.

The term "heterologous" as used herein refers to an agent or entity from a different source. For example, when used in reference to a polypeptide, gene, or gene product or present in a particular cell or organism, the term clarifies that the relevant polypeptide, gene, or gene product 1) was engineered by the hand of man; 2) was introduced into the cell or organism (or a precursor thereof) through the hand of man (e.g., via genetic engineering); and/or 3) is not naturally produced by or present in the relevant cell or organism (e.g., the relevant cell type or organism type).

The term "host cell" as used herein refers to a cell into which a heterologous (e.g., exogenous) nucleic acid or protein has been introduced. Persons of skill upon reading this disclosure will understand that such terms refer not only to the particular subject cell, but also is used to refer to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, a host cell is or comprises a prokaryotic or eukaryotic cell. In general, a host cell is any cell that is suitable for receiving and/or producing a heterologous nucleic acid or protein, regardless of the Kingdom of life to which the cell is designated. Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell). In some embodiments, a host cell is or comprises an isolated cell. In some embodiments, a host cell is part of a tissue. In some embodiments, a host cell is part of an organism.

The phrase "human FcγRI gene" as used herein refers to a nucleotide sequence encoding a fully human, substantially human, or humanized portion of an FcγRI protein depending on context. In some embodiments, a "human FcγRI" gene refers to a humanized FcγRI gene as contrasted with a fully mouse FcγRI gene. In some embodiments, a human FcγRI gene contains one or more substitutions, additions, deletions, or mutations. In some embodiments a human FcγRI gene comprises FcγRIA (CD64A), FcγRIB (CD64B), FcγRIC (CD64C), or combinations thereof.

The phrase "human FcγRI protein" refers to a protein encoded by a fully human, substantially human, or humanized FcγRI gene depending on context. In some embodiments, a "human FcγRI" protein refers to a humanized FcγRI protein as contrasted with a fully mouse FcγRI protein. In some embodiments, a human FcγRI protein comprises one or more amino acid substitutions, additions, deletions, or mutations. In some embodiments, a FcγRI protein comprises FcγRIA (CD64A), FcγRIB (CD64B), FcγRIC (CD64C), or combinations thereof.

The phrase "hybrid FcγRI gene" or "hybrid FcγRI protein" refers to a FcγRI gene or protein that includes an FcγRI sequence of at least two different species of animals. In some embodiments, a hybrid FcγRI gene includes a portion of a human nucleic acid sequence and a portion of a mouse nucleic acid sequence. In some embodiments, a hybrid FcγRI protein includes a portion of human amino acid sequence and a portion of a mouse amino acid sequence.

The term "humanized", is used herein in accordance with its art-understood meaning to refer to nucleic acids or proteins whose structures (i.e., nucleotide or amino acid sequences) include portions that correspond substantially or identically with structures of a particular gene or protein found in nature in a non-human animal, and also include portions that differ from that found in the relevant particular non-human gene or protein and instead correspond more closely with comparable structures found in a corresponding human gene or protein. In some embodiments, a "humanized" gene is one that encodes a polypeptide having substantially the amino acid sequence as that of a human polypeptide (e.g., a human protein or portion thereof—e.g., characteristic portion thereof). To give but one example, in the case of a membrane receptor, a "humanized" gene may encode a polypeptide having an extracellular portion having an amino acid sequence as that of a human extracellular portion and the remaining sequence as that of a non-human (e.g., mouse) polypeptide. In some embodiments, a humanized gene comprises at least a portion of an DNA sequence of a human gene. In some embodiment, a humanized gene comprises an entire DNA sequence of a human gene. In some embodiments, a humanized protein comprises a sequence having a portion that appears in a human protein. In some embodiments, a humanized protein comprises an entire sequence of a human protein and is expressed from an endogenous locus of a non-human animal that corresponds to the homolog or ortholog of the human gene.

The term "identity" as used herein in connection with a comparison of sequences, refers to identity as determined by a number of different algorithms known in the art that can be used to measure nucleotide and/or amino acid sequence identity. In some embodiments, identities as described herein are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008).

The terms "intracellular signal cascade" or "intracellular signal transduction" as used herein refers to a transmission of signal from a cell surface to one or more intracellular targets. In some embodiments, intracellular signal transduction comprises a physiological response in a cell that is elicited by the binding of a target molecule (e.g., an immunoglobulin Fc region) to an extracellular component of a FcγR1 receptor.

The term "isolated" as used herein refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 9'7%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

The phrase "mouse FcγRI gene" as used herein refers to a gene comprising a nucleic molecule as shown in SEQ ID NO: 1, or a nucleic acid molecule having substantial identity to a molecule as shown in SEQ ID NO: 1.

The phrase "mouse FcγRI protein" as used herein refers to a protein comprising an amino acid sequence as shown in SEQ ID NO: 2, including a protein having substantial identity to a protein as shown in SEQ ID NO: 2.

The phrase "non-human animal" as used herein refers to any vertebrate organism that is not a human. In some embodiments, a non-human animal is a cyclostome, a bony fish, a cartilaginous fish (e.g., a shark or a ray), an amphibian, a reptile, a mammal, and a bird. In some embodiments, a non-human mammal is a primate, a goat, a sheep, a pig, a dog, a cow, or a rodent. In some embodiments, a non-human animal is a rodent such as a rat or a mouse.

The phrase "nucleic acid" as used herein in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

The phrase "operably linked" as used herein refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

The term "polypeptide" as used herein refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man.

The term "recombinant" as used herein is intended to refer to polypeptides (e.g., signal-regulatory proteins as described herein) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. For example, in some embodiments, a recombinant polypeptide is comprised of sequences found in the genome of a source organism of interest (e.g., human, mouse, etc.). In some embodiments, a recombinant polypeptide has an amino acid sequence that resulted from mutagenesis (e.g., in vitro or in vivo, for example in a non-human animal), so that the amino acid sequences of the recombinant polypeptides are sequences that, while originating from and related to polypeptides sequences, may not naturally exist within the genome of a non-human animal in vivo.

The term "replacement" is used herein to refer to a process through which a "replaced" nucleic acid sequence (e.g., a gene) found in a host locus (e.g., in a genome) is removed from that locus and a different, "replacement" nucleic acid is located in its place. In some embodiments, the replaced nucleic acid sequence and the replacement nucleic acid sequences are comparable to one another in that, for example, they are homologous to one another and/or contain corresponding elements (e.g., protein-coding elements, regulatory elements, etc.). In some embodiments, a replaced nucleic acid sequence includes one or more of a promoter, an enhancer, a splice donor site, a splice receiver site, an intron, an exon, an untranslated region (UTR); in some embodiments, a replacement nucleic acid sequence includes one or more coding sequences. In some embodiments, a replacement nucleic acid sequence is a homolog of the replaced nucleic acid sequence. In some embodiments, a replacement nucleic acid sequence is an ortholog of the replaced sequence. In some embodiments, a replacement nucleic acid sequence is or comprises a human nucleic acid sequence. In some embodiments, including where the replacement nucleic acid sequence is or comprises a human nucleic acid sequence, the replaced nucleic acid sequence is or comprises a rodent sequence (e.g., a mouse sequence). The nucleic acid sequence so placed may include one or more regulatory sequences that are part of source nucleic acid sequence used to obtain the sequence so placed (e.g., promoters, enhancers, 5'- or 3'-untranslated regions, etc.). For example, in various embodiments, the replacement is a substitution of an endogenous sequence with a heterologous sequence that results in the production of a gene product from the nucleic acid sequence so placed (comprising the heterologous sequence), but not expression of the endogenous sequence; the replacement is of an endogenous genomic sequence with a nucleic acid sequence that encodes a protein that has a similar function as a protein encoded by the endogenous sequence (e.g., the endogenous genomic sequence encodes a FcγRI protein, and the DNA fragment encodes one or more human FcγRI proteins). In various embodiments, an endogenous gene or fragment thereof is replaced with a corresponding human gene or fragment thereof. A corresponding human gene or fragment thereof is a human gene or fragment that is an ortholog of, or is substantially similar or the same in structure and/or function, as the endogenous gene or fragment thereof that is replaced.

The term "substantially" as used herein refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The phrase "substantial homology" as used herein refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized in Table 1 and 2.

TABLE 1

| Alanine | Ala | A | nonpolar | neutral | 1.8 |
|---|---|---|---|---|---|
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

TABLE 2

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 9, 10, 11, 12, 13, 14, 15, 16, 17 or more residues. In some embodiments, the relevant stretch includes contiguous residues along a complete sequence. In some embodiments, the relevant stretch includes discontinuous residues along a complete sequence. In some embodiments, the relevant stretch is at least 10, 15, 20, 25, 30, 35, 40, 45, 50, or more residues.

The phrase "substantial identity" as used herein refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, or more residues.

The phrase "targeting vector" or "targeting construct" as used herein refers to a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., loxP or Frt sites) are also included. In some embodiments, a targeting construct of the present invention further comprises a nucleic acid sequence or gene of particular interest, a selectable marker, control and or regulatory sequences, and other nucleic acid sequences that allow for recombination mediated through exogenous addition of proteins that aid in or facilitate recombination involving such sequences. In some embodiments, a targeting construct of the present invention further comprises a gene of interest in whole or in part, wherein the gene of interest is a heterologous gene that encodes a protein in whole or in part that has a similar function as a protein encoded by an endogenous sequence.

The term "variant" as used herein refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs double, E vs Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

The term "vector" as used herein refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

The term "wild-type" as used herein has its art-understood meaning that refers to an entity having a structure and/or activity as found in nature in a "normal" (as contrasted with mutant, diseased, altered, etc.) state or context. Those of ordinary skill in the art will appreciate that wild type genes and polypeptides often exist in multiple different forms (e.g., alleles).

Various aspects of the invention are described in detail in the following sections. The use of sections is not meant to limit the invention. Each section can apply to any aspect of the invention. In this application, the use of "or" means "and/or" unless stated otherwise.

DETAILED DESCRIPTION

The present invention provides, among other things, improved and/or engineered non-human animals having humanized genetic material encoding an FcγRI receptor for experimentation on human or human-like immune effector responses.

Fc Receptors

The receptors for the Fc (i.e., constant) regions of immunoglobulins (FcRs) play an important role in the regulation of the immune response. FcRs are present on accessory cells of a host immune system to facilitate disposal of foreign antigens bound by an antibody. FcRs also play important roles in balancing both activating and inhibitory responses of the accessory cells of the immune system. FcRs are involved in phagocytosis by macrophages, degranulation of mast cells, uptake of antibody-antigen complexes and modulation of the immune response, as well as other immune system processes.

In mice and humans, distinct FcRs are differentially expressed on the surface of different accessory cells that are each specific for the immunoglobulin isotypes present in the expressed antibody repertoire. For example, immunoglobulin G (IgG) antibodies mediate effector functions through IgG receptors (FcγRs). FcγRs have been classified into four groups: high affinity activating FcγRI (CD64), low affinity inhibitory FcγRIIb (CD32b), low affinity activating FcgRIIa/c (CD32a/c) and low affinity activating FcγRIII (CD16). Although each group is present in both mice and humans, the number of isoforms and subsets of immune cells on which they are present are different. For example, Fcγ RIIA and FcγRIIIB are expressed on accessory cells in humans but are reportedly absent from mice. Further, affinities of the different IgG isotypes (e.g., IgG 1) for each FcγR is different between mice and humans.

High Affinity Human FcγRI

The human high affinity FcγRI (CD64) is an integral membrane glycoprotein that binds monomeric IgG-type antibodies with high affinity (typically with Ka approximately $10^{-8}$ to $10^{-9}$ M). After binding IgG, CD64 interacts with an accessory chain known as the common γ chain (γ chain), which possesses an immunoreceptor tyrosine-based activation motif (ITAM) that triggers cellular activation. In humans, CD64 has been reported to be constitutively expressed on macrophages and monocytes, with inducible expression on polymorphonuclear leukocytes by cytokines such as IFNγ and G-CSF.

FcγRI Sequences

Exemplary sequences for human, mouse, and hybridized FcγRI are set forth in Table 3. For cDNA sequences, consecutive exons are separated by alternating underlined text. For protein sequences, extracellular sequences are underlined. The referenced sequences are exemplary; those skilled in the art are able to determine and compare sequence elements or degrees of identity in order to discriminate additional mouse and human sequences.

TABLE 3

| | |
|---|---|
| Mouse FcγRI cDNA NM_010186 | ACATTACATG ATTCTTACCA GCTTTGGAGA TGACATGTGG CTTCTAACAA CTCTGCTACT TTGGGTTCCA GTCGGTGGGG AAGTGGTTAA TGCCACCAAG GCTGTGATCA CCTTGCAGCC TCCATGGGTC AGTATTTTCC AGAAGGAAAA TGTCACTTTA TGGTGTGAGG GGCCTCACCT GCCTGGAGAC AGTTCCACAC AATGGTTTAT CAACGGAACA GCCGTTCAGA TCTCCACGCC TAGTTATAGC ATCCCAGAGG CCAGTTTTCA GGACAGTGGC GAATACAGGT GTCAGATAGG TTCCTCAATG CCAAGTGACC CTGTGCAGTT GCAAATCCAC AATGATTGGC TGCTACTCCA GGCCTCCCGC AGAGTCCTCA CAGAAGGAGA ACCCCTGGCC TTGAGGTGTC ACGGATGGAA GAATAAACTG GTGTACAATG TGGTTTTCTA TAGAAATGGA AAATCCTTTC AGTTTTCTTC AGATTCGGAG GTCGCCATTC TGAAAACCAA CCTGAGTCAC AGCGGCATCT ACCACTGCTC AGGCACGGGA AGACACCGCT ACACATCTGC AGGAGTGTCC ATCACGGTGA AAGAGCTGTT TACCACGCCA GTGCTGAGAG CATCCGTGTC ATCTCCCTTC CCGGAGGGGA GTCTGGTCAC CCTGAACTGT GAGACGAATT TGCTCCTGCA GAGACCCGGC TTACAGCTTC ACTTCTCCTT CTACGTGGGC AGCAAGATCC TGGAGTACAG GAACACATCC TCAGAGTACC ATATAGCAAG GGCGGAAAGA GAAGATGCTG GATTCTACTG GTGTGAGGTA GCCACGGAGG ACAGCAGTGT CCTTAAGCGC AGCCCTGAGT GGAGCTCCA AGTGCTTGGT CCCCAGTCAT CAGCTCCTGT CTGGTTTCAC ATCCTGTTTT ATCTGTCAGT GGGAATAATG TTTTCGTTGA ACACGGTTCT CTATGTGAAA ATACACAGGC TGCAGAGAGA GAAGAAATAC AACTTAGAAG TCCCTTTGGT TTCTGAGCAG GGAAAGAAAG CAAATTCCTT TCAGCAAGTT GAAGCGATG GCGTGTATGA AGAAGTAACA GCCACTGCGA GCCAGACCAC ACCAAAAGAA GCGCCCGATG GACCTCGAAG CTCAGTGGGT GACTGTGGAC CCGAGCAGCC TGAACCCCTT CCTCCCAGTG ACAGTACTGG GGCACAAACT TCCCAAAGTT GACCCTGAAA CTGTGGGACC ATGGCATGCA ACTCTTAAAT AAAGCAAATA TACAGACTGG ATCCGGCTGA GACAAGCTGG GTAATCAGAC ATTTGAAAGG AGACCTATAC CAAAGGGATC TTGCAACACA TGGAGTCAGG TCACAGCGGG GGTTGTCAA TGTTTGACCT TATGGAGCAG GGAAACAGGA AGTGAATCCC ACAGGACTCC CCCCCCCGC CCATCCCCCT CCAGGCCGCC CCGGACAGGA CCCAGCTCTG GAAGACTCCA GTCTGAGACT TGCGGAACCA GAGCAGGGGT GAGATTCCTG CCCAGAAGGG ACAGCTGTGC CATCCCCTCA CAGGGTGGAT GGGTTCAGGG AAAGGCCTCC CCAGGGACGG CCTGCGTGTC AGGGGAGCAG ACGCTGATAC AGACAGCTCC ATAGCCTGGG CTAAAGCTGG CTAAGACCCG GTGGTCATCC TGAGAGCATC GGAATTTGTG CTCTCCTTCC TACCGTCTCT CTTCATGCAC CCTCCCCAGA TTTGCTGCCC ACGACCCTCA AAGGACATAG TGGCGGCAGC TAAAGAGTGA AGTGTCAGCA GTAATCCATC CATCTAACCT CCCTCAGGTC CAGATACCCC CACCCCCAAA CTCCCACACT CTAGGGGCCT TTTCAGGCAG CCTGCATGTG GTGTCTTAGC AGAGCTATGG TACAAAGGCT TTTAGCTCTA TCATTATCTG ACAAGCAGAC AGCACCCTCA GGTGCTCTCA TTGGGTGGTG AGAGCTTTCT CCAGCCTGTA CCACCTGTAA GCTGGAGTGT GGGGCGGGAA CACTGGCCCA AAGCGTCCCT ATTGGAAGGC ACGGCTTACA TGGGTGTCAC AAATGCCCTT AGACCACGCA GGAAGACCGA ATTCTAGAAA CAAGGAGTAG ATCATGTCTC CACTTACTGT CACTCCTAAG GATCCCCTGA AGGTCTTGGA GCTTCACATC CCTGGAACTC TAGGGTCTGC CGTGCTAGAG GTCCCAGTCT GCAGAGTGGG TGTGGCATAG CCTGAGCCTC CCTGGATGTG AACATTAGCA AGGTATATTG GGACCTTTAT AACCAGGGAC CAATAGGCAT GAGAGGGACC GGGATAATGG ACCACAGTCA CAGGAGGAGA TACACTCTGT TGTACAATGC ATGCAGAAAC TGTCAAAAAC AGTGTGGGAG CTGGAGAGAT GATCAGGGGT TAAGAACACT TCCTGCTCTT CCAGAGGACC TGAGTTCACT TTTTGTAACT GCTTGTAAGT CCAGATGTCG TCTTCTGATC TCTTTCAAGC ACCCACATGT GCAGGGCATG CAGACACAGA CATATGAACA AGAACAATTA AAAATAAAT TATAACTGC (SEQ ID NO: 1) |
| Mouse FcγRI Protein NP_034316.1 | <u>MILTSFGDDMWLLTTLLLWVPVGGEVVNATKAVITLQPPWVSIFQKENVTLWCE GPHLPGDSSTQWFINGTAVQISTPSYSIPEASFQDSGEYRCQIGSSMPSDPVQL QIHNDWLLLQASRRVLTEGEPLALRCHGWKNKLVYNVVFYRNGKSFQFSSDSEV AILKTNLSHSGIYHCSGTGRHRYTSAGVSITVKELFTTPVLRASVSSPFPEGSL VTLNCETNLLLQRPGLQLHFSFYVGSKILEYRNTSSEYHIARAEREDAGFYWCE VATEDSSVLKRSPELELQVLGPQSSAP</u>VWFHILFYLSVGIMFSLNTVLYVKIHR LQREKKYNLEVPLVSEQGKKANSFQQVRSDGVYEEVTATASQTTPKEAPDGPRS SVGDCGPEQPEPLPPSDSTGAQTSQS (SEQ ID NO: 2) |
| Human FcγRI cDNA NC_000001.11 | AATATCTTGC ATGTTACAGA TTTCACTGCT CCCACCAGCT TGGAGACAAC ATGTGGTTCT TGACAACTCT GCTCCTTTGG <u>GTTCCAGTTG ATGGGCAAGT GGA</u>CACCACA AAGGCAGTGA TCACTTTGCA GCCTCCATGG GTCAGCGTGT TCCAAGAGGA AACGTAACC TTGCACTGTG AGGTGCTCCA TCTGCCTGGG AGCAGCTCTA CACAGTGGTT TCTCAATGGC ACAGCCACTC AGACCTCGAC CCCCAGCTAC AGAATCACCT CTGCCAGTGT CAATGACAGT GGTGAATACA GGTGCCAGAG AGGTCTCTCA GGGCGAAGTG ACCCCATACA GCTGGAAATC CACAGAGG<u>CT GGCTACTACT GCAGGTCTCC AGCAGAGTCT TCACGGAAGG AGAACCTCTG GCCTTGAGGT GTCATGCGTG GAAGGATAAG CTGGTGTACA</u> |

TABLE 3-continued

| | |
|---|---|
| | ATGTGCTTTA CTATCGAAAT GGCAAAGCCT TTAAGTTTTT CCACTGGAAT<br>TCTAACCTCA CCATTCTGAA AACCAACATA AGTCACAATG GCACCTACCA<br>TTGCTCAGGC ATGGGAAAGC ATCGCTACAC ATCAGCAGGA ATATCTGTCA<br>CTGTGAAAGA GCTATTTCCA GCTCCAGTGC TGAATGCATC TGTGACATCC<br>CCACTCCTGG AGGGGAATCT GGTCACCCTG AGCTGTGAAA CAAAGTTGCT<br>CTTGCAGAGG CCTGGTTTGC AGCTTTACTT CTCCTTCTAC ATGGGCAGCA<br>AGACCCTGCG AGGCAGGAAC ACATCCTCTG AATACCAAAT ACTAACTGCT<br>AGAAGAGAAG ACTCTGGGTT ATACTGGTGC GAGGCTGCCA CAGAGGATGG<br>AAATGTCCTT AAGCGCAGCC CTGAGTTGGA GCTTCAAGTG CTTGGCCTCC<br>AGTTACCAAC TCCTGTCTGG TTTCATGTCC TTTTCTATCT GGCAGTGGGA<br>ATAATGTTTT TAGTGAACAC TGTTCTCTGG GTGACAATAC GTAAAGAACT<br>GAAAAGAAAG AAAAAGTGGG ATTTAGAAAT CTCTTTGGAT TCTGGTCATG<br>AGAAGAAGGT AATTTCCAGC CTTCAAGAAG ACAGACATTT AGAAGAAGAG<br>CTGAAATGTC AGGAACAAAA AGAAGAACAG CTGCAGGAAG GGGTGCACCG<br>GAAGGAGCCC CAGGGGGCCA CGTAGCAGCG GCTCAGTGGG TGGCCATCGA<br>TCTGGACCGT CCCCTGCCCA CTTGCTCCCC GTGAGCACTG CGTACAAACA<br>TCCAAAAGTT CAACAACACC AGAACTGTGT GTCTCATGGT ATGTAACTCT<br>TAAAGCAAAT AAATGAACTG ACTTCAACTG GGATACATTT GGAAATGTGG<br>TCATCAAAGA TGACTTGAAA TGAGGCCTAC TCTAAAGAAT TCTTGAAAAA<br>CTTACAAGTC AAGCCTAGCC TGATAATCCT ATTACATAGT TTGAAAAATA<br>GTATTTTATT TCTCAGAACA AGGTAAAAG GTGAGTGGGT GCATATGTAC<br>AGAAGATTAA GACAGAGAAA CAGACAGAAA GAGACACACA CACAGCCAGG<br>AGTGGGTAGA TTTCAGGGAG ACAAGAGGGA ATAGTATAGA CAATAAGGAA<br>GGAAATAGTA CTTACAAATG ACTCCTAAGG GACTGTGAGA CTGAGAGGGC<br>TCACGCCTCT GTGTTCAGGA TACTTAGTTC ATGGCTTTTC TCTTTGACTT<br>TACTAAAAGA GAATGTCTCC ATACGCGTTC TAGGCATACA AGGGGGTAAC<br>TCATGATGAG AAATGGATGT GTTATTCTTG CCCTCTCTTT TGAGGCTCTC<br>TCATAACCCC TCTATTTCTA GAGACAACAA AAATGCTGCC AGTCCTAGGC<br>CCCTGCCCTG TAGGAAGGCA GAATGTAACT GTTCTGTTTG TTTAACGATT<br>AAGTCCAAAT CTCCAAGTGC GGCACTGCAA AGAGACGCTT CAAGTGGGGA<br>GAAGCGGCGA TACCATAGAG TCCAGATCTT GCCTCCAGAG ATTTGCTTTA<br>CCTTCCTGAT TTTCTGGTTA CTAATTAGCT TCAGGATACG CTGCTCTCAT<br>ACTTGGGCTG TAGTTTGGAG ACAAAATATT TTCCTGCCAC TGTGTAACAT<br>AGCTGAGGTA AAAACTGAAC TATGTAAATG ACTCTACTAA AAGTTTAGGG<br>AAAAAAAACA GGAGGAGTAT GACACAAAAA AAAAAAAAAA AAAAAAAAAA<br>AAAAAAAAAA AAAAAAAAAA AAAAAAAAAA AAAAAAAAAA AAAAAAAAAA<br>AAAAAAAAAA AAAAAAA (SEQ ID NO: 3) |
| Human FcγRI<br>Protein<br>AAI52384 | MWFLTTLLLWVPVDGQVDTTKAVITLQPPWVSVFQEETVTLHCEVLHLPGSSSTQ<br>WELNGTATQTSTPSYRITSASVNDSGEYRCQRGLSGRSDPIQLEIHRGWLLLQVS<br>SRVFTEGEPLALRCHAWKDKLVYNVLYYRNGKAFKFFHWNSNLTILKTNISHNGT<br>YHCSGMGKHRYTSAGISVTVKELFPAPVLNASVTSPLLEGNLVTLSCETKLLLQR<br>PGLQLYFSFYMGSKTLRGRNTSSEYQILTARREDSGLYWCEAATEDGNVLKRSPE<br>LELQVLGLQLPTPVWFHVLFYLAVGIMELVNTVLWVTIRKELKRKKKWDLEISLD<br>SGHEKKVISSLQEDRHLEEELKCQEQKEEQLQEGVHRKEPQGAT (SEQ ID<br>NO: 4) |
| Exemplary<br>Humanized<br>FcγRI Protein | MWFLTTLLLWVPVDGQVDTTKAVITLQPPWVSVFQEETVTLHCEVLHLPGSSSTQ<br>WELNGTATQTSTPSYRITSASVNDSGEYRCQRGLSGRSDPIQLEIHRGWLLLQVS<br>SRVFTEGEPLALRCHAWKDKLVYNVLYYRNGKAFKFFHWNSNLTILKTNISHNGT<br>YHCSGMGKHRYTSAGISVTVKELFPAPVLNASVTSPLLEGNLVTLSCETKLLLQR<br>PGLQLYFSFYMGSKTLRGRNTSSEYQILTARREDSGLYWCEAATEDGNVLKRSPE<br>LELQVLGLQLPTPVWGPQSSAPVWFHILFYLSVGIMFSLNTVLYVKIHRLQREKK<br>YNLEVPLVSEQGKKANSFQQVRSDGVYEEVTATASQTTPKEAPDGPRSSVGDCGP<br>EQPEPLPPSDSTGAQTSQS (SEQ ID NO: 5) |

Humanized FcγRI Non-Human Animals

Non-human animals are provided that express humanized FcγRI receptor proteins on the surface of immune cells (e.g., myeloid cells) of the non-human animals resulting from a genetic modification of an endogenous locus of the non-human animal that encodes an FcγRI protein. Suitable examples described herein include rodents, in particular, mice.

A humanized endogenous FcγRI gene, in some embodiments, comprises genetic material from a heterologous species (e.g., humans), wherein the humanized endogenous FcγRI gene encodes a FcγRI protein that comprises the encoded portion of the genetic material from the heterologous species. In some embodiments, a humanized endogenous FcγRI gene of the present invention comprises genomic DNA of a heterologous species that corresponds to the extracellular portion of a FcγRI protein that is expressed on the plasma membrane of a cell. Non-human animals, embryos, cells and targeting constructs for making non-human animals, non-human embryos, and cells containing said humanized endogenous FcγRI gene are also provided.

In some embodiments, the endogenous FcγRI locus is deleted. In some embodiments, the endogenous FcγRI locus is altered, wherein a portion of the endogenous FcγRI locus is replaced with a heterologous sequence (e.g., a human FcγRI sequence in whole or in part). In some embodiments, all or substantially all of the endogenous FcγRI locus is replaced with a heterologous locus (e.g., a human FcγRI locus). In some embodiments, a portion of a heterologous FcγRI locus is inserted into an endogenous non-human FcγRI locus. In some embodiments, the heterologous locus is a human locus.

A non-human animal of the present invention contains a human FcγRI gene in whole or in part at an endogenous non-human FcγRI locus. Thus, such non-human animals can be described as having a heterologous FcγRI gene. The replaced, inserted or modified endogenous FcγRI locus can be detected using a variety of methods including, for example, PCR, Western blot, Southern blot, restriction fragment length polymorphism (RFLP), or a gain or loss of allele assay.

In various embodiments, a humanized FcγRI gene according to the present invention includes a FcγRI gene that has a third, fourth and fifth exon each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a third, fourth, and fifth exon that appear in a human FcγRI gene of SEQ ID NO: 3.

In various embodiments, a humanized FcγRI gene according to the present invention includes a FcγRI gene that has a nucleotide coding sequence (e.g., a cDNA sequence) at least 50% (e.g., 50%, 55%, 60%, 65%, 70%, 75%, 80%, 85%, 90%, 91%, 92%, 93%, 94%, 95%, 96%, 97%, 98%, 99% or more) identical to nucleotides that appear in SEQ ID NO: 5.

In various embodiments, a humanized FcγRI protein produced by a non-human animal of the present invention has an extracellular portion having a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an extracellular portion of a human FcγRI protein that appears in Table 3.

In various embodiments, a humanized FcγRI protein produced by a non-human animal of the present invention has an extracellular portion having a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 18-288 that appear in a human FcγRI protein of SEQ ID NO: 4.

In various embodiments, a humanized FcγRI protein produced by a non-human animal of the present invention has an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an amino acid sequence of a humanized FcγRI protein as exemplified in SEQ ID NO: 5.

Compositions and methods for making non-human animals that expresses a humanized FcγRI protein, including specific polymorphic forms or allelic variants (e.g., single amino acid differences), are provided, including compositions and methods for making non-human animals that expresses such proteins from a human promoter and a human regulatory sequence. In some embodiments, compositions and methods for making non-human animals that expresses such proteins from an endogenous promoter and an endogenous regulatory sequence are also provided. The methods include inserting the genetic material encoding a human FcγRI protein in whole or in part at a precise location in the genome of a non-human animal that corresponds to an endogenous FcγRI gene thereby creating a humanized FcγRI gene that expresses a FcγRI protein that is human in whole or in part. In some embodiments, the methods include inserting genomic DNA corresponding to exons 3-5 a humanized gene that encodes a FcγRI protein that contains a human portion containing amino acids encoded by the inserted exons.

A humanized endogenous FcγRI gene approach employs a relatively minimal modification of the endogenous gene and results in natural FcγRI mediated effector responses in the non-human animal, in various embodiments, because the genomic sequence of the FcγRI sequences are modified in a single fragment and therefore retain normal functionality by including necessary regulatory sequences. Thus, in such embodiments, the FcγRI gene modification does not affect other surrounding genes or other endogenous FcγRI genes. Further, in various embodiments, the modification does not affect the assembly of a functional receptor on the plasma and maintains normal effector functions via binding and subsequent signal transduction through the cytoplasmic portion of the receptor which is minimally or unaffected by the modification.

Figure 5:
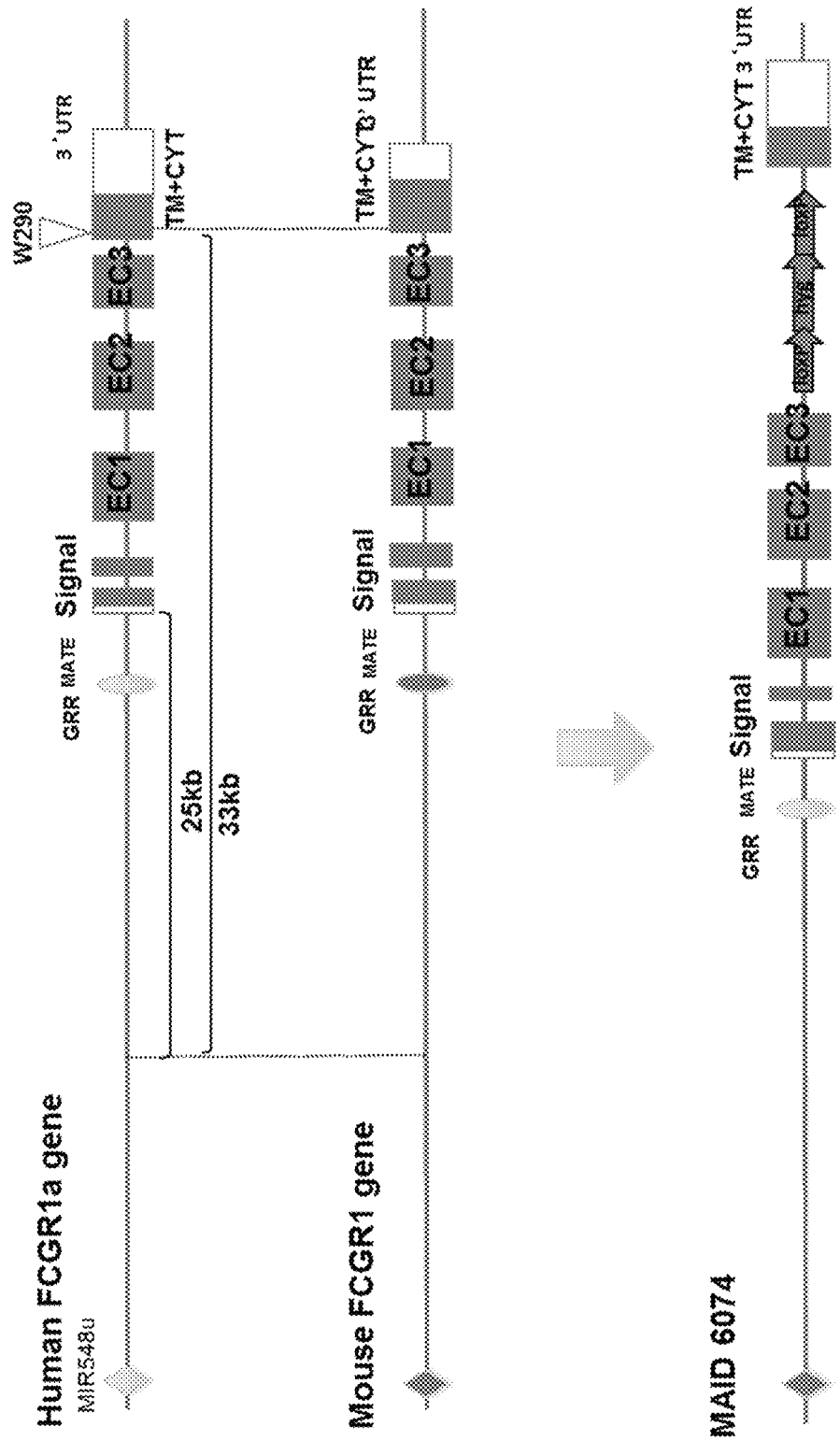
FIG. 5 shows a schematic illustration (not to scale) of a human FcγRI gene, a mouse FcγRI gene, and a humanized FcγRI gene.

A schematic illustration (not to scale) of an endogenous murine FcγRI gene and a humanized endogenous FcγRI gene is provided in FIG. 5. As illustrated, genomic DNA containing exons 3-5 of a human FcγRI gene is inserted into an endogenous murine FcγRI gene locus by a targeting construct. This genomic DNA includes comprises the portion of the gene that encodes one or more extracellular domain regions (e.g., amino acid resides 28-362) of a human FcγRI protein that participate in Fc binding.

A non-human animal (e.g., a mouse) having a humanized endogenous FcγRI gene can be made by any method known in the art. For example, a targeting vector can be made that introduces a human FcγRI gene in whole or in part with a selectable marker gene. FIG. 5 illustrates a mouse genome comprising an insertion of exons 1-5 of a human FcγRI. As illustrated, the targeting construct contains a 5' homology arm containing sequence upstream of exon 1 of an endogenous murine FcγRI gene, followed by a genomic DNA fragment containing exons 1-5 of a human FcγRI gene, a drug selection cassette (e.g., a neomycin resistance gene flanked on both sides by loxP sequences), and a 3' homology arm containing sequence downstream of exons 6 of an endogenous murine FcγRI gene. Upon homologous recombination, exons 1-5 and a portion of exon 6 of an endogenous murine FcγRI gene is replaced by the sequence contained in the targeting vector. A humanized endogenous FcγRI gene is created resulting in a cell or non-human animal that expresses a humanized FcγRI protein that contains amino acids encoded by exons 1-5 of a human FcγRI gene. The drug selection cassette may optionally be removed by the subsequent addition of a recombinase (e.g., by Cre treatment).

In addition to mice having humanized FcγRI genes as described herein, also provided herein are other genetically modified non-human animals that comprise humanized FcγRI genes. In some embodiments, such non-human animals comprise a humanized FcγRI gene operably linked to an endogenous FcγRI promoter. In some embodiments, such non-human animals express a humanized FcγRI protein from an endogenous locus, wherein the humanized FcγRI protein comprises amino acid residues 16-290 of a human FcγRI protein.

Such non-human animals may be selected from the group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising genetic modifications as described herein. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In some embodiments, a non-human animal of the present invention is a mammal. In some embodiments, a non-human animal of the present invention is a small mammal, e.g., of the superfamily Dipodoidea or Muroidea. In some embodiments, a genetically modified animal of the present invention is a rodent. In some embodiments, a rodent of the present invention is selected from a mouse, a rat, and a hamster. In some embodiments, a rodent of the present invention is selected from the superfamily Muroidea. In some embodiments, a genetically modified animal of the present invention is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In some certain embodiments, a genetically modified rodent of the present invention is selected from a true mouse or rat (family Muridae), a gerbil, a spiny mouse, and a crested rat. In some certain embodiments, a genetically modified mouse of the present invention is from a member of the family Muridae. In some embodiment, an non-human animal of the present invention is a rodent. In some certain embodiments, a rodent of the present invention is selected from a mouse and a rat. In some embodiments, a non-human animal of the present invention is a mouse.

In some embodiments, a non-human animal of the present invention is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some certain embodiments, a mouse of the present invention is a 129 strain selected from the group consisting of a strain that is 129P1, 129P2, 129P3,129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al., 1999, *Mammalian Genome* 10:836; Auerbach et al., 2000, *Biotechniques* 29(5): 1024-1028, 1030, 1032). In some certain embodiments, a genetically modified mouse of the present invention is a mix of an aforementioned 129 strain and an aforementioned C57BL/6 strain. In some certain embodiments, a mouse of the present invention is a mix of aforementioned 129 strains, or a mix of aforementioned BL/6 strains. In some certain embodiments, a 129 strain of the mix as described herein is a 129S6 (129/SvEvTac) strain. In some embodiments, a mouse of the present invention is a BALB strain, e.g., BALB/c strain. In some embodiments, a mouse of the present invention is a mix of a BALB strain and another aforementioned strain.

In some embodiments, a non-human animal of the present invention is a rat. In some certain embodiments, a rat of the present invention is selected from a Wistar rat, an LEA strain, a Sprague Dawley strain, a Fischer strain, F344, F6, and Dark Agouti. In some certain embodiments, a rat strain as described herein is a mix of two or more strains selected from the group consisting of Wistar, LEA, Sprague Dawley, Fischer, F344, F6, and Dark Agouti.

Non-Human Animals Having Humanized FcγRI Genes

FcγR mutant and transgenic non-human animals (e.g., mice) have been reported, for example, by van de Winkel et al. in U.S. Pat. No. 6,111,166.

Such animals have been employed in assays to assess the molecular aspects of FcγRI expression, function and regulation. However, they are not without limitations and disadvantages. For example, the mouse disclosed in the '166 patent contains human FcγRI randomly inserted into its genome, which (1) may disrupt the expression and or function of other genes unintentionally, whether detected or not, and (2) results in expression of both fully human and fully mouse FcγRI which complicates or confounds particular study of a single type of FcγR. Moreover, intracellular signaling region of FcγRIα chain may be perturbed, disrupted, or otherwise not in accordance with normal FcγRI in the mouse disclosed in the '116 patent because the intracellular region of the FcγRIα chain that participates in signal transduction is human rather than mouse.

The present invention provides a means to overcome these and other disadvantages. The present invention provides, among other things, a humanized FcγRI transgene inserted at an endogenous mouse locus to replace mouse FcγRI with a human or hybrid FcγRI gene. In some embodiments, a hybrid FcγRI gene is inserted at the endogenous mouse locus, wherein the extracellular domain comprises a human sequence and the intracellular domain comprises a mouse sequence. In some embodiments, insertion of a hybrid FcγRI gene at an endogenous locus of mouse FcγRI gene provides expression of FcγRI protein on immune cells that more closely resembles the distribution of human FcγRI protein on human immune cells as compared to the distribution of human FcγRI protein expression on immune cells of a mouse that additionally expresses an endogenous mouse FcγRI protein. In some embodiments, insertion of a hybrid FcγRI gene at an endogenous locus of mouse FcγRI gene provides expression of FcγRI protein on immune cells that is induced and regulated by appropriate signals and stimuli.

In some embodiments, FcγRIα chain mediated presentation of MHC class II antigens is functionally maintained in mice having a hybrid FcγRI protein with a humanized extracellular region a mouse FcγRIα chain intracellular region. In some embodiments, intracellular processing of internalized FcγRI is preserved in a mouse having a hybrid FcγRI protein with a mouse intracellular region as compared to that in a mouse having a fully human FcγRI protein or an FcγRI protein with a non-murine intracellular region.

Non-human animals of the present invention provide an improved in vivo system and source of biological materials (e.g., cells) expressing human FcγRI that are useful for a variety of assays. In various embodiments, non-human animals of the present invention are used to develop therapeutics that target FcγRI and/or modulate FcγRI signaling and immune effector responses. In various embodiments, mice of the present invention are used to screen and develop candidate therapeutics (e.g., antibodies) to which FcγRI binds. In various embodiments, non-human animals of the present invention are used to determine the immune effector response associated with a particular therapeutic antibody.

Genetically modified non-human animals that do not express endogenous high affinity mouse FcγR genes are useful, e.g., to elucidate the various functions of the individual high affinity FcγR genes in the immune response, to measure the efficacy of a human therapeutic antibody via cell-mediated immunity (e.g., ADCC), to determine a role of FcγR in immune diseases or disorders, to serve as models of immune diseases or disorders, to generate antibodies against one or more FcγR proteins, and to serve as breeding mates to generate other genetically modified mice of interest.

In one embodiment, a mouse according to the invention can be used to determine a cytotoxic effect lost (in comparison to a wild type mouse) by a mouse that does not express high affinity FcγR genes by administering an agent to such a mouse, where the agent is known to trigger an FcγR dependent cytotoxic effect in wild type mice. In one embodiment, a mouse of the present invention is implanted with tumor cells and, after a subsequent period of time, injected with an antibody specific for an antigen expressed on the surface of the tumor cells. The isotype of the antibody is known prior to injection and the animals are analyzed for impairment of FcγR-dependent ADCC by comparison to ADCC observed in wild type animals.

In one aspect, mice deficient in endogenous high affinity receptors could be combined (e.g., by breeding) with other immune deficient mice to develop in vivo models of autoimmune disease. For example, Severe Combined Immunodeficiency (SCID) mice are routinely used in the art as model organisms for studying the inner system. Scm mice have an impaired ability to make Tor B lymphocytes, or activate some components of the complement system, and cannot efficiently fight infections, reject tumors, and reject transplants. High affinity FcγR a-subunit gene-deficient mice of the present invention may be bred to SCID mice to ascertain cell depletion in a host animal in response to administration of an antibody therapeutic (e.g., an anti-tumor antibody), which would determine the roles of ADCC and complement dependent cytotoxicity (CDC) in tumor cell depletion in vivo.

In some embodiments, genetically modified non-human animals comprising a replacement of the endogenous high affinity FcγR genes with high-affinity human FcγR genes are provided. Such animals are useful for studying the pharmacokinetics of fully human antibodies and FcγR-mediated ADCC. In addition, human FcγR genes have been shown to exhibit polymorphisms or allelic variants associated with disease. Thus, genetically modified non-human animals that comprise a replacement of the endogenous high affinity FcγR genes with specific allelic or polymorphic forms of human FcγR genes can be used to study human autoimmune diseases, and traits associated with the polymorphisms, in the animal. In some embodiments, the allelic forms of human FcγR genes are associated with enhanced efficacy for human IgG.

In some embodiments, the effect of a human high affinity FcγR polymorphism on the efficacy of a human antibody therapeutic is determined. In some embodiments, an anti-tumor antibody is administered to a first humanized mouse comprising a first polymorphism of a human FcγR and also to a second humanized mouse comprising a second polymorphism of a human FcγR, wherein the first and the second mice each comprise a human tumor cell; and the anti-tumor activity of the anti-tumor antibody is assessed in the first mouse and in the second mouse.

In some embodiments, a treatment option is selected by a physician with respect to treating a human having the first or the second polymorphism and having a tumor corresponding to the human tumor cell based on the assessment of efficacy of the anti-tumor antibody in the first mouse and in the second mouse.

The endogenous FcγRI α-chain replacement approach employs a relatively minimal disruption of natural FcγR-mediated signal transduction in the animal. In various embodiments, genomic sequence of the FcγR α-chains are replaced in a single fragment and therefore retain normal functionality by including necessary regulatory sequences. Thus, in such embodiments, the FcγR α-chain modification does not impair other endogenous FcRs dependent upon functional FcRγ-chain molecules. Further, in various embodiments, the modification does not affect the assembly of functional receptor complex involving an FcγR α-chain and the endogenous FcRγ-chain, which may be important for proper expression of some FcγR α-chains on the cell surface and for certain downstream signaling resulting from an activated receptor. Because the FcR γ-chain is not deleted, in various embodiments animals containing a replacement of endogenous FcγR α-chain genes with human FcγR α-chain genes may process normal effector functions from antibodies through binding of the Fc portion of IgG immunoglobulins to the human FcγR α-chains present on the surface of accessory cells.

Non-human animals of the present invention express humanized FcγRI protein, thus cells, cell lines, and cell cultures can be generated to serve as a source of humanized FcγRI for use in binding and functional assays, e.g., to assay for binding or function of FcγRI to a potential therapeutic antibody. In various embodiments, a humanized FcγRI protein expressed by a non-human animal as described herein may comprise a variant amino acid sequence. Variant human FcγRI proteins having variations associated with ligand binding residues have been reported. In various embodiments, non-human animals of the present invention express a humanized FcγRI protein variant. In various embodiments, the variant is polymorphic at an amino acid position associated with ligand binding. In various embodiments, non-human animals of the present invention are used to determine the immune effector response of a therapeutic antibody through interaction with a polymorphic variant of human FcγRI.

Cells from non-human animals of the present invention can be isolated and used on an ad hoc basis, or can be maintained in culture for many generations. In various embodiments, cells from a non-human animal of the present invention are immortalized and maintained in culture indefinitely (e.g., in serial cultures).

Non-human animals of the present invention provide improved in vivo system elucidating mechanisms of antibody dependent cell mediated cytotoxicity.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. Humanization of an Endogenous FcγRI Gene

This example illustrates exemplary methods of humanizing an endogenous gene encoding high affinity FcγRI in a non-human mammal such as a rodent (e.g., a mouse).
Construction of Humanization FcγRI Targeting Vector (MAID6074)

A large targeting vector (LTVEC) was constructed by using the human Fc Gamma Receptor 1 gene (promoter region, signal plus ecto domain region) to replace the mouse counterparts sequence on murine chromosome 3.
Generation of BAC-Based Targeting Vectors (MAID6073)

Mouse BAC RP23-477p23 and human BAC CTD-2339o22 containing the gene of FcγRI were identified using blast and BAC end sequence based on database of NCBI and Ensemble.

The approach to generate targeting vectors, the LTVEC contained human sequence from (5' distal end) FcγRI gene promoter (25 kb) to the 3' proximal end at the gene codon W290 (before its transmembrane domain (TM)) of the human FcγRI gene, (followed by the mouse transmembrane domain and the rest of gene), involves the following steps.

First, by homologous recombination in bacteria, 5' end of human sequence from human BAC(CTD-2339o22)

removed and left a I-Ceu1 site and a 25 kb promoter region of the FcγRI gene, 3' end human sequence removed by the loxped pgk-Neo cassette located in the intron 5 (404 bp upstream of TM domain) of FcγR1 gene, followed by AsiS1 site.

Second, by homologous recombination in bacteria, in Mouse BAC RP23-477p23, mouse FcγRI gene (from its promoter (20 kb) up to the transmembrane domain) removed by a Spec cassette (8 AA of EC3 domain of human FcγRI sequence (up to the codon W290) added before mouse TM) flanked by I-Ceu1 and AsiS1 sites.

Third, digestion and ligation by I-Ceu1 and AsiS1 sites to generate the LTVEC (MAID6073) contained human sequence from the (5' distal end) FcγRI gene promoter (25 kb) to the 3' proximal end at the codon W290 (before the transmembrane domain) of the human FcγRI, followed by the mouse transmembrane domain and the rest of gene.

Figure 6:
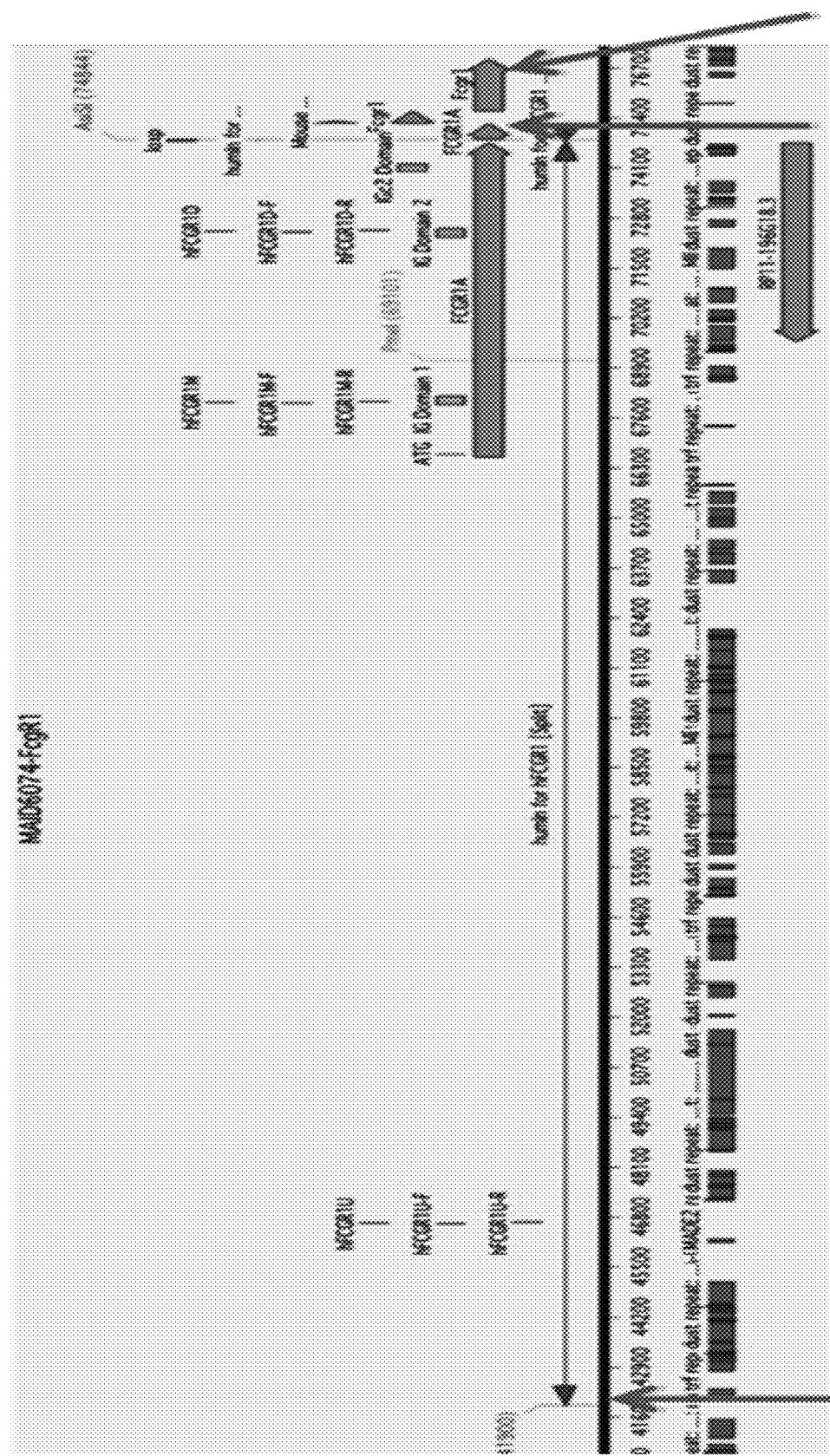
FIG. 6 shows a schematic illustration (not to scale) of a process of preparing a MAID 6074 cassette. Sequences disclosed as SEQ ID NOS 6-8, respectively, in order of appearance.
Figure 7:
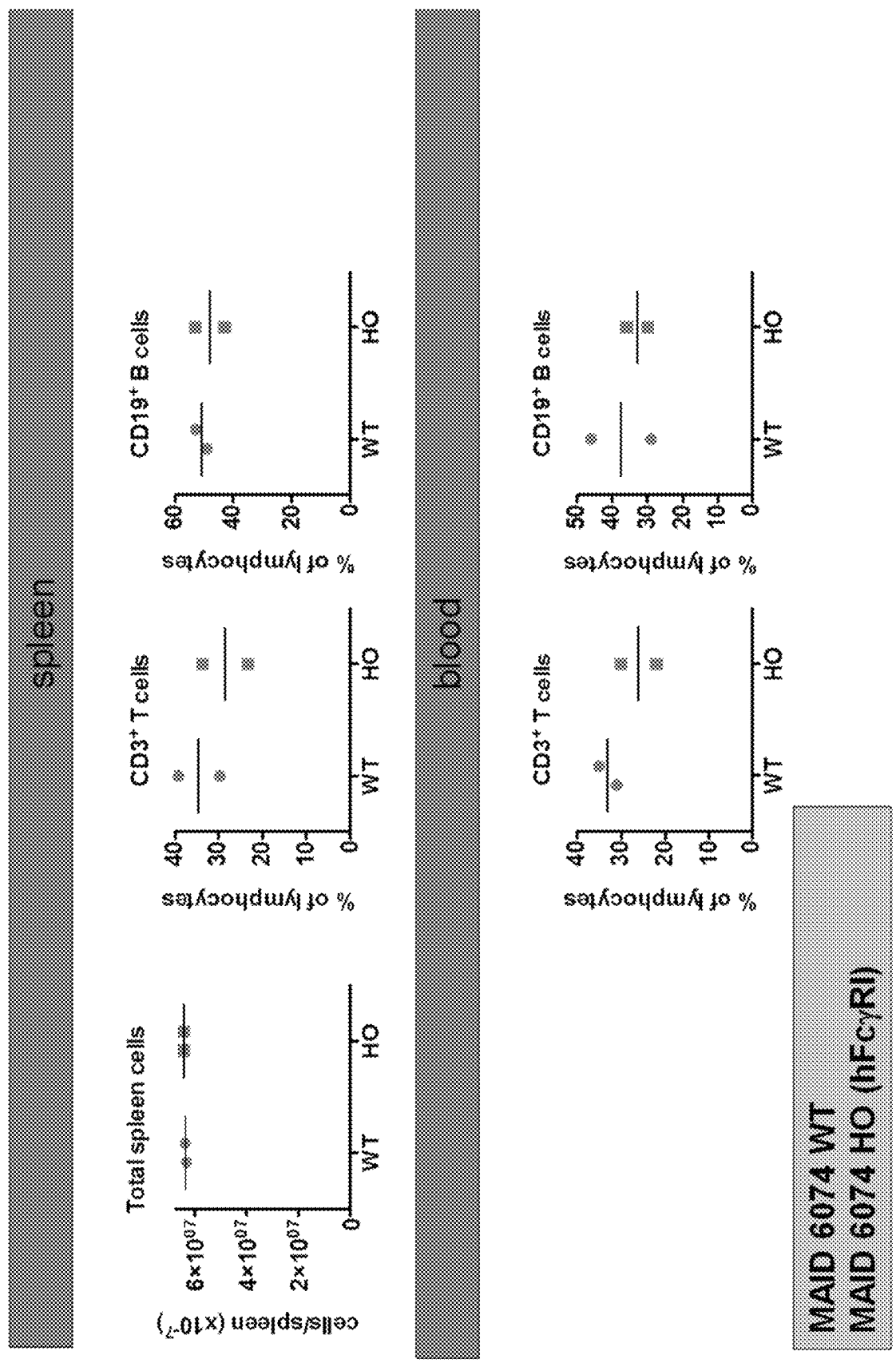
FIG. 7 shows mice having a humanized FcγRI gene exhibit normal cell frequencies in spleen and blood.
Figure 8:
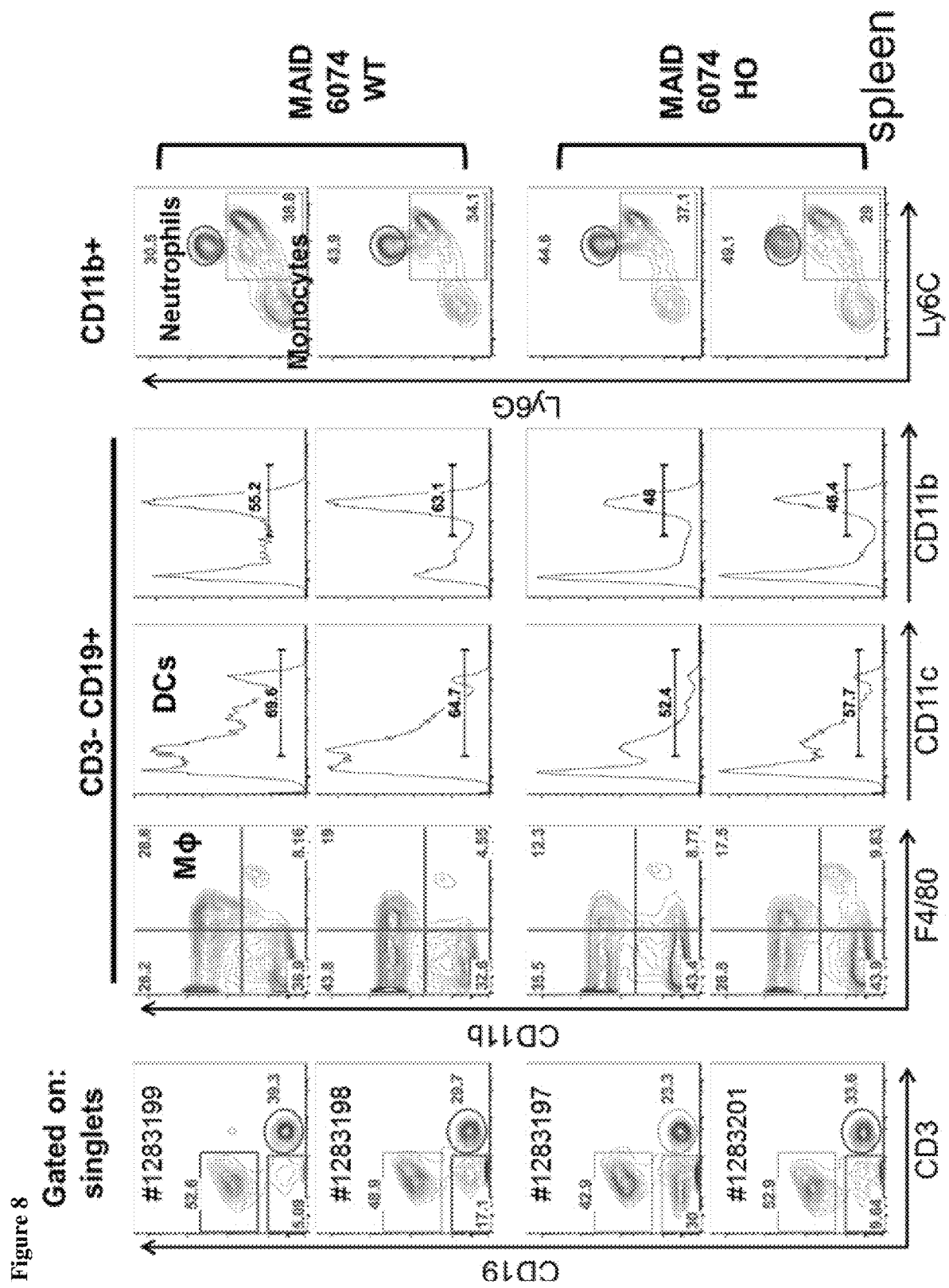
FIG. 8 shows myeloid spleen populations in mice having a humanized FcγRI gene.
Figure 9:
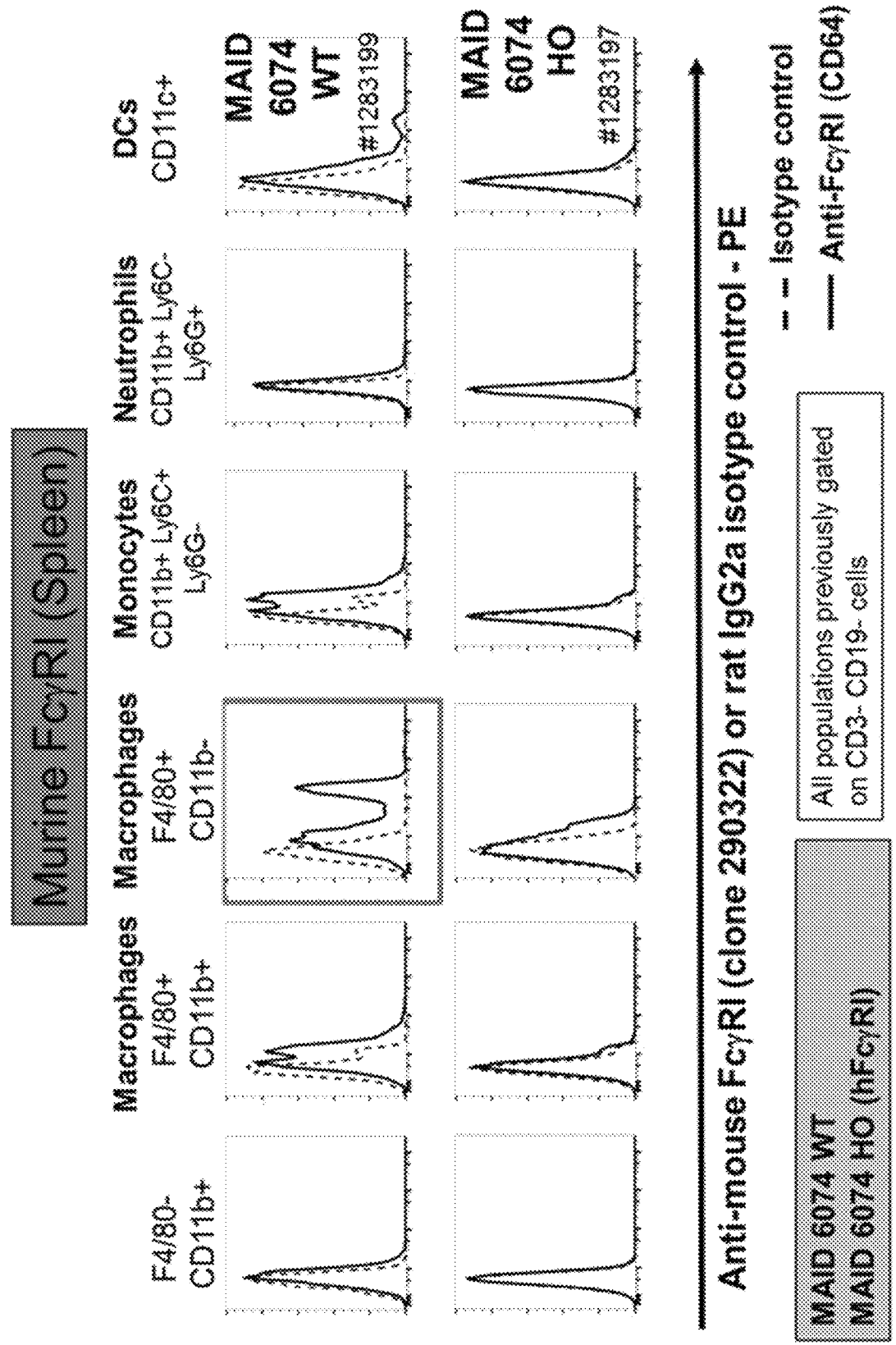
FIG. 9 shows a loss of murine FcγRI expression on macrophages from the spleen of mice having a humanized FcγRI gene.
Figure 10:
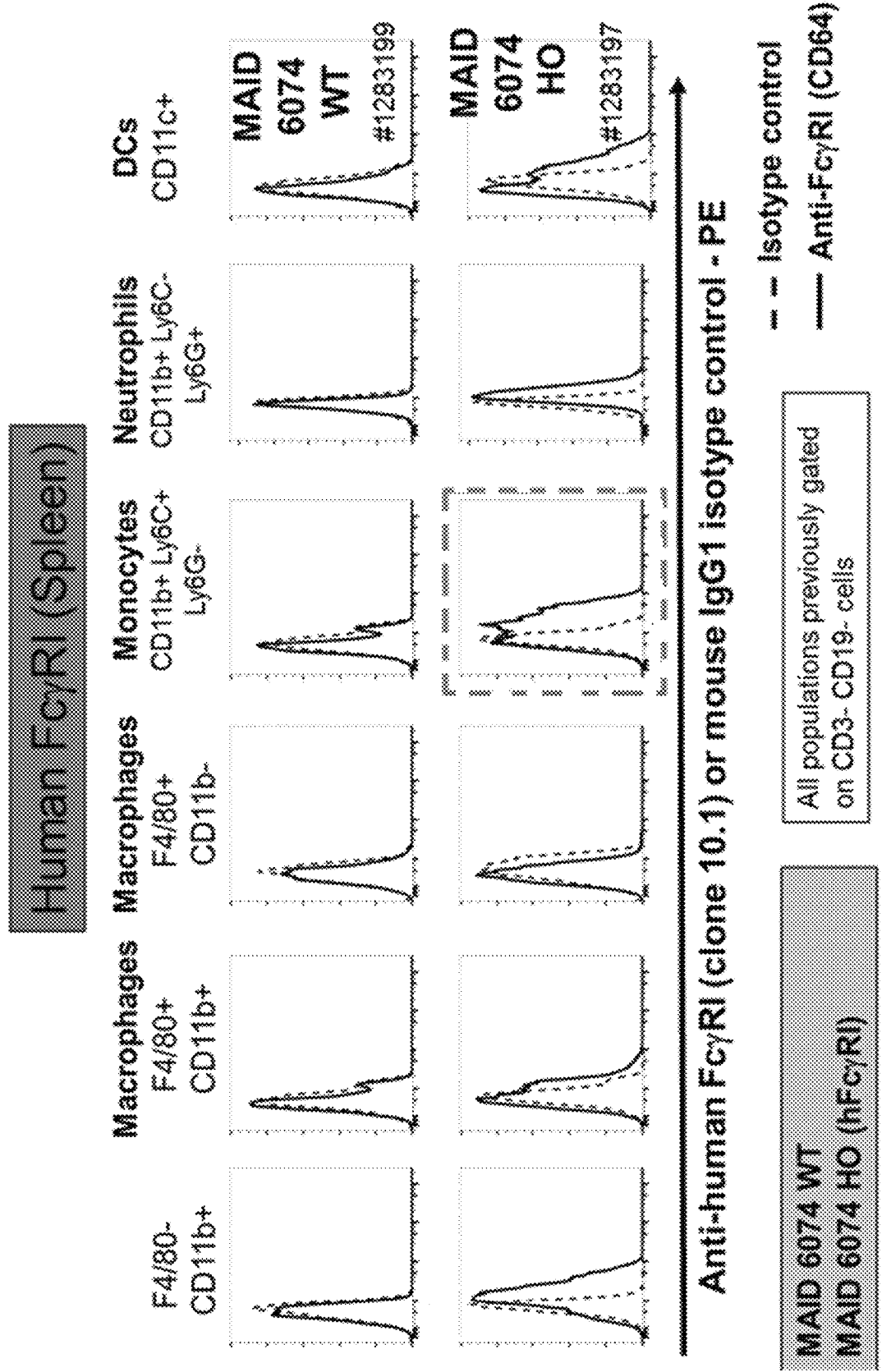
FIG. 10 shows a gain of human FcγRI expression on monocytes from the spleen of mice having a humanized FcγRI gene.
Figure 11:
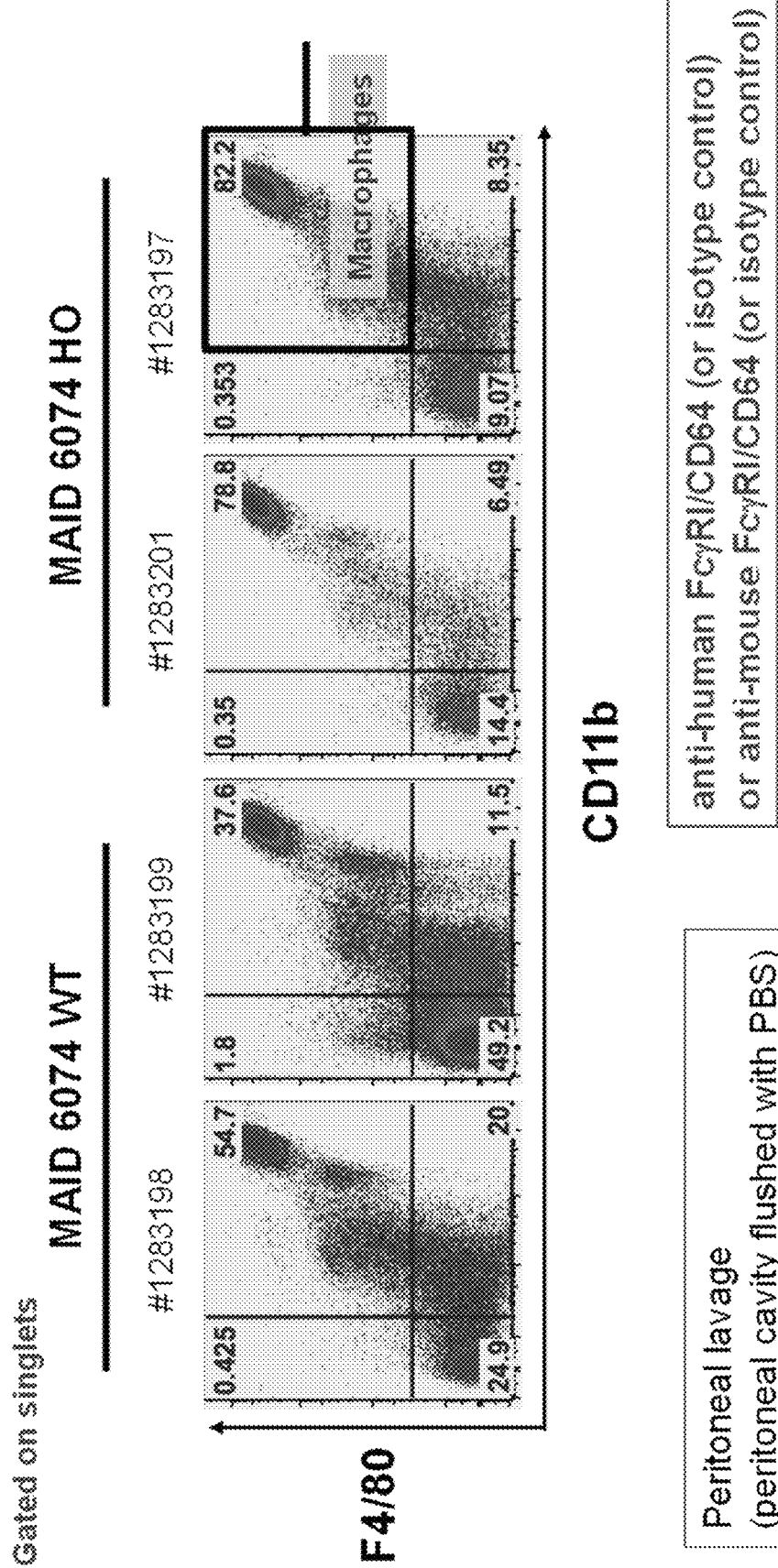
FIG. 11 shows the gating strategy during FACS analysis of macrophages purified from the peritoneal cavity of mice having endogenous mouse FcγRI genes (MAID 6074 WT) and mice homozygous for a humanized FcγRI gene (MAID 6074 HO).
Figure 12:
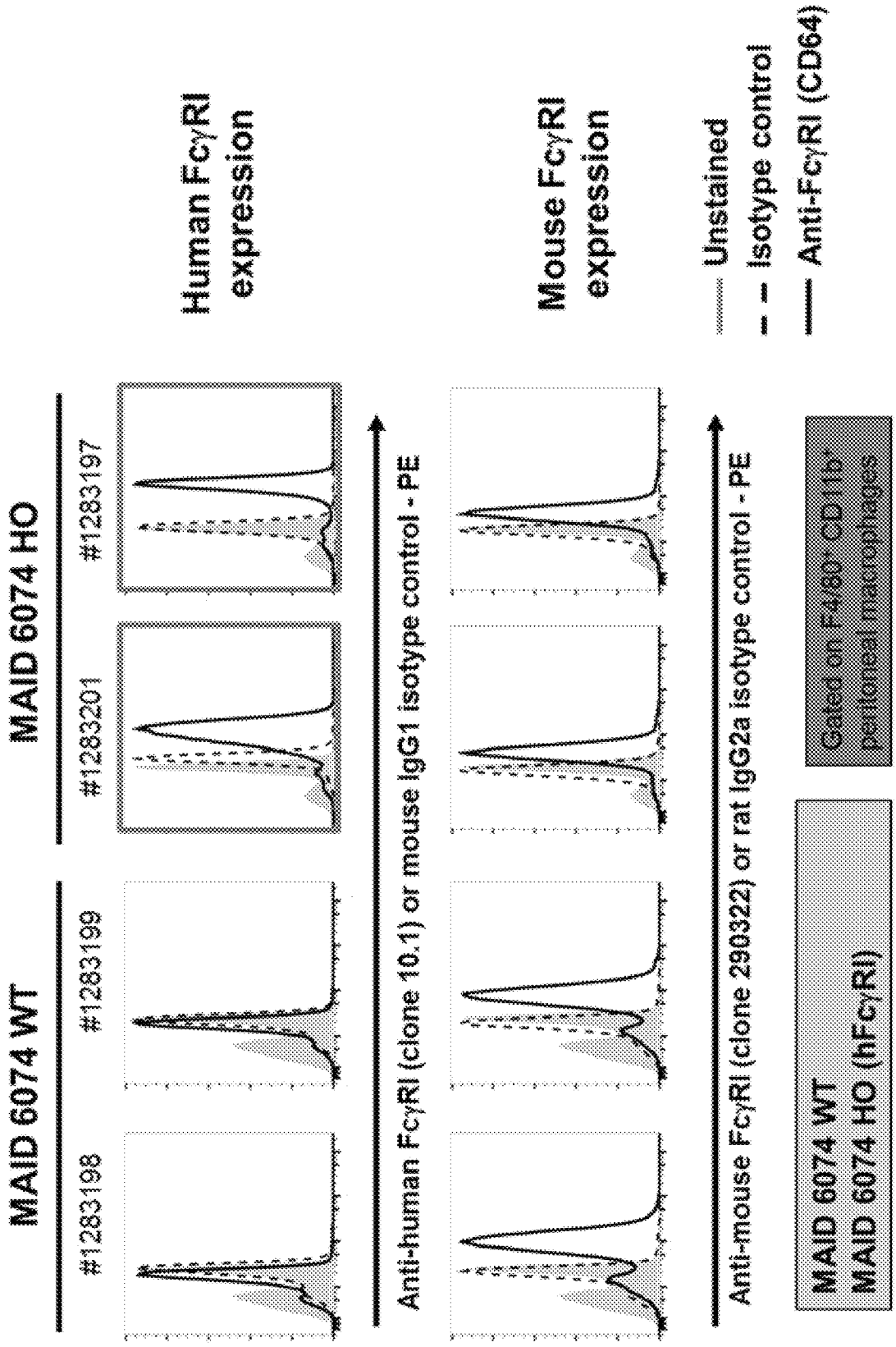
FIG. 12 shows expression of human FcγRI and mouse FcγRI in macrophages from the peritoneal cavity of mice having endogenous mouse FcγRI genes (MAID 6074 WT) and mice homozygous for a humanized FcγRI gene (MAID 6074 HO).
Figure 13:
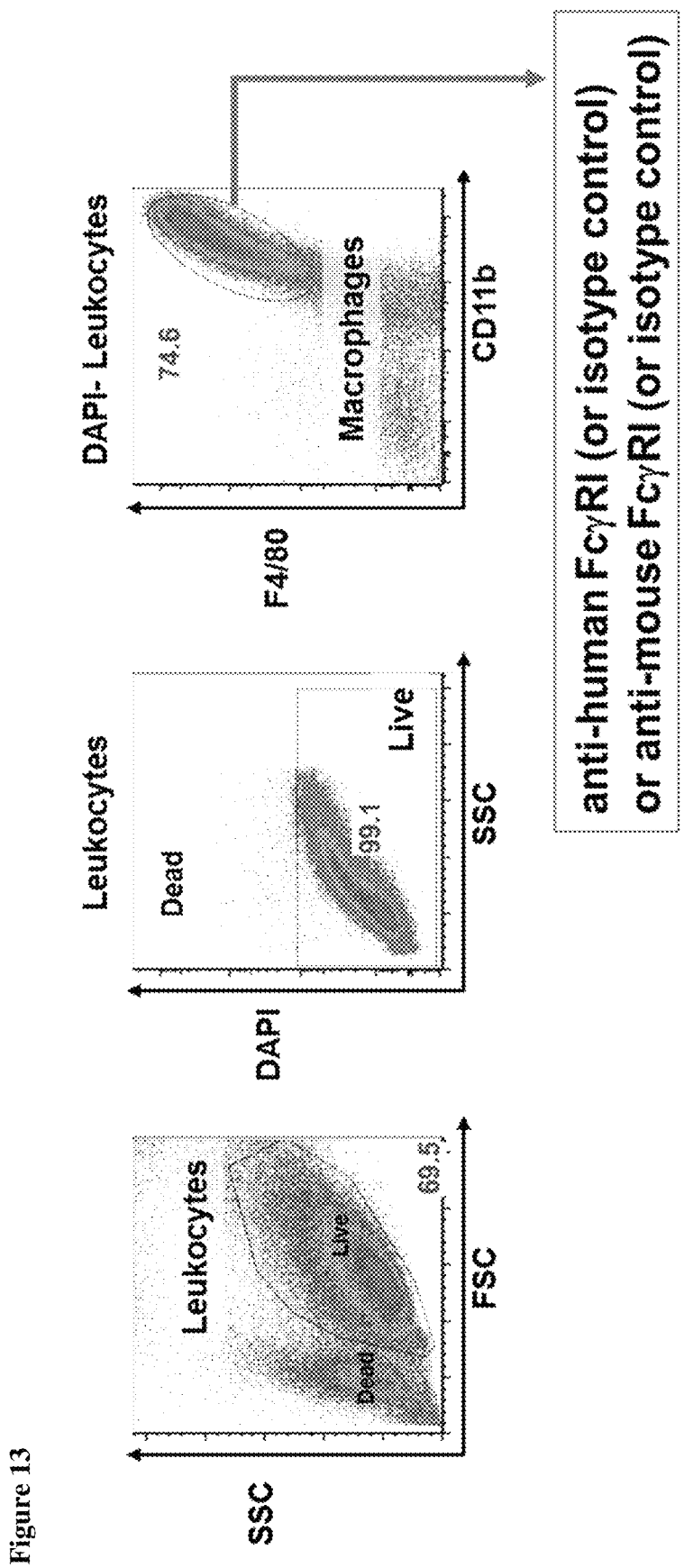
FIG. 13 shows the gating strategy during FACS analysis of bone marrow derived macrophages of mice having endogenous mouse FcγRI genes (MAID 6074 WT) and mice homozygous for a humanized FcγRI gene (MAID 6074 HO).
Figure 14:
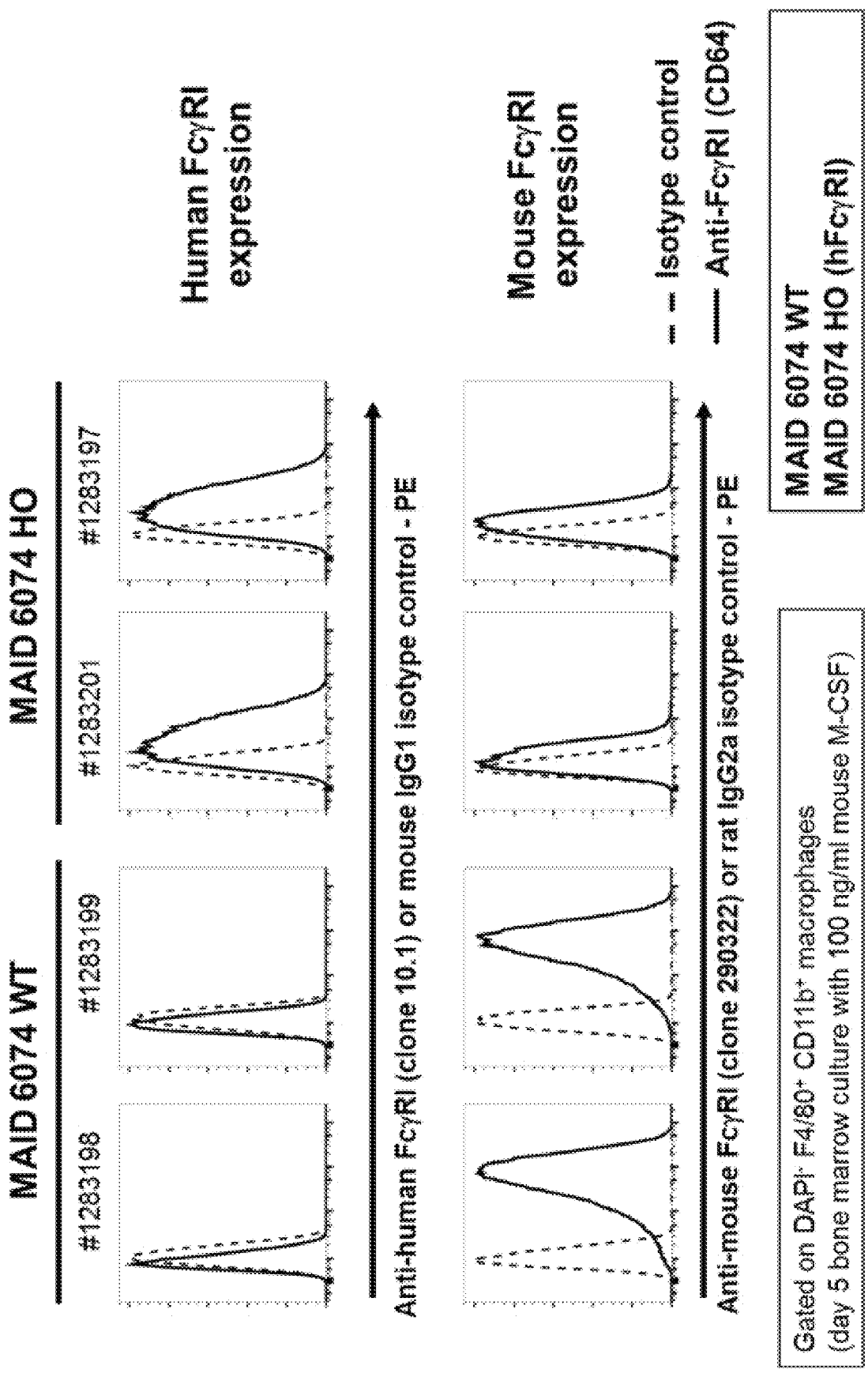
FIG. 14 shows expression of human FcγRI and mouse FcγRI in bone marrow-derived macrophages of mice having endogenous mouse FcγRI genes (MAID 6074 WT) and mice homozygous for a humanized FcγRI gene (MAID 6074 HO).
Figure 15:
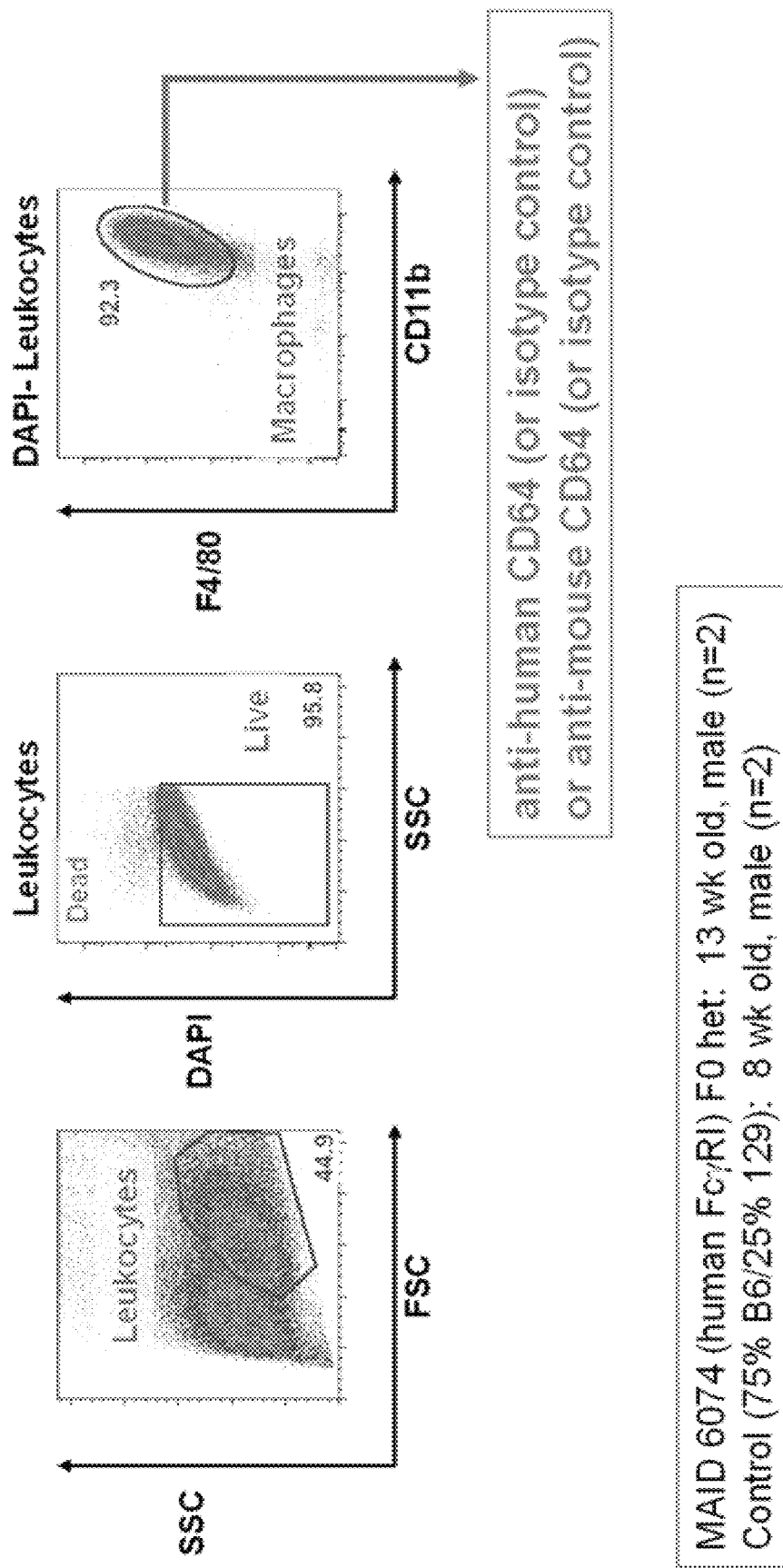
FIG. 15 shows the gating strategy during FACS analysis of bone marrow derived macrophages of mice having endogenous mouse FcγRI genes (Control 75/25) and mice heterozygous for a humanized FcγRI gene (MAID 6074 HET).
Figure 16:
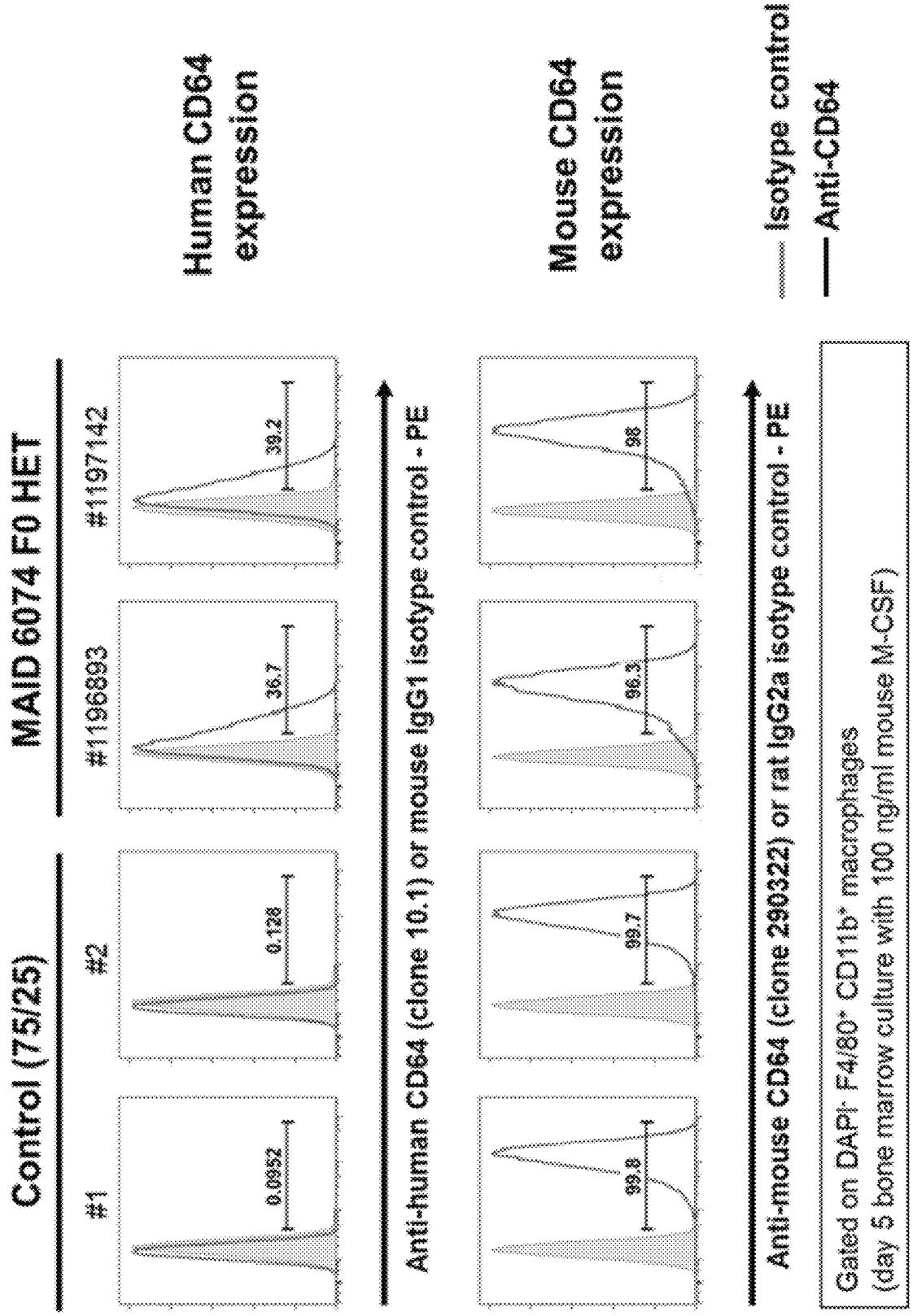
FIG. 16 shows expression of human FcγRI and mouse FcγRI in bone marrow-derived macrophages of mice having endogenous mouse FcγRI genes (Control 75/25) and mice heterozygous for a humanized FcγRI gene (MAID 6074 HET).
Figure 17:
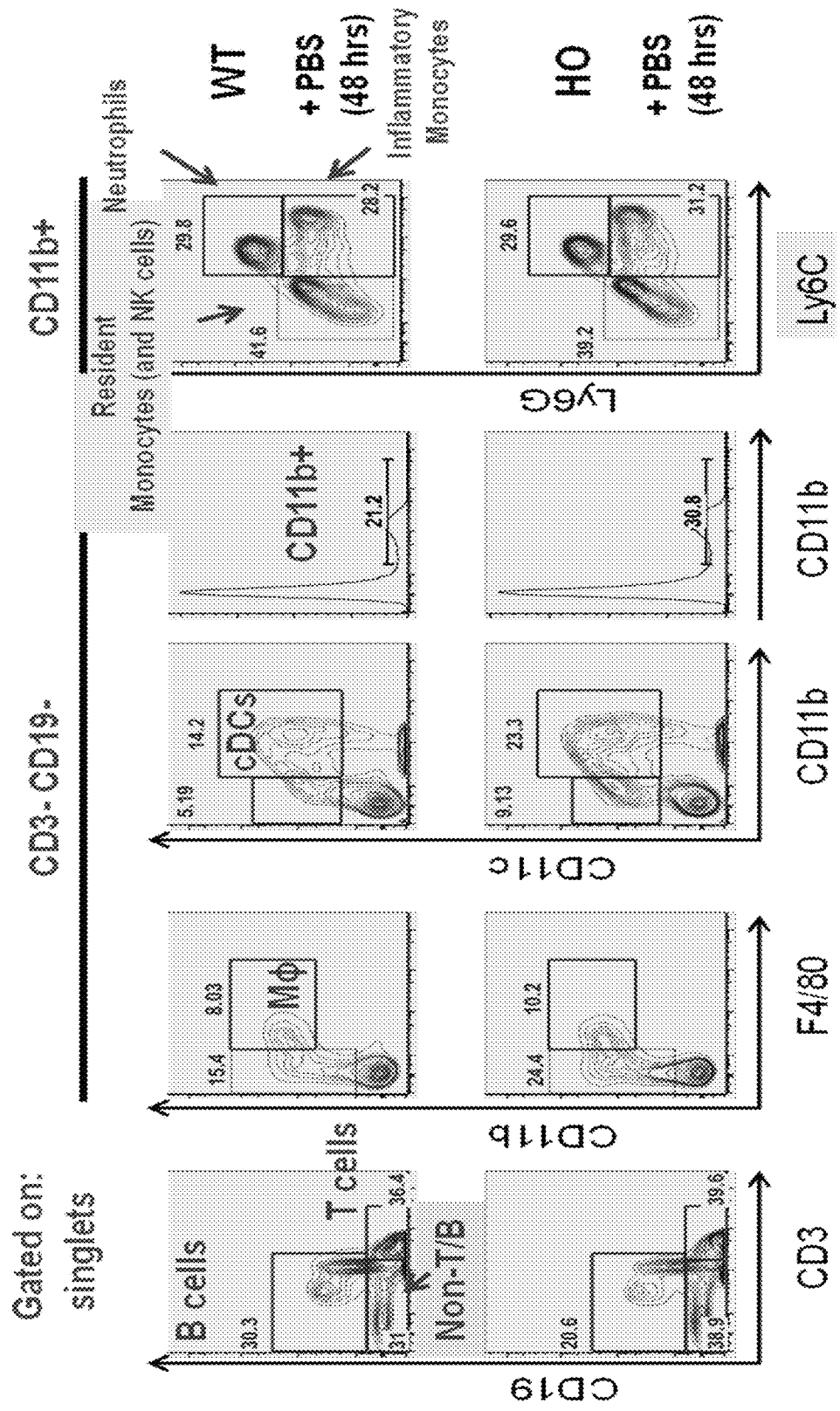
FIG. 17 shows myeloid blood populations in MAID 6074 HO mice compared to MAID 6074 WT 48 hours after treatment with PBS.
Figure 18:
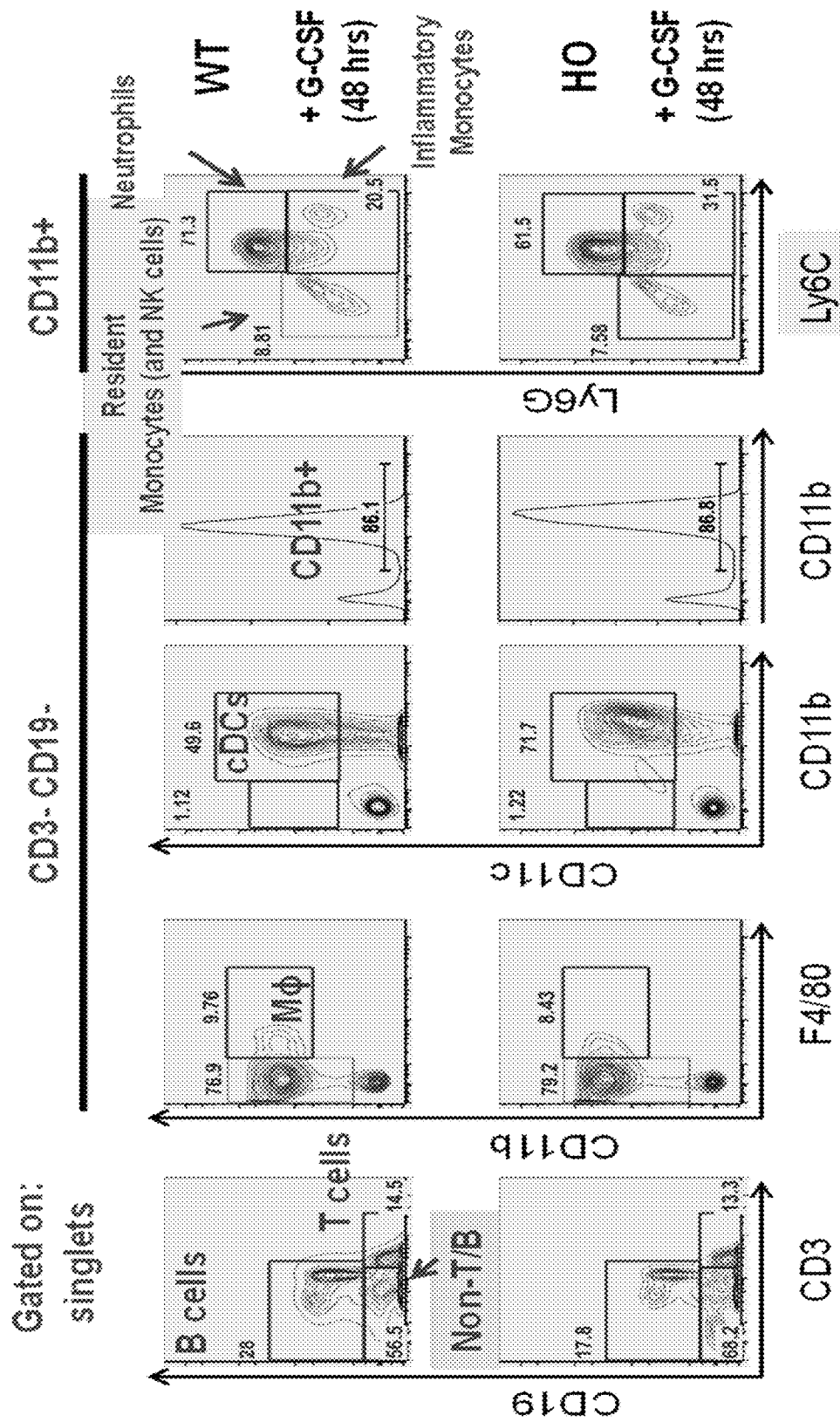
FIG. 18 shows myeloid blood populations in MAID 6074 HO mice compared to MAID 6074 WT mice 48 hours after treatment with mG-CSF.
Figure 19:
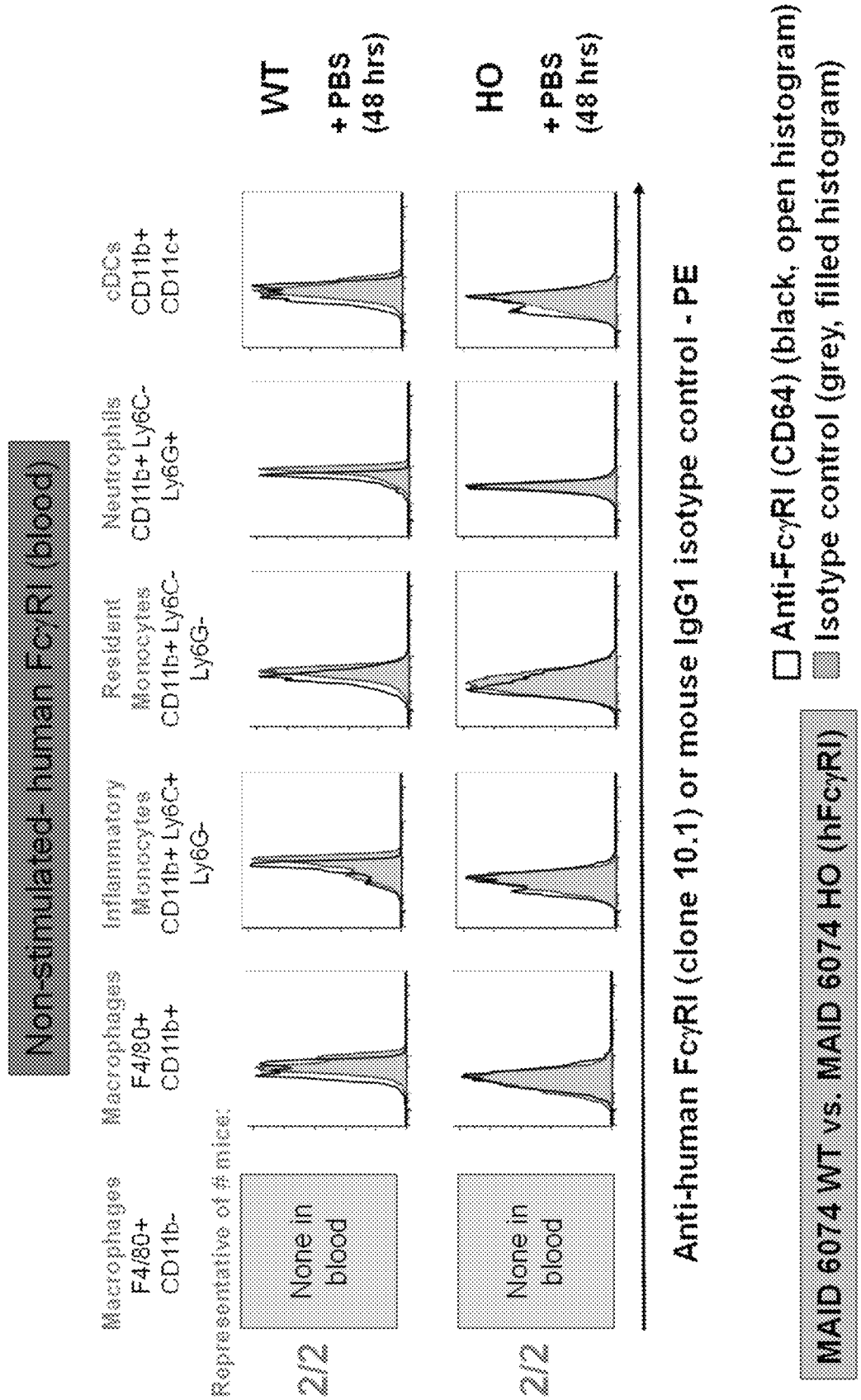
FIG. 19 shows a lack of human FcγRI expression in the blood of MAID 6074 WT mice and MAID 6074 HO mice 48 hours after treatment with PBS.
Figure 20:
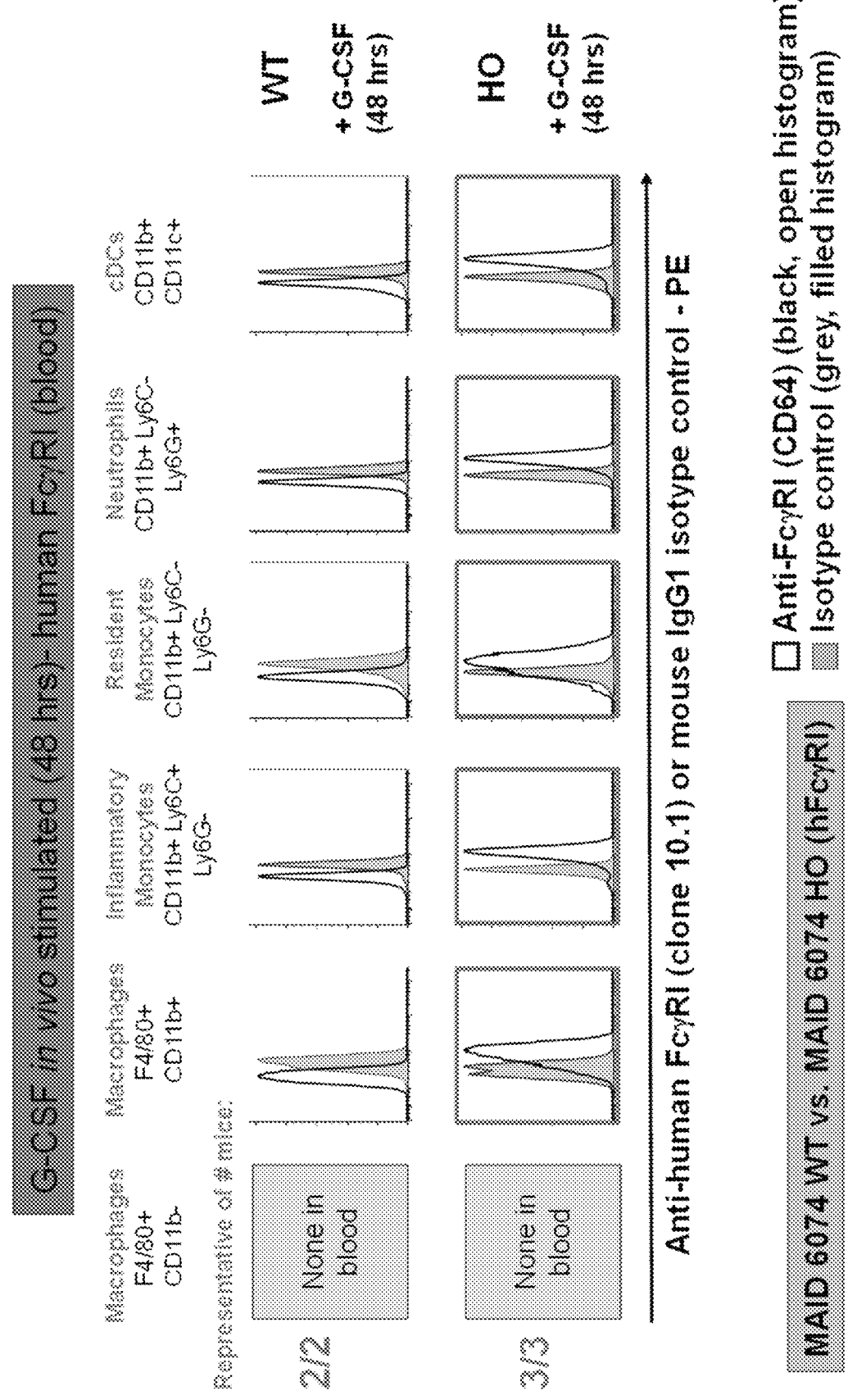
FIG. 20 shows human FcγRI expression in the blood of MAID 6074 HO mice compared to MAID 6074 WT mice 48 hours after treatment with mG-CSF.
Figure 21:
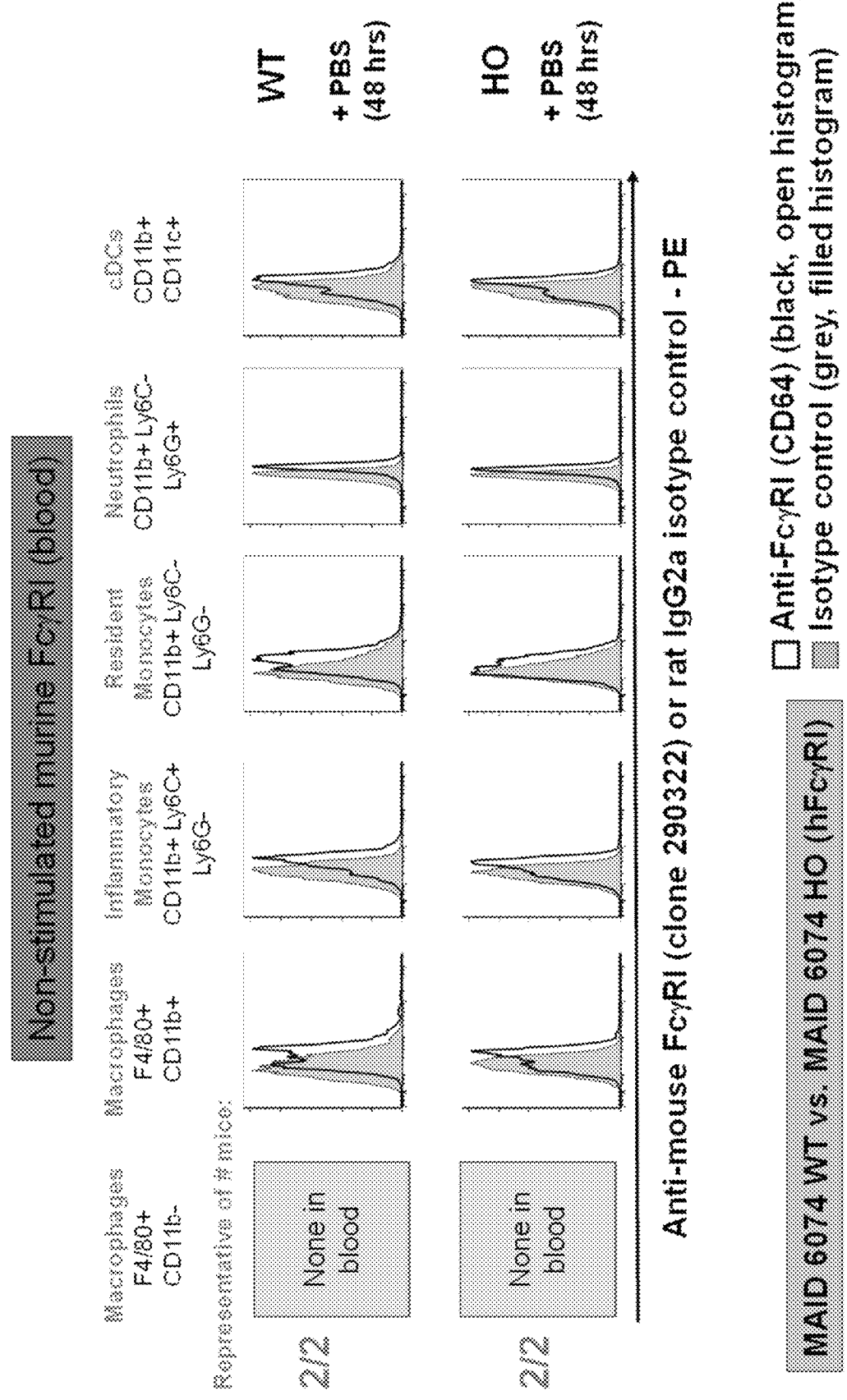
FIG. 21 shows lack of murine FcγRI expression in the blood of MAID 6074 WT and MAID 6074 HO mice 48 hours after treatment with PBS.
Figure 22:
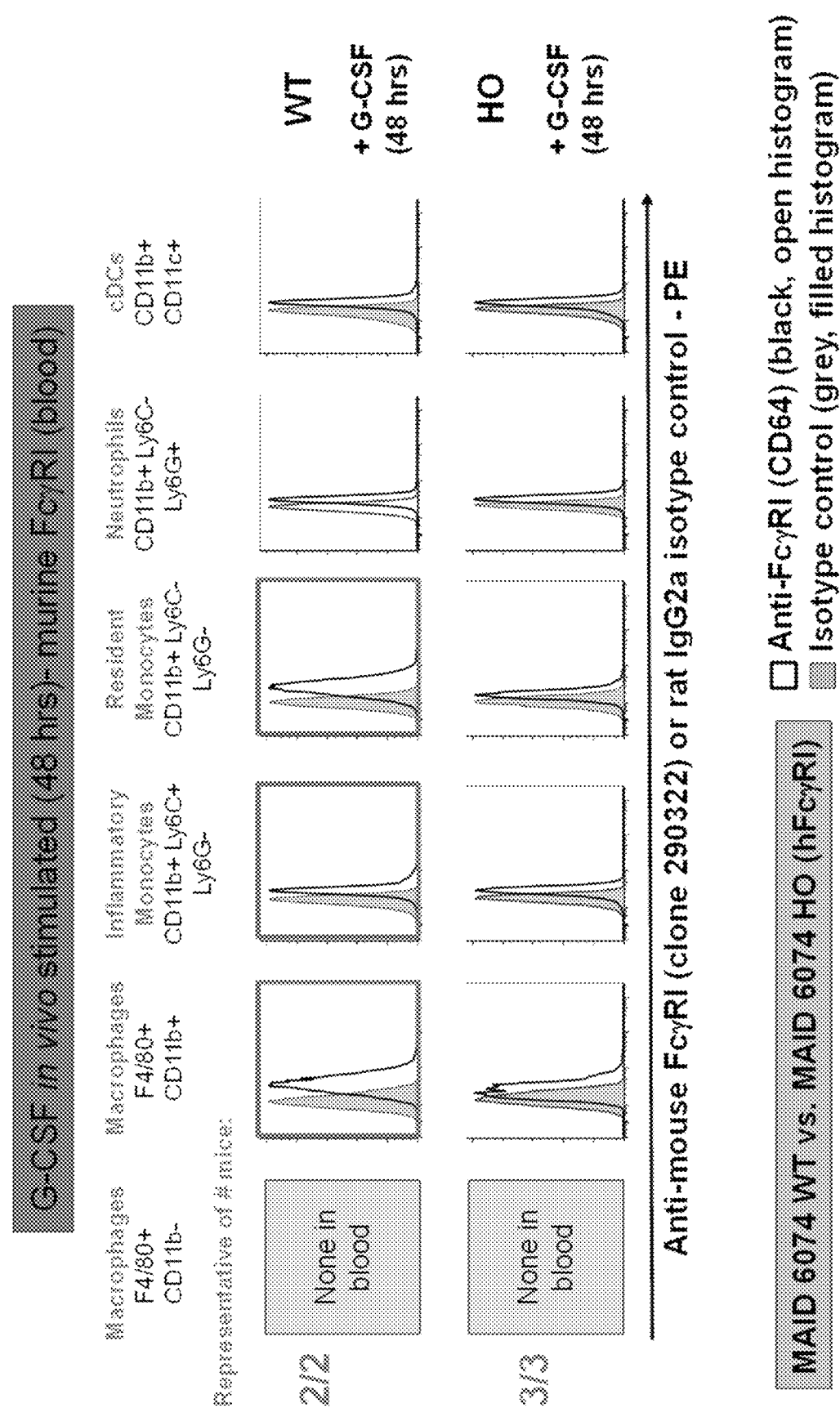
FIG. 22 shows murine FcγRI expression in the blood of MAID 6074 WT compared to MAID 6074 HO mice 48 hours after treatment with mG-CSF.
Figure 23:
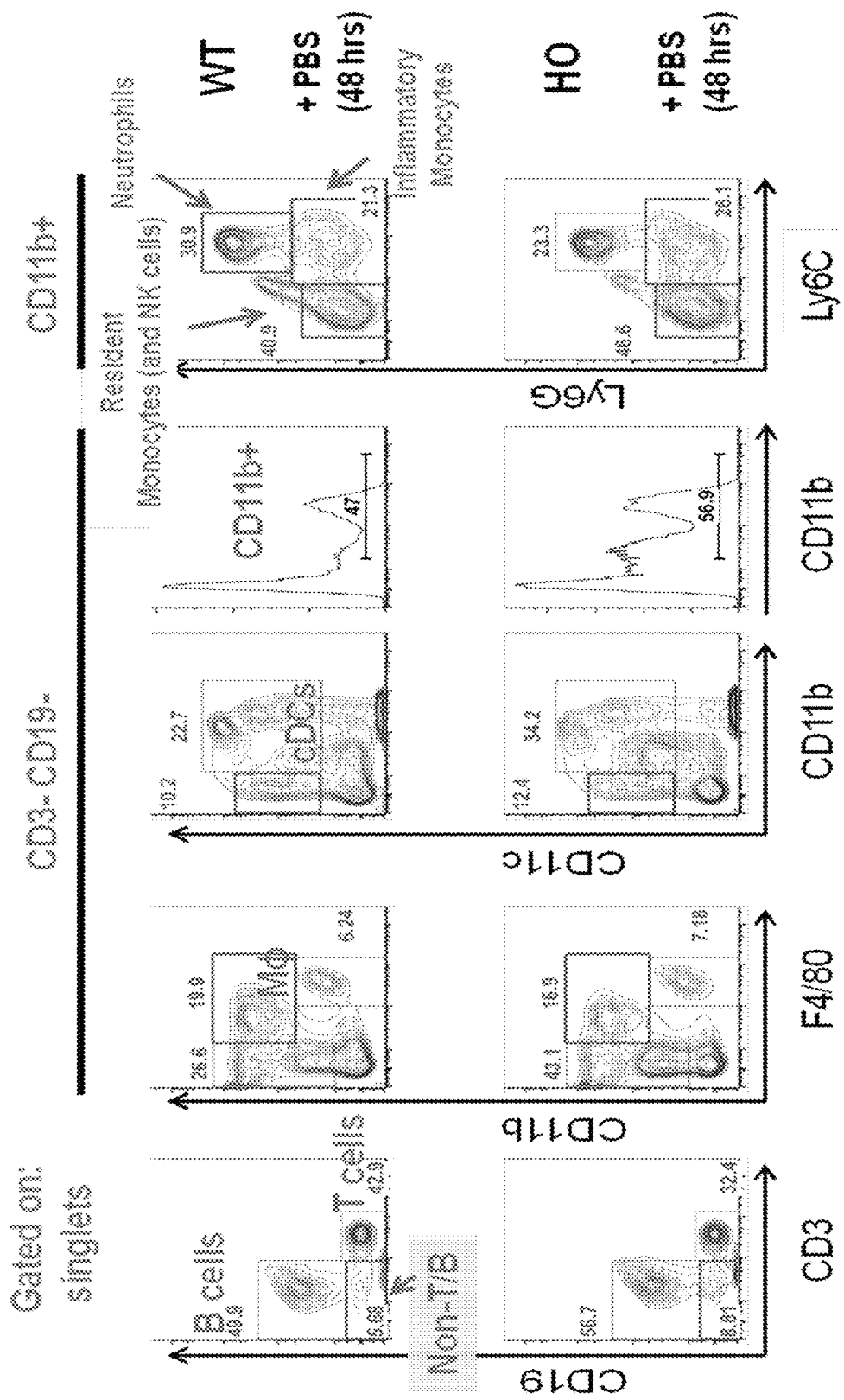
FIG. 23 shows myeloid splenic populations in MAID 6074 HO compared to MAID 6074 WT mice 48 hours after treatment with PBS.
Figure 24:
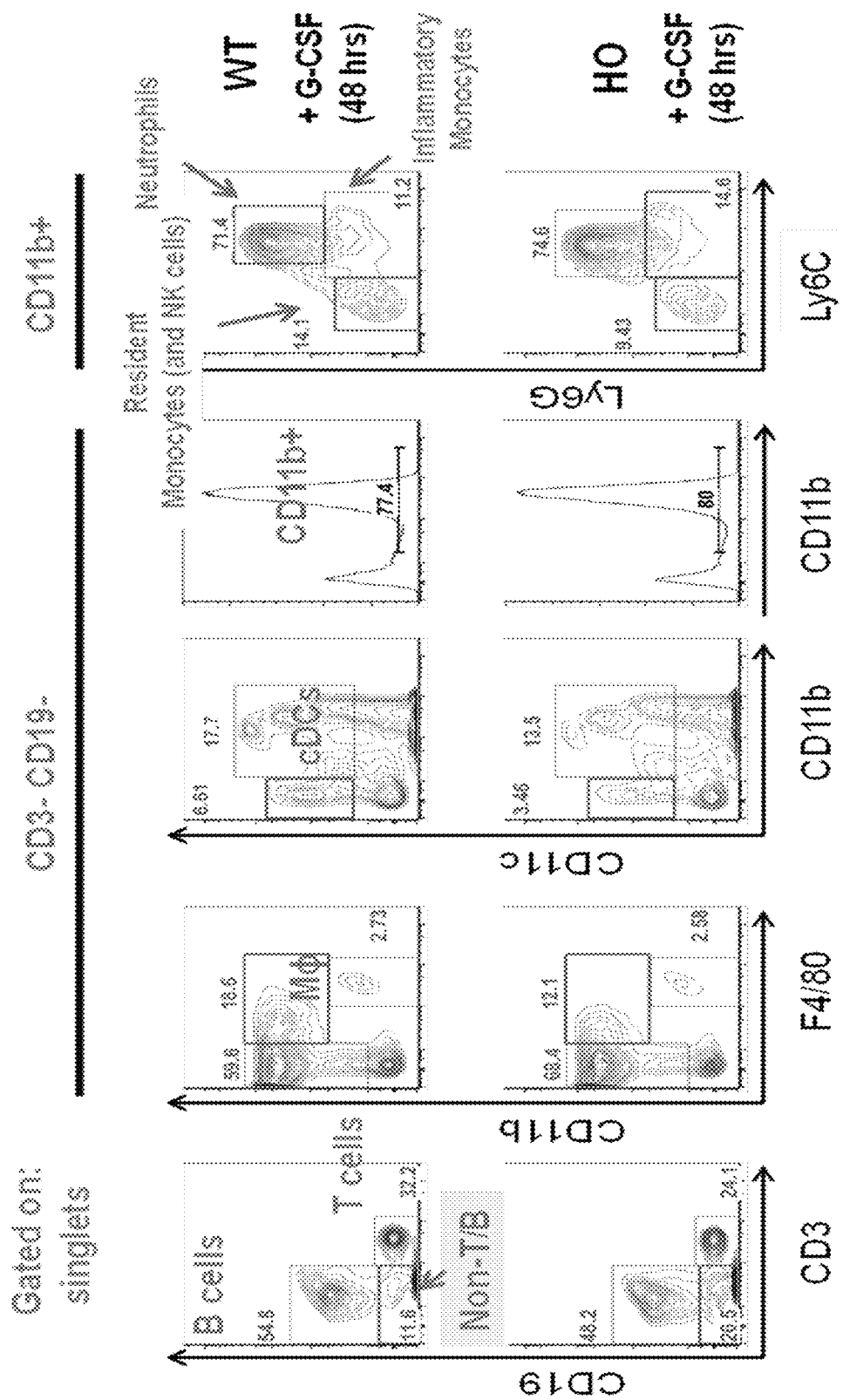
FIG. 24 shows myeloid splenic populations in MAID 6074 HO mice compared to MAID 6074 WT mice 48 hours after treatment with mG-CSF.
Figure 25:
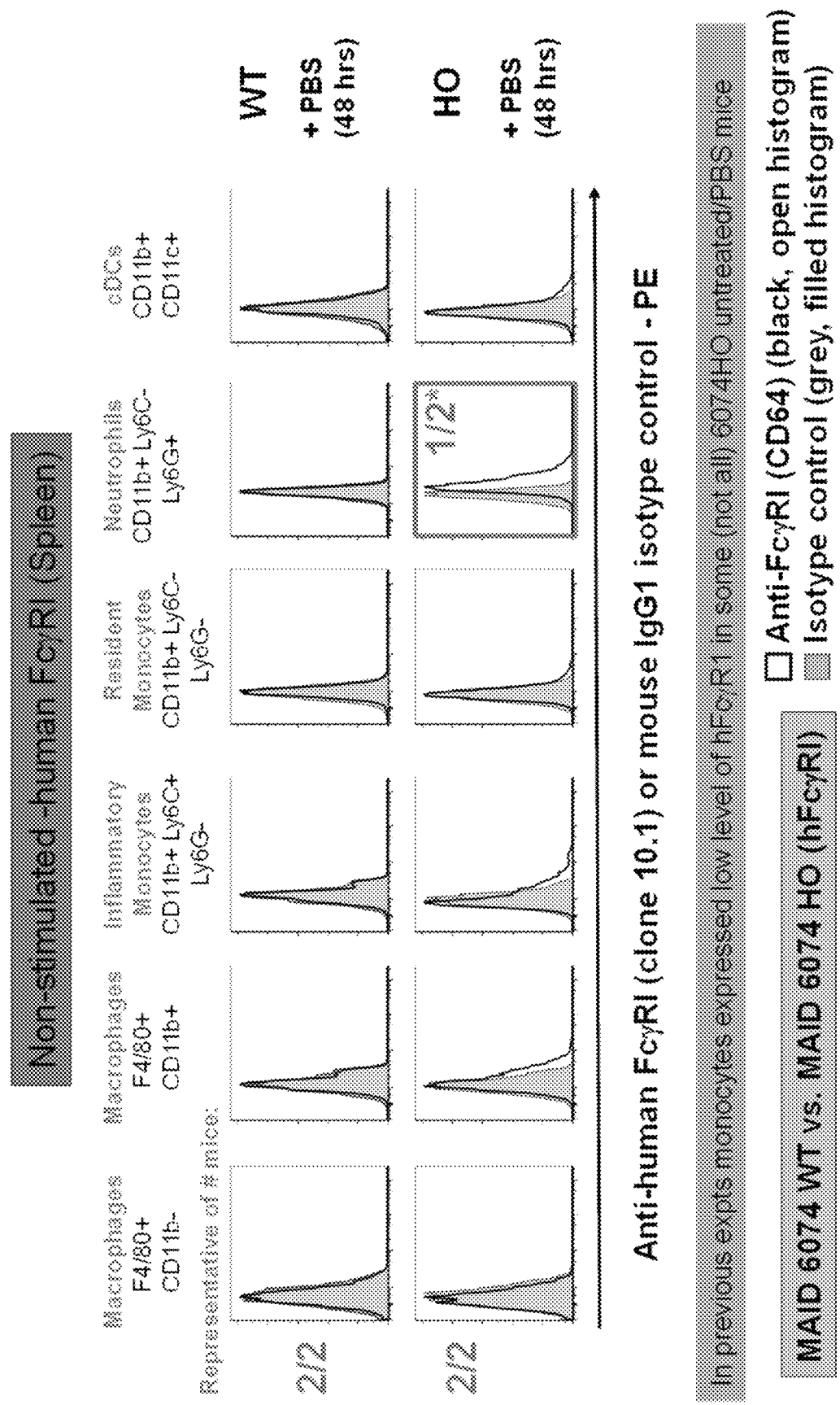
FIG. 25 shows a lack of human FcγRI expression in splenic monocytes in MAID 6074 HO mice and 6074 WT mice 48 hours after treatment with PBS.
Figure 26:
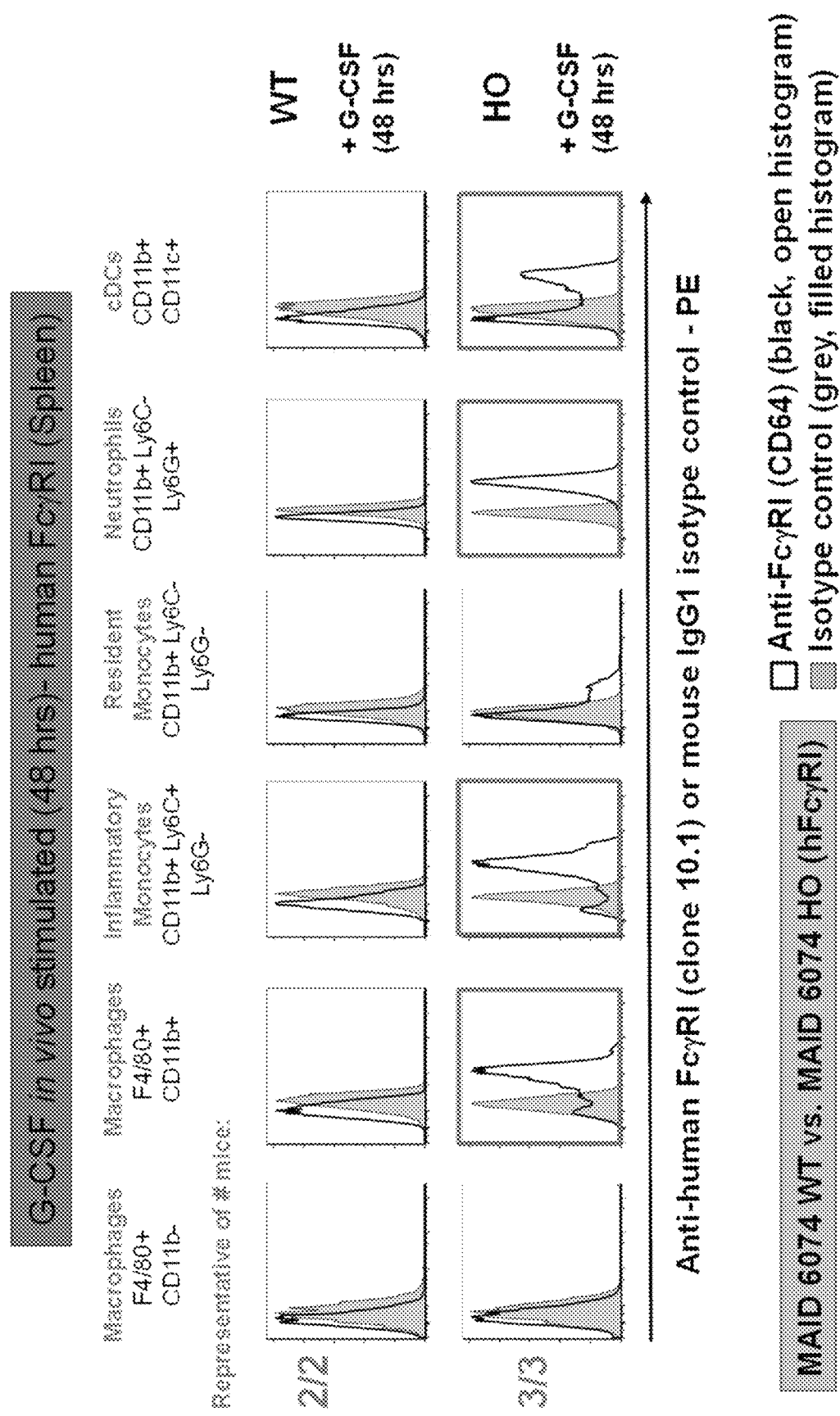
FIG. 26 shows human FcγRI expression in the spleen of MAID 6074 HO mice compared to MAID 6074 WT mice 48 hours after treatment with mG-CSF.
Figure 27:
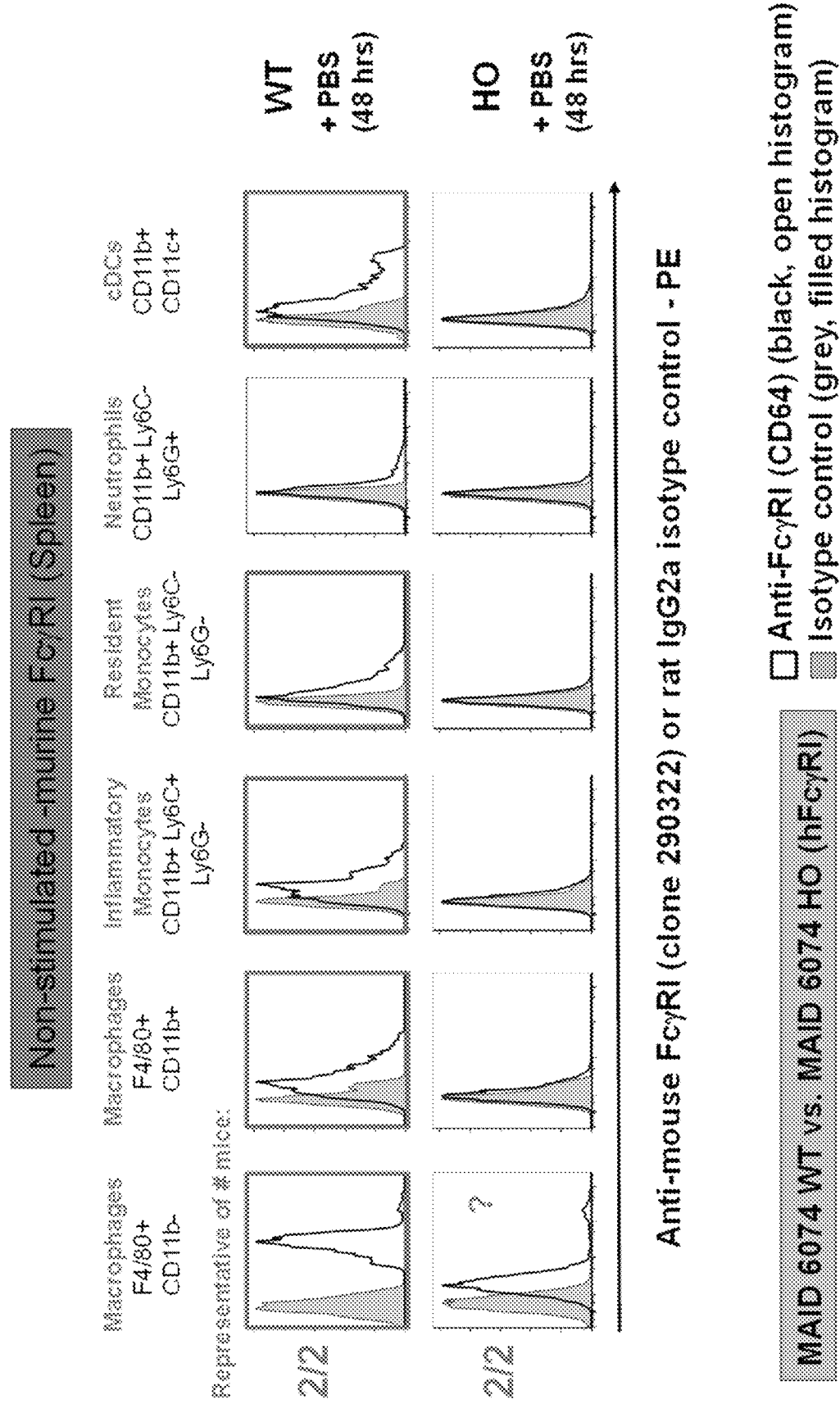
FIG. 27 shows murine FcγRI expression in the spleen of MAID 6074 WT mice compared to MAID 6074 HO mice 48 hours after treatment with PBS.
Figure 28:
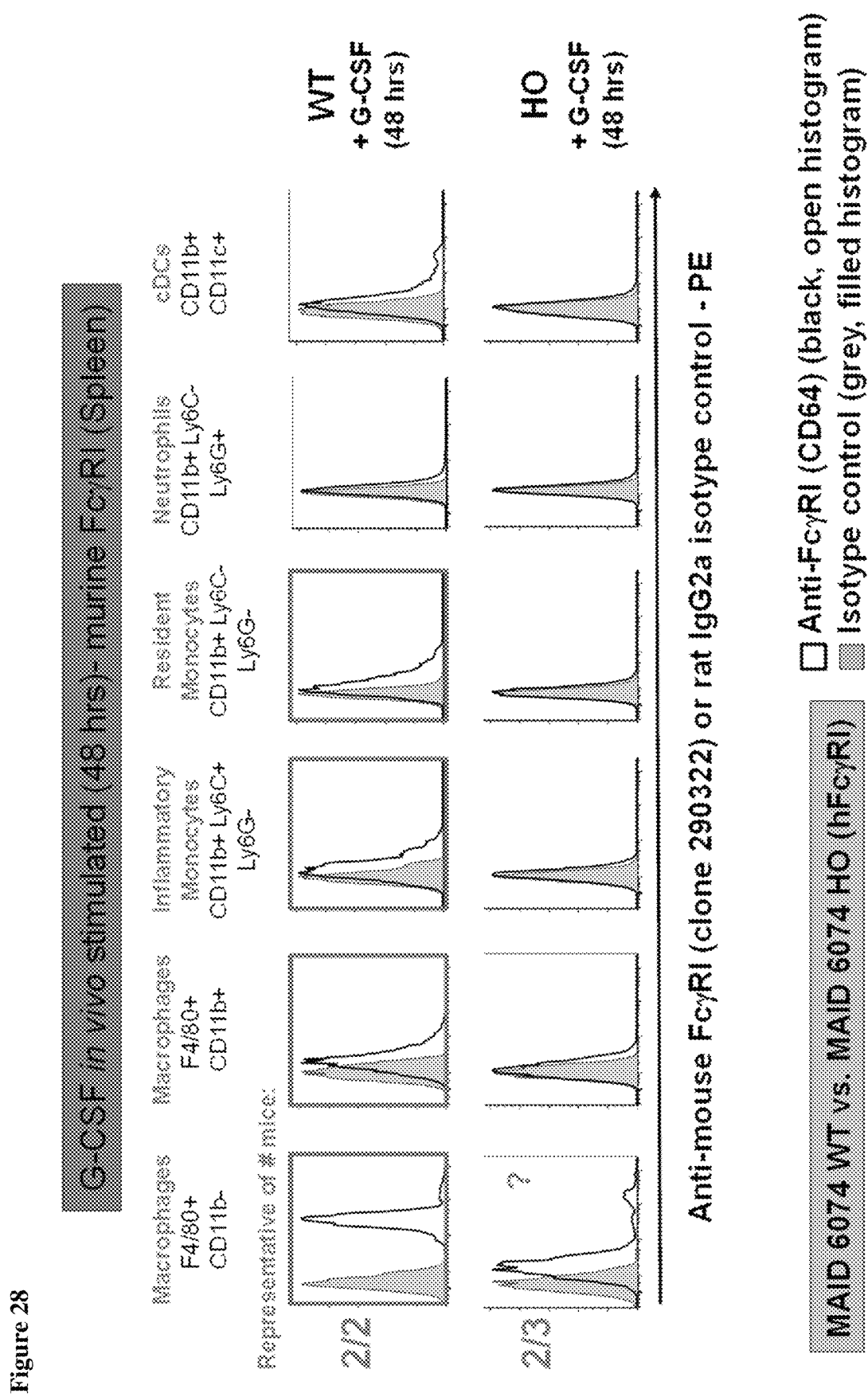
FIG. 28 shows murine FcγRI expression in the spleen of MAID 6074 WT mice compared to MAID 6074 HO mice 48 hours after treatment with mG-CSF.
Figure 29:
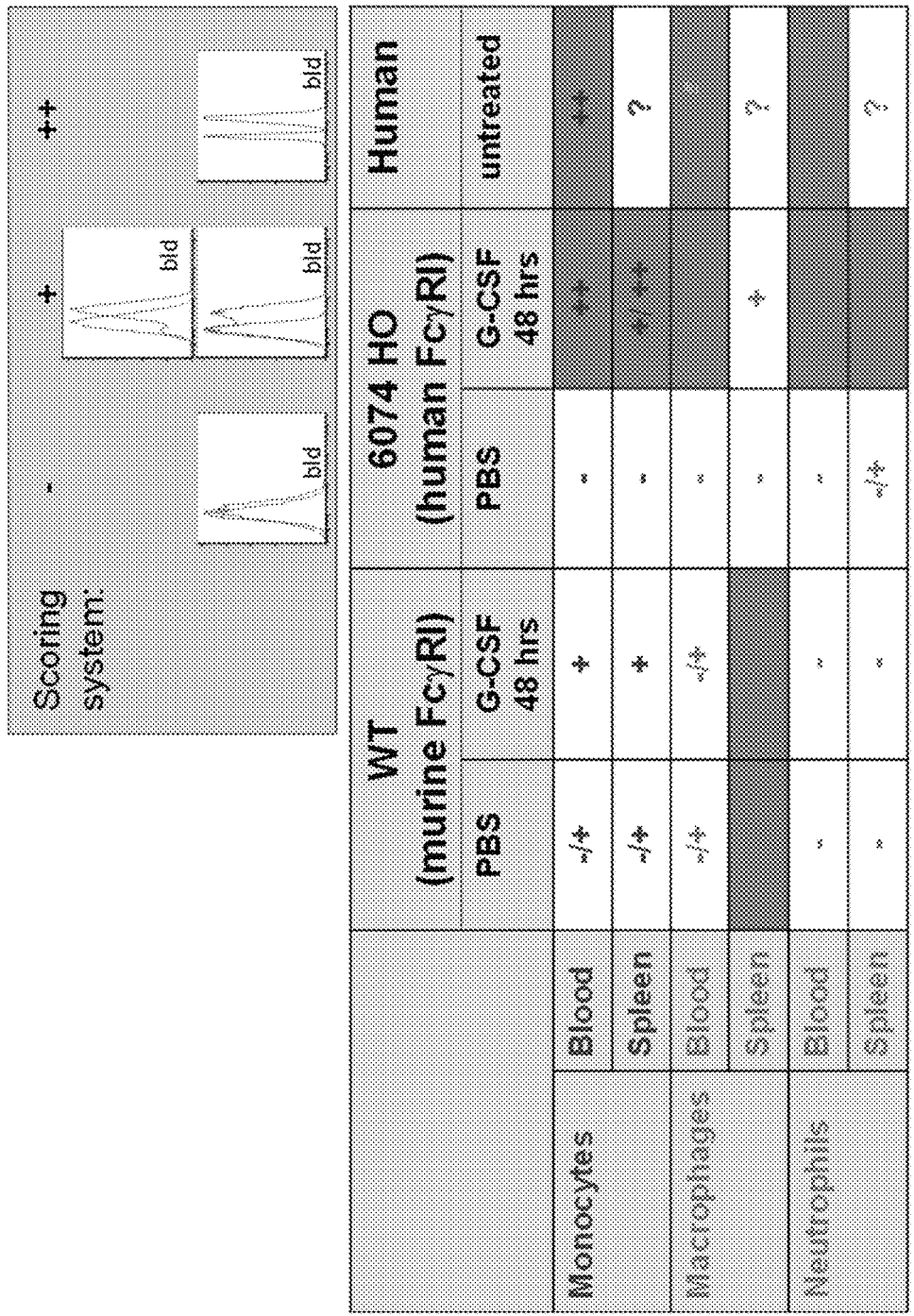
FIG. 29 shows a summary of human FcγRI expression in cell populations of MAID 6074 WT and MAID 6074 HO mice after treatment with PBS or mG-CSF.
Figure 30:
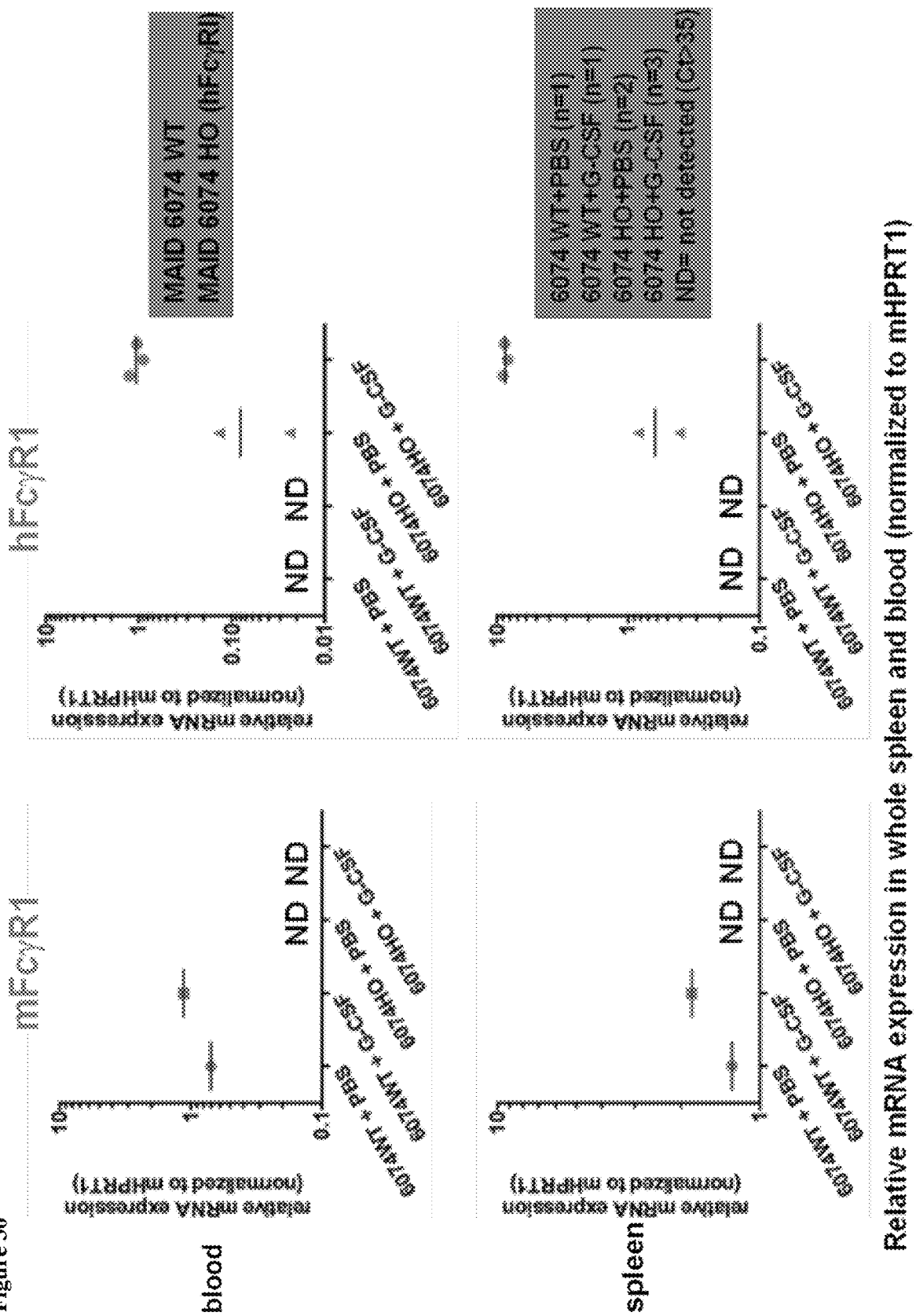
FIG. 30 shows upregulation of human FcγRI mRNA induced by mG-CSF in MAID 6074 HO mouse blood and spleen normalized to mHPRT1.
Figure 31:
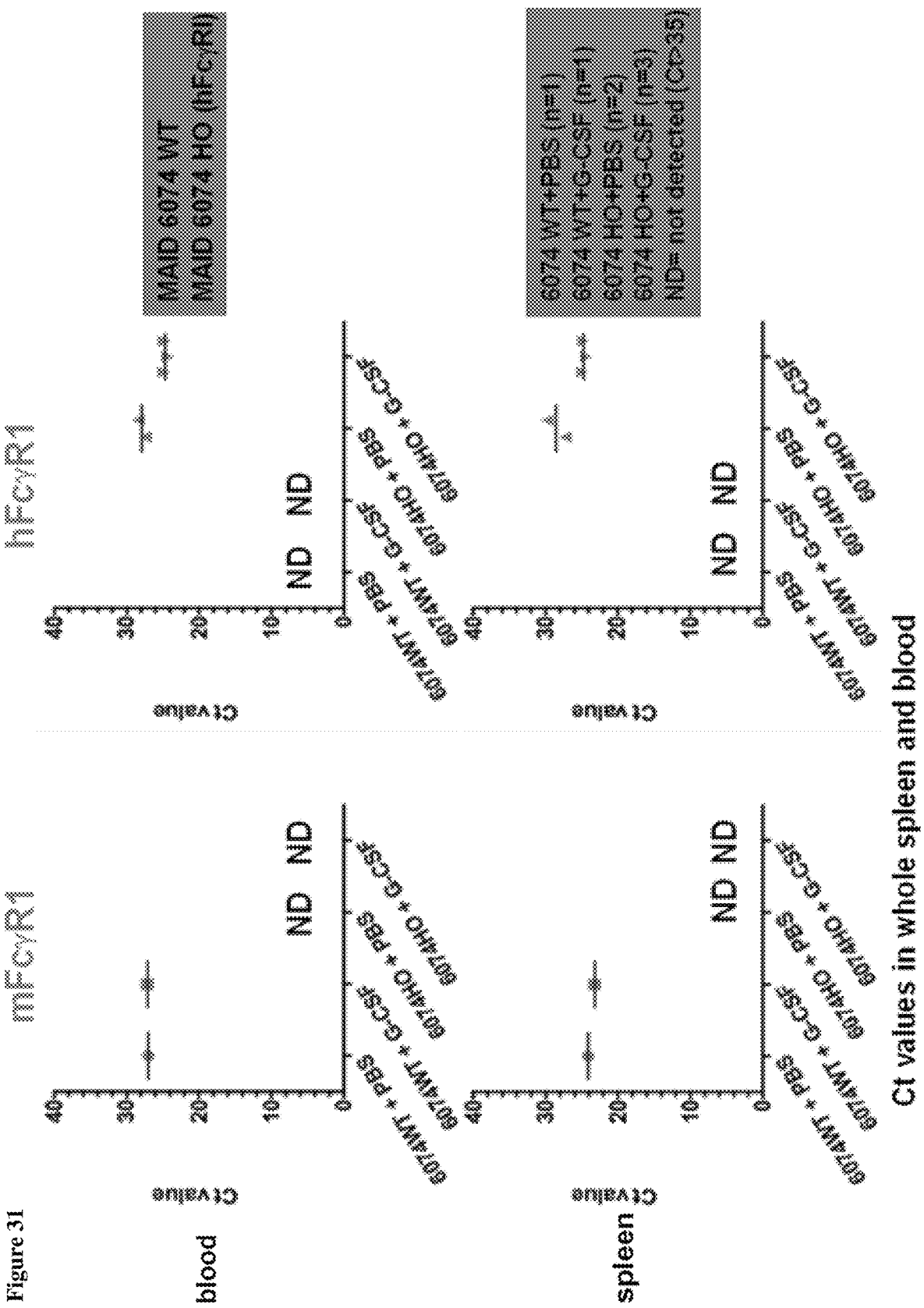
FIG. 31 shows upregulation of human FcγRI mRNA induced by mG-CSF in MAID 6074 HO mouse blood and spleen.
Figure 32:
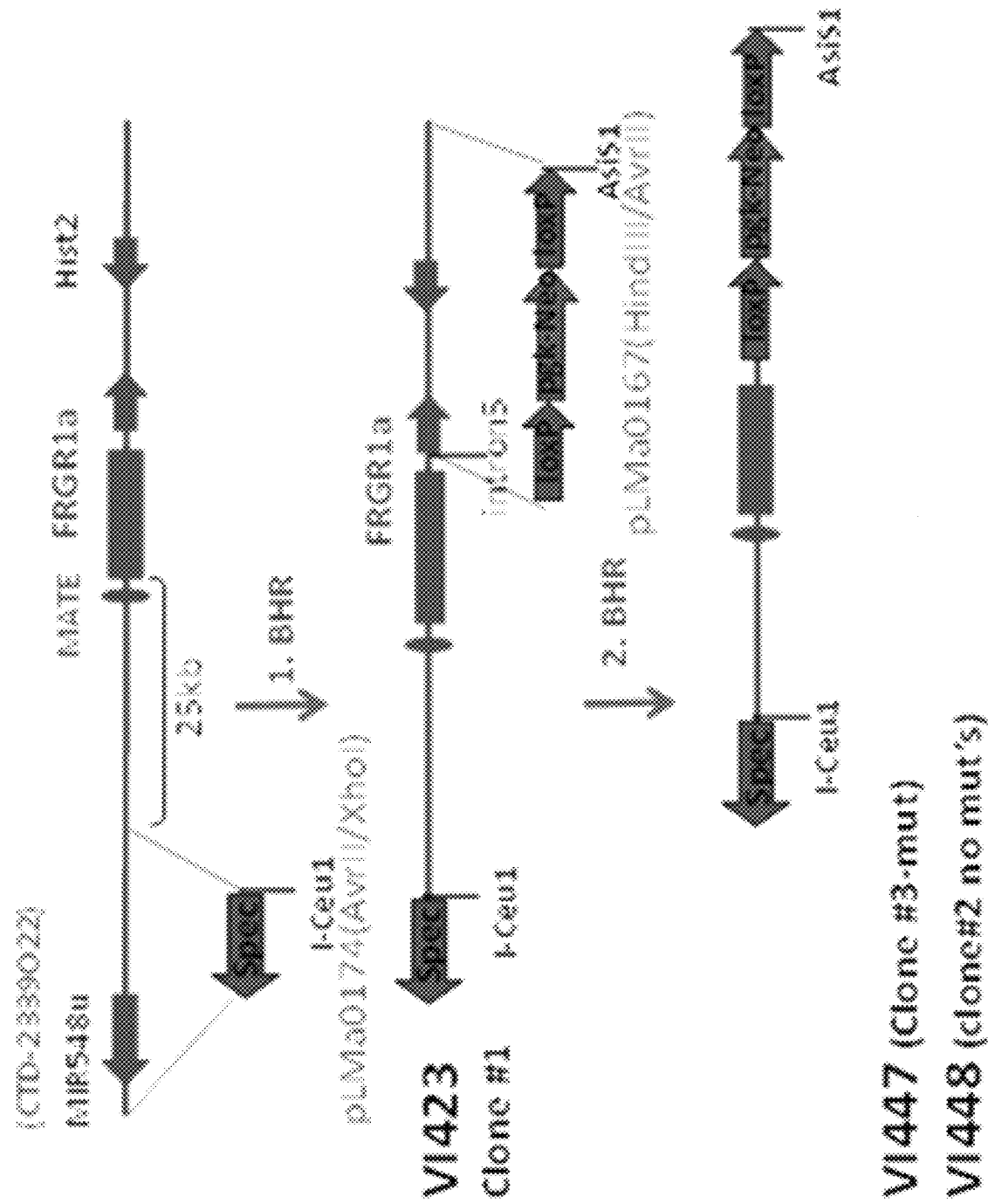
FIG. 32 depicts a schematic for and exemplary strategy for the humanization of mouse FcγRI.
Figure 32:
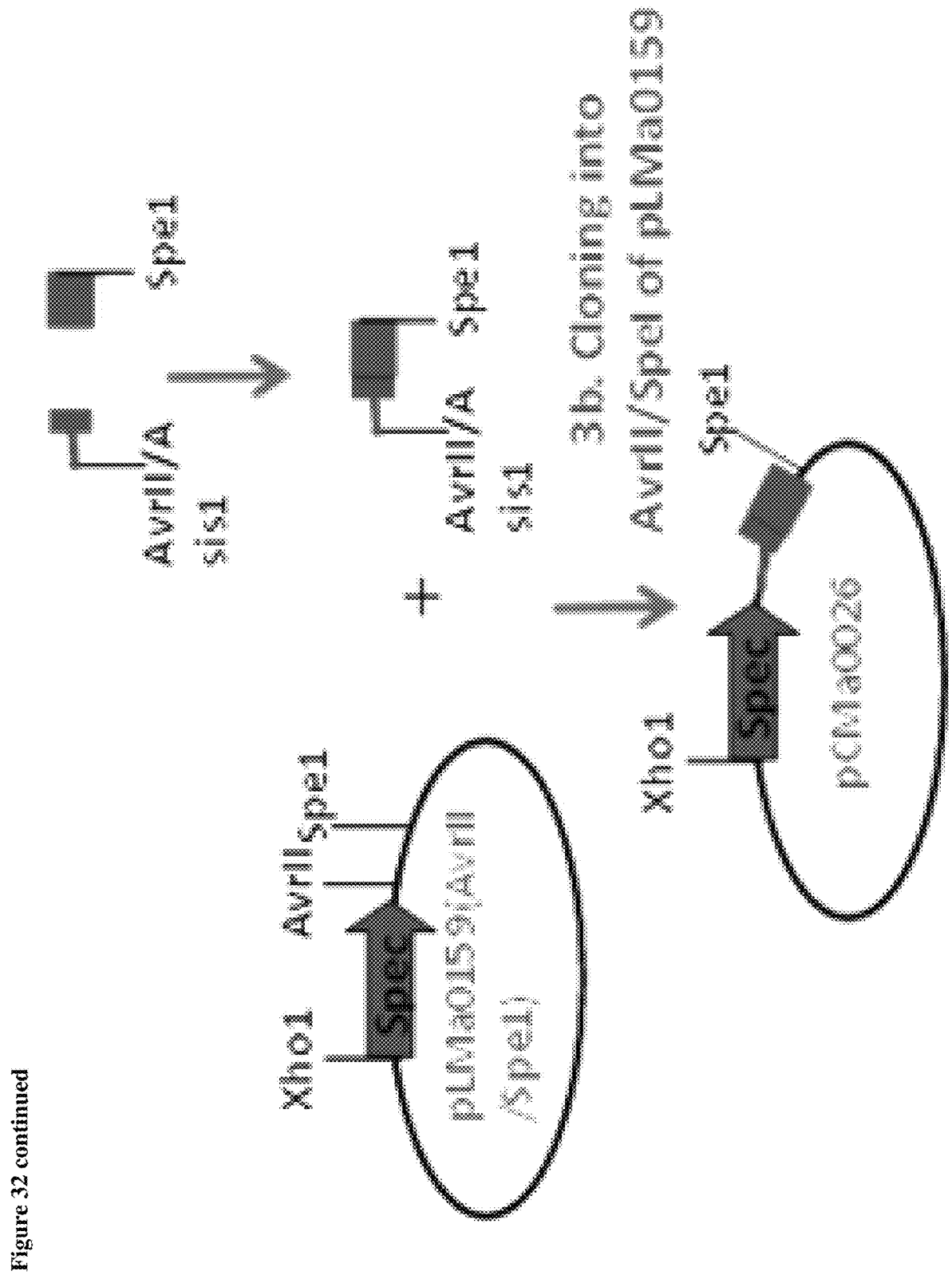
Figure 32:
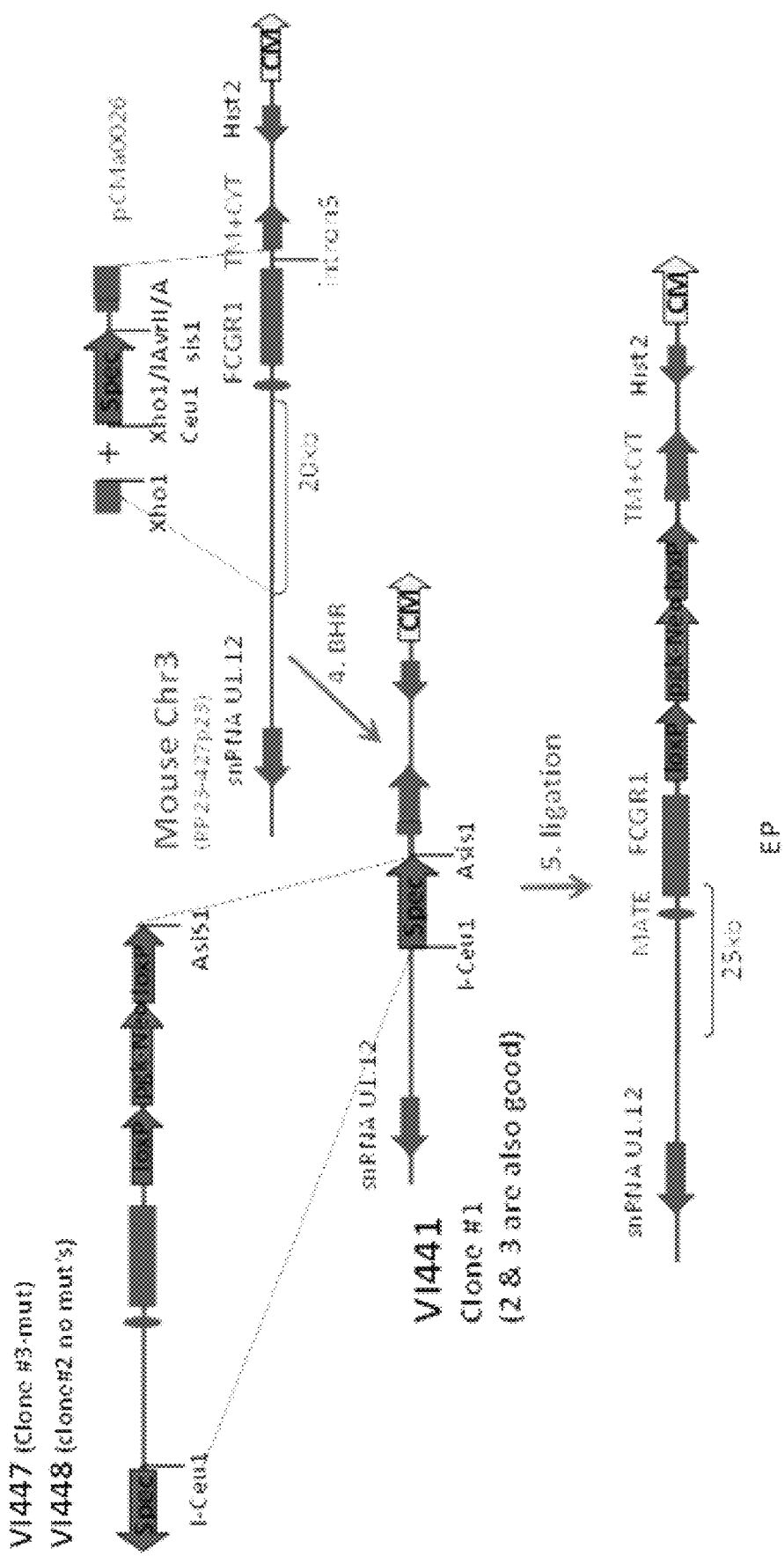

FIG. 32 depicts a schematic for and exemplary strategy for the humanization of mouse FcγRI. MAID6074 is the cassette removed version of MAID6073. The junction sequences are shown in FIG. 6.

Selection of Targeted Mouse ES Cells

The MAID 6074 LTVEC was electroporated into the mouse ES cell line F1H4.

Example 2. Generation of High Affinity FcγRI Humanized Mice

This example illustrates transformation and breeding of mice. hFcgR1 ecto domain (MAID 6073) LTVEC was electroporated into parental F1H4 mouse Embryonic Stem (ES) cells. Colonies surviving G418 drug selection were picked and screened for the homologous recombination of human FcγRI sequence into the FcγRI mouse locus. Eight clones were identified to have the appropriate modification and being heterozygous for human FcγRI ecto domain, one of which was clone 6073F-D2. All these clones contained the neo cassette.

Clone 6073F-D2 was electroporated with 2 μg of Cre plasmid to remove the neo cassette. The colonies were picked and then screened for the absence of the neo cassette. Of the clones determined to have the neo cassette removed, ES clones 6074B-A1 and 6074B-A10 were micro-injected using the VelociMouse method.

Male and female (XY female) F0 VelociMice were generated from clones 6074B-A1 and 6074B-A10. These F0 mice were bred to each other in clonal and non-clonal pairings. F1 mice were produced and these mice were shown to be heterozygous and homozygous (and wildtype) for the human FcγRI. The F1 mice appeared normal and the ratio of Hom:Het:WT mice followed the predicted Mendelian ratio of 1:2:1. Cohorts of males and females being wild-type and homozygous for human FcγRI were transferred for study.

Example 3. Characterization of High Affinity FcγRI Humanized Mice

This example illustrates the characteristic expression of high affinity FcγRI protein on the surface of cells from non-human animals engineered to contain an humanized FcγRI gene construct as described in Example 1 at an endogenous FcγRI locus.

Figure 2:
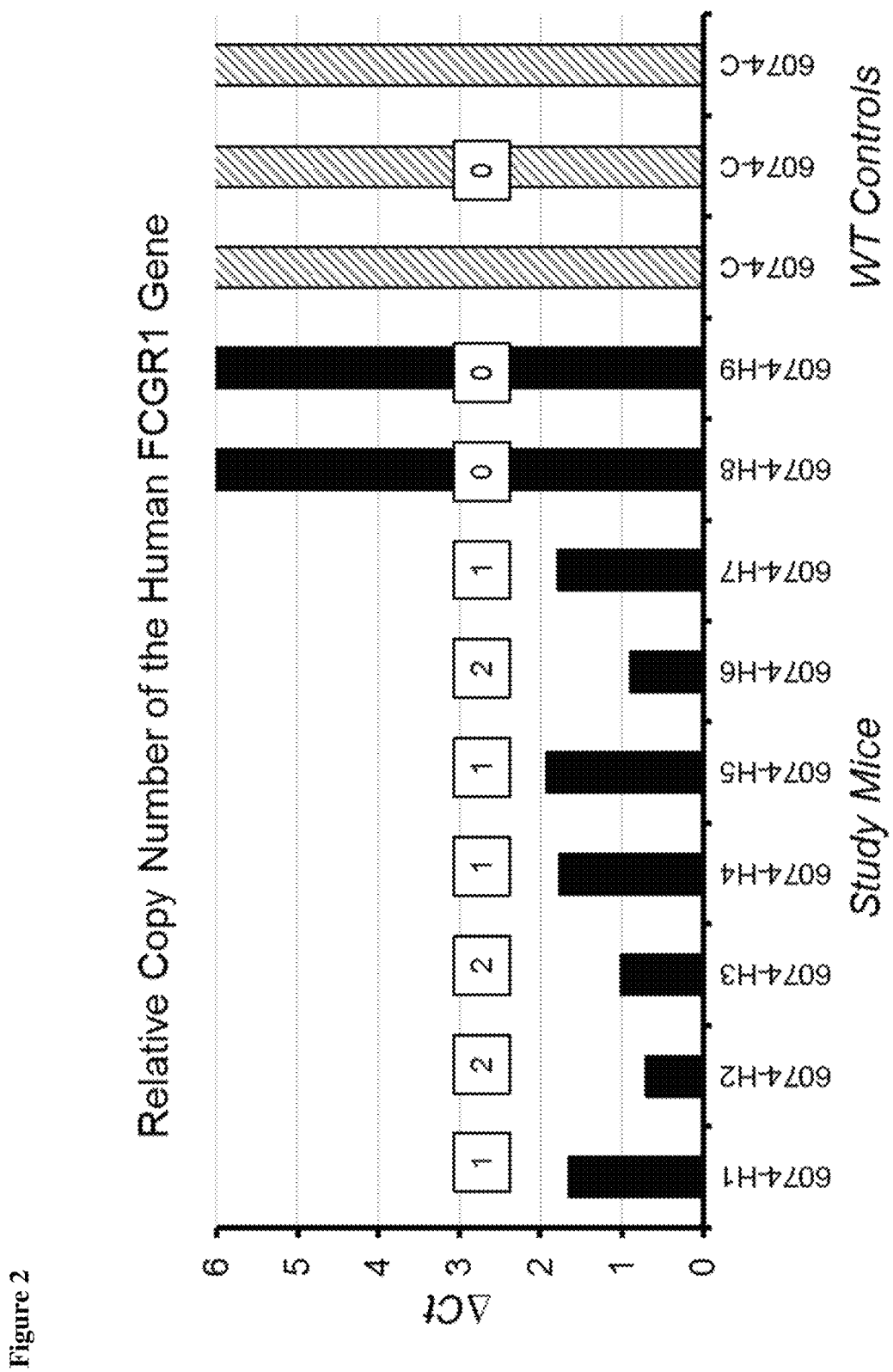
FIG. 2 shows relative copy number of the human FcγRI gene in experimental mice and wild-type controls.
Figure 3:
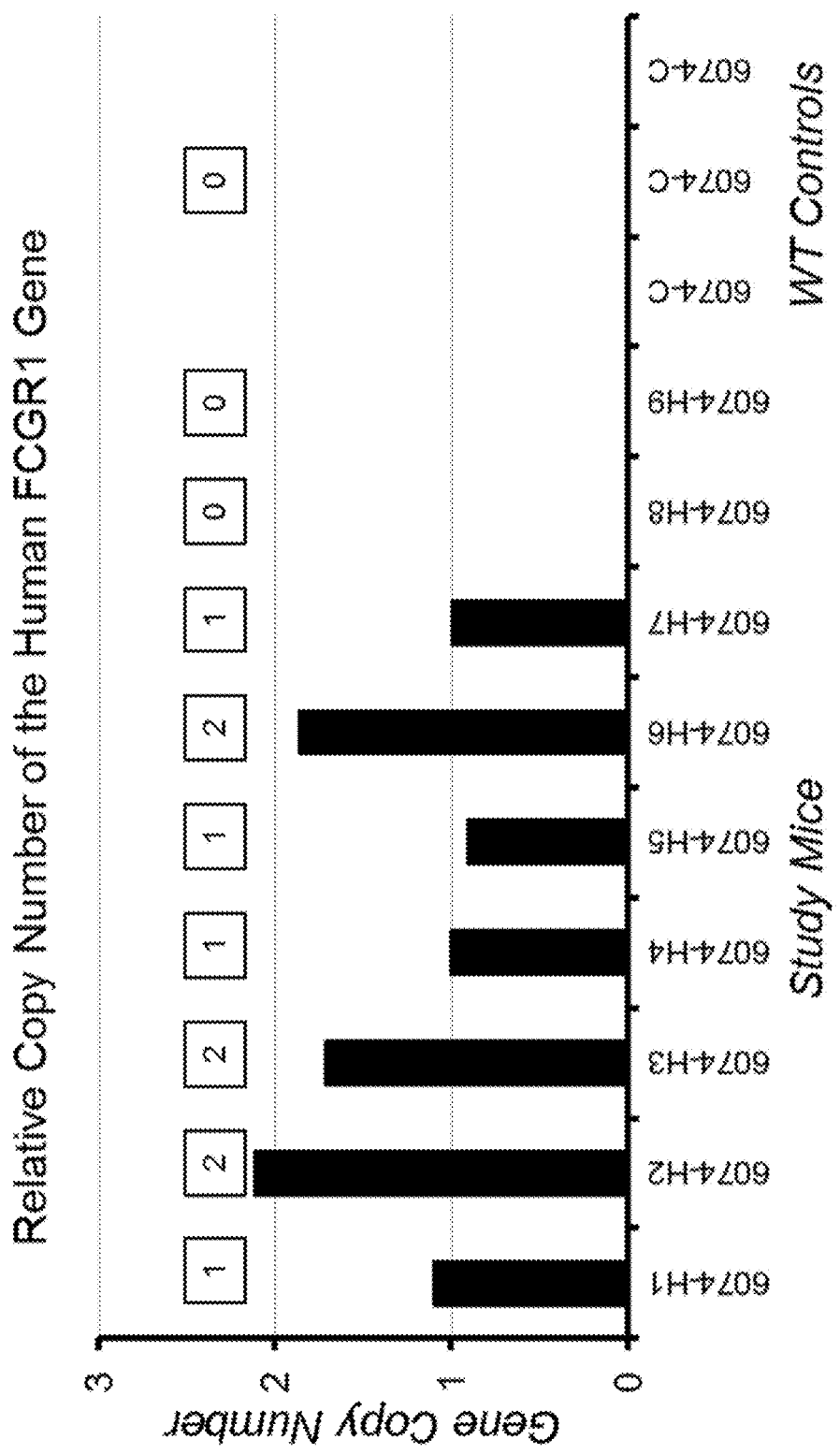
FIG. 3 shows transformed data for gene copy numbers based on Het (+/−) mice having one copy of the human FcγRI and calibrated by average Act.
Figure 4:
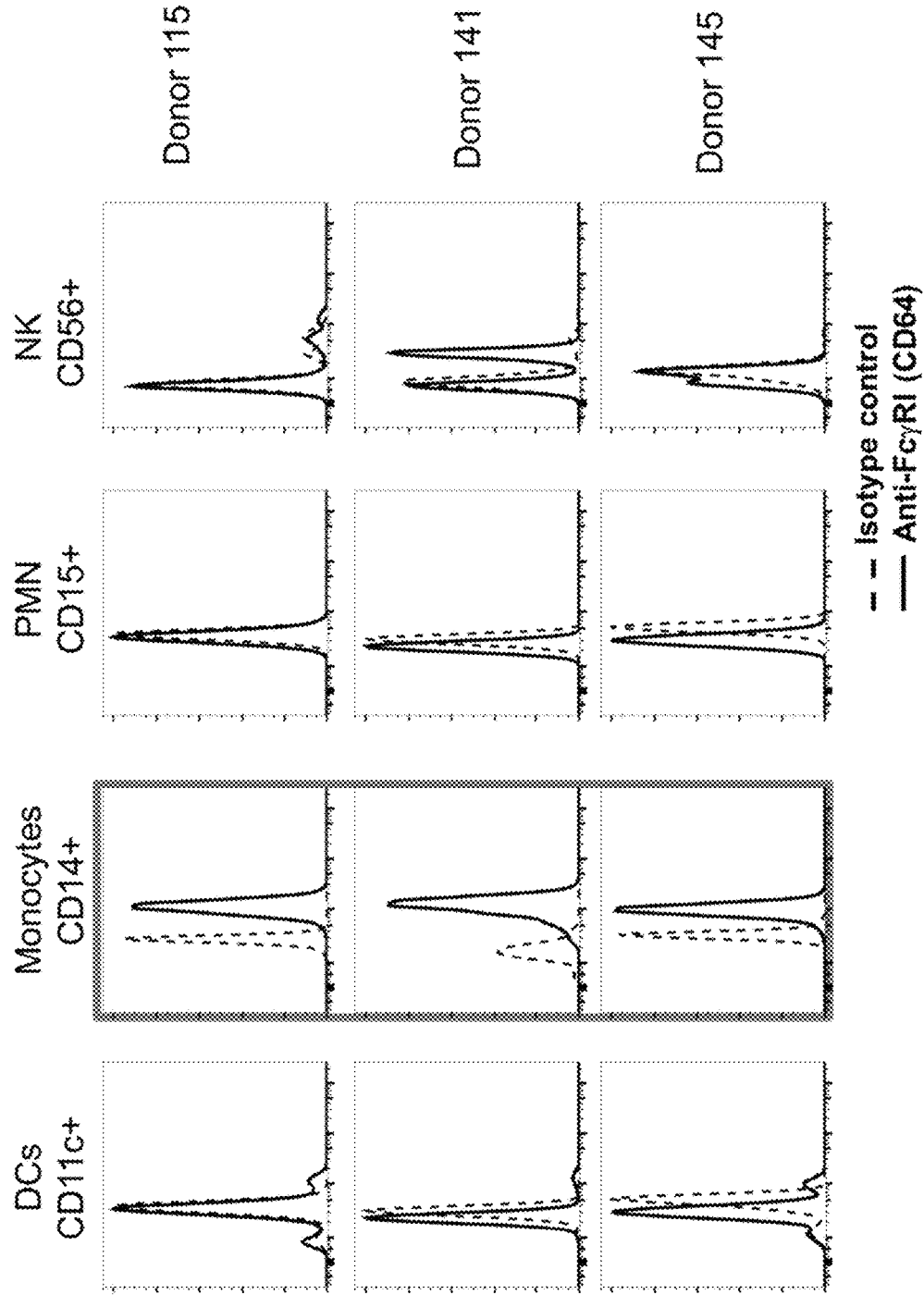
FIG. 4 shows expression of FcγRI receptors in cells from human blood donors.

Genotypic characterization of high affinity FcγRI humanized mice is shown in FIGS. 1-3. Transcript for mouse FcγRI is not detected in mice homozygous for humanized FcγRI.

The results of phenotypic characterization of are shown in FIGS. 4, and 7-16.

Example 4. Phenotypic Characterization of High Affinity FcγRI Humanized Mice Treated with Murine Granulocyte Colony Stimulating Factor (mG-CSF)

Phenotypic analysis was performed for MAID 6074 (hFcγRI) HO mice treated with murine G-CSF (mG-CSF) vs. phosphate buffered saline (PBS) control. Mice were examined 48 hours after subcutaneous injection. Data is shown for 6-7 week old MAID 6074 WT mice treated with PBS (n=2) or mG-CSF (n=2) compared to MAID 6074 HO mice treated with PBS (n=2) or mG-CSF (n=3). Results were similar for 16-17 week old MAID 6074 WT mice treated with PBS (n=1) or mG-CSF (n=1) compared to MAID 6074 HO mice treated with PBS (n=1) or mG-CSF (n=1). Baseline (PBS) and mG-CSF induced expression of mouse or hybridized FcγRI in monocytes, macrophages, neutrophils and dendritic cells in blood and spleen of MAID 6074 WT and MAID 6074 HO mice are shown in FIGS. 17-31.

Untreated MAID 6074 HO mice express FcγRI (CD64) mRNA in blood, although protein was not detected by FACS. G-CSF (48 hrs) induced an increase in FcγRI (CD64) mRNA in blood and spleen, and protein as detected by FACS.

Example 5. Phenotypic Characterization of Mice Expressing Humanized High and Low Affinity Fcγ Receptors Mice were generated that expressed humanized high affinity and low affinity Fcγ receptors by using standard breeding techniques. Specifically, mice expressing humanized high affinity FcγRI generated as described in Examples 1 and 2 were crossed with mice expressing humanized low affinity FcγRIIa, FcγRIIb, FcγRIIc, FcγRIIIa and FcγRIIIb generated as described in Examples 1-6 and FIGS. 1-6 of U.S. Pat. App. Pub. No. 2014/0154701, which is hereby incorporated by reference. The resulting mice were bred to homozygosity.

Phenotypic analysis was performed on the humanized high and low affinity FcγR mice following treatment with murine G-CSF (mG-CSF) or a phosphate buffered saline (PBS) control. Mice were administered a subcutaneous injection of PBS or mG-CSF (62 μg s.c., single dose). After 48 hours, blood and spleens from the treated mice were harvested and phenotypically characterized by FACS as described in Example 4. The cell surface phenotype of the humanized high and low affinity FcγR mice was similar to the phenotype observed for the high affinity FcγR humanized mice. Also similar to the high affinity Fcγ receptor humanized mice, the mice in which both the high and low affinity Fcγ receptor were humanized showed increased expression of human FcγRI in blood and splenic monocytes, macrophages and neutrophils. In summary, humanization of the low affinity Fcγ receptors in the FcγRI humanized mice produced no significant phenotypic change.

EQUIVALENTS

Having thus described several aspects of at least one embodiment of this invention, it is to be appreciated by those skilled in the art that various alterations, modifications, and improvements will readily occur to those skilled in the art.

Such alterations, modifications, and improvements are intended to be part of this disclosure, and are intended to be within the spirit and scope of the invention. Accordingly, the foregoing description and drawing are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

Those skilled in the art will appreciate typical standards of deviation or error attributable to values obtained in assays or other processes described herein.

What is claimed is:

1. A mouse whose genome comprises an FcγRI gene at an endogenous FcγRI locus, wherein the FcγRI gene encodes a functional FcγRI protein comprising an extracellular portion of a human FcγRI α chain and an intracellular portion of a mouse FcγRI α chain, wherein the mouse expresses the functional FcγRI protein encoded by the FcγRI gene on monocytes, macrophages, neutrophils or dendritic cells, and wherein the mouse expresses an endogenous FcR γ-chain.

2. The mouse of claim 1, wherein the extracellular portion of a human FcγRI α chain comprises an EC1 domain, EC2 domain, an EC3 domain, or a combination thereof.

3. The mouse of claim 2, wherein the EC1 domain is encoded by an exon at least 90% identical to exon 3 of SEQ ID NO: 3.

4. The mouse of claim 2, wherein the EC2 domain is encoded by an exon at least 90% identical to exon 4 of SEQ ID NO: 3.

5. The mouse of claim 2, wherein the EC3 domain is encoded by an exon at least 90% identical to exon 5 of SEQ ID NO: 3.

6. The mouse of claim 1, wherein the mouse does not detectably express a full-length mouse FcγRI α chain.

7. The mouse of claim 1, wherein the intracellular portion of an FcγRI α chain comprises a cytoplasmic domain of a mouse FcγRI α chain in whole or in part.

8. The mouse of claim 1, wherein the FcγRI protein further comprises a mouse FcγRI α chain transmembrane domain in whole or in part.

9. The mouse of claim 1, wherein the expression of the FcγRI protein is increased upon administration of murine granulocyte colony stimulating factor (mG-CSF) to the mouse.

10. A mouse comprising an FcγRI gene at an endogenous FcγRI locus, wherein the FcγRI gene comprises at least one exon of a human FcγRI gene encoding an extracellular portion of human FcγRI protein operably linked to at least one exon of a mouse FcγRI gene encoding an intracellular portion of a mouse FcγRI protein, wherein the mouse expresses a functional FcγRI protein encoded by the FcγRI gene on monocytes, macrophages, neutrophils or dendritic cells, and wherein the mouse expresses an endogenous FcR γ-chain.

11. The mouse of claim 10, wherein the FcγRI gene comprises exons 3, 4 and 5 of a human FcγRI gene.

* * * * *